US008367829B2

(12) United States Patent
Baker et al.

(10) Patent No.: US 8,367,829 B2
(45) Date of Patent: Feb. 5, 2013

(54) BI-FUNCTIONAL PYRAZOLOPYRIDINE COMPOUNDS

(75) Inventors: William R. Baker, Bellevue, WA (US); Shaopei Cai, Seattle, WA (US); Joshua Aaron Kaplan, Seattle, WA (US); Musong Kim, Bothell, WA (US); Gary Phillips, Issaquah, WA (US); Lafe J. Purvis, II, Seattle, WA (US); Marcin Stasiak, Seattle, WA (US); Kirk L. Stevens, Bothell, WA (US); Josh Van Veldhuizen, Seattle, WA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 13/103,598

(22) Filed: May 9, 2011

(65) Prior Publication Data

US 2011/0275623 A1 Nov. 10, 2011

Related U.S. Application Data

(60) Provisional application No. 61/333,031, filed on May 10, 2010, provisional application No. 61/406,933, filed on Oct. 26, 2010, provisional application No. 61/477,264, filed on Apr. 20, 2011.

(51) Int. Cl.
C07D 513/02 (2006.01)
(52) U.S. Cl. ...................................................... 546/119
(58) Field of Classification Search .................. 514/303; 546/119
See application file for complete search history.

(56) References Cited

U.S. PATENT DOCUMENTS

| | | | |
|---|---|---|---|
| 3,885,047 A | 5/1975 | Seidehamel et al. |
| 4,145,542 A | 3/1979 | Nakagawa et al. |
| 4,761,421 A | 8/1988 | Muir |
| 4,992,474 A | 2/1991 | Skidmore et al. |
| 5,455,252 A | 10/1995 | Wilhelm et al. |
| 5,712,298 A | 1/1998 | Amschler |
| 5,728,712 A | 3/1998 | Montana et al. |
| 5,776,983 A | 7/1998 | Washburn et al. |
| 5,804,588 A | 9/1998 | Dyke et al. |
| 5,834,485 A | 11/1998 | Dyke et al. |
| 6,051,576 A | 4/2000 | Ashton et al. |
| 6,069,151 A | 5/2000 | Dyke et al. |
| 7,482,456 B2 | 1/2009 | Dube et al. |
| 2001/0056122 A1 | 12/2001 | Nieman et al. |
| 2002/0103226 A1 | 8/2002 | Deschenes et al. |
| 2002/0143032 A1 | 10/2002 | Macdonald et al. |
| 2002/0183358 A1 | 12/2002 | Dyke et al. |
| 2004/0039784 A1 | 2/2004 | Jacobs et al. |
| 2004/0162314 A1 | 8/2004 | Dube et al. |
| 2004/0192783 A1 | 9/2004 | Morley |
| 2005/0234238 A1 | 10/2005 | Dube et al. |
| 2005/0245513 A1 | 11/2005 | Gallant et al. |
| 2006/0040981 A1 | 2/2006 | Dube et al. |
| 2006/0178416 A1 | 8/2006 | Barker et al. |
| 2006/0205806 A1 | 9/2006 | Kilian et al. |
| 2007/0049570 A1 | 3/2007 | Dean et al. |
| 2007/0065366 A1 | 3/2007 | Soliani Raschini et al. |
| 2007/0142373 A1 | 6/2007 | Baldwin et al. |
| 2007/0191426 A1 | 8/2007 | Edlin et al. |
| 2008/0027112 A1 | 1/2008 | Govek et al. |
| 2008/0096884 A1 | 4/2008 | Edlin et al. |
| 2009/0093029 A1 | 4/2009 | Usuda et al. |
| 2009/0312325 A1 | 12/2009 | Baldwin et al. |
| 2010/0004215 A1 | 1/2010 | Ray et al. |
| 2010/0261690 A1 | 10/2010 | Burkamp et al. |
| 2011/0275623 A1 | 11/2011 | Baker et al. |

FOREIGN PATENT DOCUMENTS

| | | |
|---|---|---|
| EP | 1894568 A1 | 3/2008 |
| WO | WO-97/18208 A1 | 5/1997 |
| WO | WO-98/57936 A1 | 12/1998 |
| WO | WO-01/94319 A1 | 12/2001 |
| WO | WO-2004024728 A2 | 3/2004 |
| WO | WO-2004/103998 A1 | 12/2004 |
| WO | WO-2006/023460 A2 | 3/2006 |
| WO | WO-2006/089689 A1 | 8/2006 |
| WO | WO-2007/107499 A1 | 9/2007 |
| WO | WO-2009/100169 A1 | 8/2009 |
| WO | WO-2009/142589 A1 | 11/2009 |
| WO | WO-2010/004517 A1 | 1/2010 |

OTHER PUBLICATIONS

Baker, J.G. (2005) *Brit. J. Pharmacol.*; 144:317-322.

(Continued)

*Primary Examiner* — Nizal Chandrakumar
(74) *Attorney, Agent, or Firm* — Gilead Sciences, Inc.

(57) ABSTRACT

This invention provides compounds of the formula:

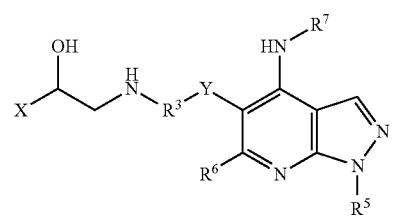

wherein X is

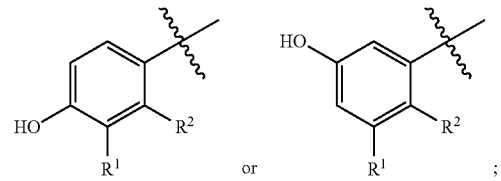

wherein $R^1$ and $R^2$ together with the phenyl to which they are bound may form a bicyclic, fused heterocyclic ring and all other variables are as defined herein, their use in pulmonary inflammation or bronchoconstriction therapy and compositions comprising and processes for preparing the same are provided.

18 Claims, No Drawings

OTHER PUBLICATIONS

Calverly et al., *Am. J. Respir. Crit. Care Med.* 2007; 176:154-61.
Calverly et al., *Lancet* 2009; 374:685-94.
Chong et al., *J. Pharmnacol. Toxicol. Methods* 1998;39:163-168.
Cockroft et al., (1976) Carbuterol : a double-blind clinical trial comparing carbuterol and salbutamol, *Current Therapeutic Research*, 19(2), 170-9.
Cynkowski, et al (1997) *Pharm Res* Supp 14(11) S524.
Dastidar et al., (2007) Therapeutic benefit of PDE4 Inhibitors in inflammatory diseases, *Curr Opin Investig Drugs*, 8(5):364-372.
Fabbri et al., *Lancet* 2009; 374:695-703.
Hamid & Tulic, *Annu. Rev. Physiol.* 2009; 71:489-507.
Hekking et al., (1990) Long-term efficacy of formoterol compared to salbutamol, *Lung*, 168 Suppl 76-82.
International Search Report—PCT/US2011/035738, dated Jun. 17, 2011.
International Search Report—PCT/US2011/035741, dated May 9, 2011.
Joseph et al., (2004) *Naun.-Sch. Arch. Pharm.*:369:525-532.
Kroegel & Foerster (2007) Phosphdiesterase-4 inhibitors as a novel approach for the treatment of respiratory disease: cilomilast, *Expert Opin. Investig. Drugs* 16(1):109-124.
Krymskaya, et al., (2007) Phosphodiesterases regulate airway smooth muscle function in health and disease, *Curr. Top. Dev. Biol.* 79:61-74.
Lofdahl et al., (1989) Formoterol fumarate, a new beta 2-adrenoceptor agonist, *Allergy*, 44(4), 264-71.
Lunniss et al., (2010) Addressing species specific metabolism and solubility issues in a quinoline series of oral PDE4 inhibitors, *Bioorganic & Medicinal Chemistry Letters*, 20(1), 137-140.
Lunniss, et al. (2009) Quinolines as a novel structural class of potent and selective PDE4 inhibitors: Optimisation for oral administration, *Bioorg & Med. Chem Letters* 19:1380-1385.
Molfino & Jeffery, Pulm. Pharmacol. Ther. 2007; 20:462-72.
Neale et al., (2010) Binding Mode Prediction of PDE4 Inhibitors: A Comparison of Modelling Methods, *Australian Journal of Chemistry*, 63(3), 396-404.
Parkkonen, et al., (2008) Phosphodiesterase 4 inhibitors delay human eosinophil and neutrophil apoptosis in the absence and presence of salbutamol, *Pulmonary Pharmacology & Therapeutics*, 21(3), 499-506.
Pennock et al., *J.Appl. Physiol.* 1979;46:399-406.
Rabe et al., *Lancet* 2005; 366:563-71.
Spina, *Brit. J. Pharmacol.* 2008;155:308-15.
Woodrow, et al., (2009) Quinolines as a novel structural class of potent and selective PDE4 inhibitors. Optimisation for inhaled administration, *Bioorg & Med. Chem Letters* 19:5261-5265.
Hughes, A. et al. (2011) *Bioorganic & Medicinal Chemistry Letters*, 21:1354-1358.
Jacobsen, J. et al. (2010) *Prog Respir. Res. Basel, Karger*, 39:39-45.
Jones, L. et al. (2011) *Bioorganic & Medicinal Chemistry Letters*, 21:2759-2763.
Knowles, R. et al. (2009) *Am J Respir Crit Car Med*, 179:A4581.
Nials, A. et al. (2011) *J Pharm. Exp. Ther., Fast Forward*, DOI:10.1124/jpet.110.173641.
Procopiou, P. et al. (2009) *J. Med. Chem.*, 52:2280-2288.
Ray, N. et al. (2009) *Expert Opin. Ther. Patents*, 19(1):1-12.
Traulau-Stewart, C. et al. (2011) *J Pharm. Exp. Ther., Fast Forward*, DOI:10.1124/jpet.110.173690.

BI-FUNCTIONAL PYRAZOLOPYRIDINE COMPOUNDS

FIELD OF THE INVENTION

The present invention relates to novel anti-inflammatory, bronchodilator compounds, compositions containing the same, therapeutic methods and uses for the same and processes for preparing the same.

BACKGROUND OF THE INVENTION

The chronic inflammatory processes underlie respiratory diseases such as Chronic Obstructive Pulmonary Disease (COPD) and asthma. These diseases involve active inflammation in the bronchial airways, parenchyma and pulmonary vasculature of the lungs. The inflammatory process in such diseases are characterized by increased numbers of activated immune cells such as macrophages, neutrophils, eosinophils and lymphocytes and the release of a range of pro-inflammatory signaling molecules, namely cytokines and chemokines from immune and resident lung cells. The pathogenesis of these diseases is different but chronic inflammation is an underlying driving mechanism to both. COPD is strongly associated with exposure to noxious particles and gases from the external environment such as cigarette smoking and exposure to wood burning fires and is characterized by oxidative stress and an imbalance of harmful tissue proteinases with anti-proteases. These processes can lead to distinctive pathologies such as goblet metaplasia and mucus hypersecretion which cause bronchitis, alveolar wall destruction leading to emphysema and inappropriate tissue repair and smooth muscle thickening causing small airways remodeling (reviewed by Molfino & Jeffery, *Pulm. Pharmacol. Ther.* 2007; 20:462-72). In asthma, allergic immune mechanisms underlie the chronic inflammatory processes which contributes to airway hyperresponsiveness and structural changes in the bronchial airway, termed remodeling, such as airway smooth muscle thickening and goblet cell hyperplasia. (reviewed by Hamid & Tulic, *Annu. Rev. Physiol.* 2009; 71:489-507).

Bronchodilator medications that can improve lung function and improve expiratory flow are used as a standard of care for symptom relief in the treatment of respiratory diseases. Inhaled long-acting $\beta_2$ adrenoceptor agonists (LABA) such as salmeterol or formoterol, or inhaled long-acting muscarinic receptor antagonists (LAMA) such as tiotropium are commonly prescribed to provide symptom relief.

Inflammation is a central process underlying many respiratory diseases and treatments that are anti-inflammatory may be efficacious and have the potential to impact disease progression. The phosphodiesterase-4 (PDE4) enzyme is a ubiquitously expressed enzyme that is responsible for catalyzing the hydrolysis of cyclic adenosine monophosphate (cAMP). Inhibition of the enzymatic activity of PDE4 with use of selective inhibitors elevates cellular levels of cAMP and this has anti-inflammatory effects in multiple immune and resident pulmonary cell types (Spina, *Brit. J. Pharmacol.* 2008; 155:308-15). Use of the oral PDE4 inhibitor roflumilast has demonstrated anti-inflammatory activity clinically showing a reduction of exacerbations and modest increases in lung function in COPD patients (Rabe et al., *Lancet* 2005; 366:563-71; Calverly et al., *Am. J. Respir. Crit. Care Med.* 2007; 176:154-61). Additionally, roflumilast improves lung function in severe and symptomatic patients with COPD treated with salmeterol or tiotropium but remains dose-limited due to side-effects including nausea, head-ache, diarrhea, and weight loss (Fabbri et al., *Lancet* 2009; 374:695-703; Calverly et al., *Lancet* 2009; 374:685-94). Forest Research Institute's product Daxas (roflumilast) has been approved as a once daily oral PDE4 inhibitor for the treatment of COPD. While it was accepted that Daxas demonstrated consistent evidence of efficacy concerns over a number of adverse event signals led the committee to deny approval based on the overall poor risk-to-benefit ratio. Topical delivery of a PDE4 inhibitor could therefore provide efficacious anti-inflammatory activity in the lungs whilst reducing the potential for side-effects by limiting it's exposure to the systemic circulation. Additionally, direct topical delivery may allow for higher local concentrations of the PDE4 inhibitor than could be achieved through oral dosing, and thus potential for further improvement in anti-inflammatory efficacy.

PCT Publication No. WO2005/090348 to GSK relates to compounds of formula (I) and pharmaceutically acceptable salts thereof as PDE4 Inhibitors:

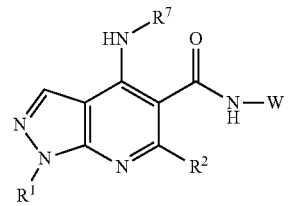

wherein (inter alia):

W is Ar, —$CR^4R^5$Ar or a group (y) or (y1) wherein:

Ar is

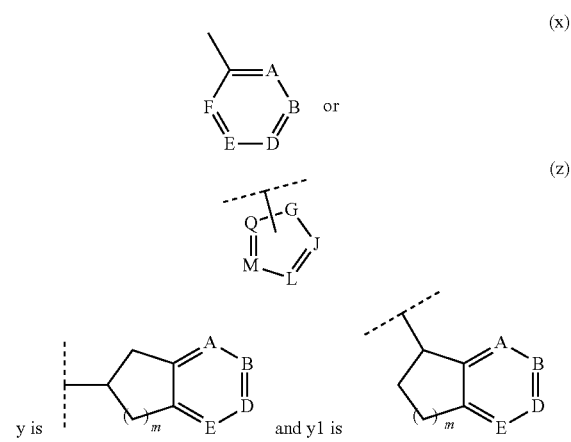

wherein A, B, D, E, and F are C—$R^6$, N or N+—O— and $R^6$ is inter alia H, halo, $C_{1-6}$alkyl, ... $R^7R^8N$—$S(O)_2$—, ... $R^7R^8N$—CO—, ... $R^7R^8N$—, ... —$CH_2$—$NR^7R^8$, —$CH_2$—$CH_2$—$NR^7R^8$, ... —$CH_2$—CO—$NR^7R^8$ and all other variables are as defined therein.

PCT Publication No. WO2007/023110 to Hoffmann-La Roche relates to P38 Map Kinase Inhibitors of formula Ia or Ib:

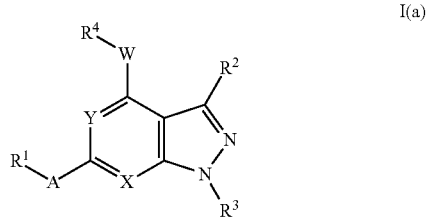

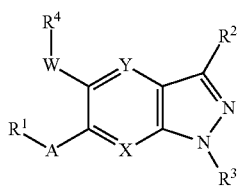

I(b)

wherein (inter alia):

R¹ is aryl or heteroaryl;

R⁴ is H, $C_{1-6}$alkyl, hydroxyl, amino, hetero-$C_{1-6}$alkyl, hetero-$C_{1-6}$alkoxy, hetero-$C_{1-6}$alkylamino, heterocyclyl, heterocyclyl-$C_{1-6}$alkyl, hydroxy$C_{3-6}$cycloalkyl, $C_{3-6}$cycloalkyl-$C_{1-6}$ alkyl, $C_{1-6}$alkylsulfonyl, $C_{1-6}$alkylsulfonamido, aryl, heteroaryl, aryl-$C_{1-6}$alkyl, heteroaryl-$C_{1-6}$alkyl, $C_{1-6}$alkoxy, heteroaryl-$C_{1-6}$alkoxy, —(CHR$^b$), C(=O)—R$^c$, —(CHR$^b$)$_r$—O—C(=O)—R$^c$, —(CHR$^b$)$_r$—NH—C(=O)—R$^c$ or —SO$_2$—R$^c$;

X and Y are N or one of X and Y is N and the other is CR$^d$;

W is a bond, O, S(O)$_m$, CH$_2$, or NR$^f$;

A is O, CH$_2$, S(O)$_m$, C(=O), NR$^h$, or CH(OR$^h$);

and all other variables are as defined therein.

PCT Publication No. WO2008/015416 to Glaxo Group Limited relates to PDE4 inhibitors of formula (I):

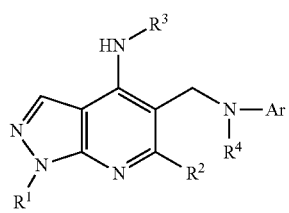

wherein Ar is

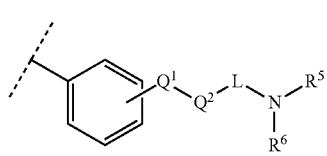

(x)

wherein:

Q¹ is NH or NMe and Q² is —C(O)—, —S(O)$_2$—, —C(O)NH or —C(O)NMe-, or

Q¹ is a bond or —O— and Q² is a bond, or

Q¹ is —C(O)— and Q² is —NH or NMe, or

Q¹ is —S(O)$_2$—, and Q² is —NH, NMe, or a bond;

L is (CH$_2$)$_n$ or —(CH$_2$)$_m$—O—(CH$_2$)$_m$—;

R⁵ is H, methyl, ethyl, n-propyl, isopropyl, —CH$_2$CH$_2$OH, —CH$_2$CH(Me)OH, —CH$_2$CH$_2$CH$_2$OH, —CH$_2$CH$_2$OMe, or —CH$_2$CH$_2$CH$_2$OMe; and R⁶ is $C_{1-4}$alkyl or $C_{1-4}$alkyl substituted by on OH or O$C_{1-3}$alkyl;

and all other variables are as defined therein.

PCT Publication No. 2008/015437 to Glaxo Group Limited relates to PDE4 inhibitors of formula (I):

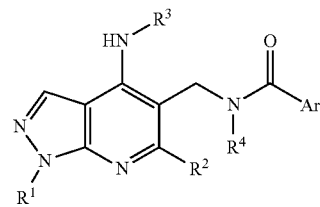

wherein:

Ar is (w)

(z1)

(y)

(z2)

wherein:

Q¹ is NH or NMe and Q² is —C(O)—, —S(O)$_2$—, —C(O)NH or —C(O)NMe-, or

Q¹ is a bond or —O— and Q² is a bond, or

Q¹ is —C(O)— and Q² is —NH or NMe, or

Q¹ is —S(O)$_2$—, and Q² is —NH, NMe, or a bond;

Q³ is a bond NH or NMe;

L is (CH$_2$)$_n$ or —(CH$_2$)$_m$—O—(CH$_2$)$_m$—;

R⁵ is H, methyl, ethyl, n-propyl, isopropyl, —CH$_2$CH$_2$OH, —CH$_2$CH(Me)OH, —CH$_2$CH$_2$CH$_2$OH, —CH$_2$CH$_2$OMe, or —CH$_2$CH$_2$CH$_2$OMe; and R⁶ is $C_{1-4}$alkyl or $C_{1-4}$alkyl substituted by on OH or O$C_{1-3}$alkyl;

and all other variables are as defined therein.

PCT Publication Nos. WO2009/100166, WO2009/100167, WO2009/100169 and WO2009/0197871, all to Glaxo Group Limited relate to dual pharmacophores-PDE4-Muscarinic antagonists of the following Formulas (I):

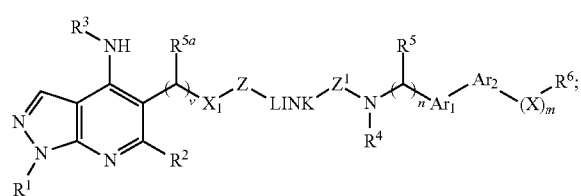

WO2009/100166

-continued

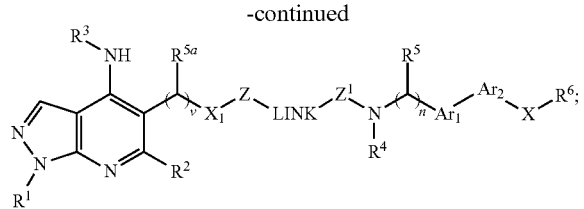

WO2009/100167

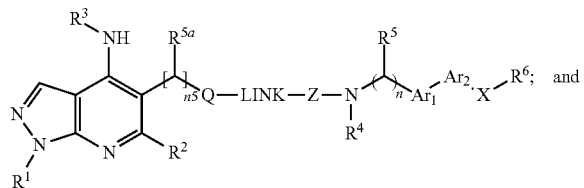

WO2009/100169

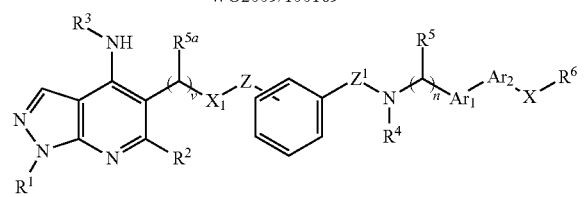

WO2009/197871 wherein all variables are as defined in each publication.

Conventional therapeutic agents for the treatment of inflammatory respiratory conditions suffer from limited efficacy and undesired side-effect profiles. Accordingly, there remains a need in the art for new drugs designed to treat respiratory conditions including inflammatory respiratory conditions such as asthma, COPD, chronic bronchitis, bronchiectasis, cystic fibrosis, etc.

SUMMARY OF THE INVENTION

As one aspect, the present invention provides compounds Formula I:

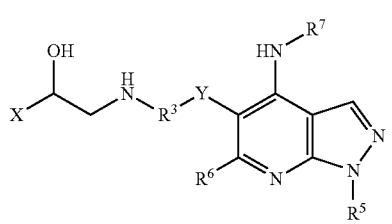

or a pharmaceutically acceptable salt thereof, wherein:
X is selected from:

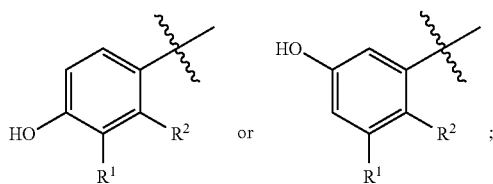

$R^1$ is $CH_2OH$, $CH_2CH_2OH$, $N(H)C(O)H$, $N(H)S(O_2)CH_3$, and $R^2$ is H;

or $R^1$ and $R^2$ together with the phenyl to which they are bound form a bicyclic, fused heterocyclic ring having 9 or 10 ring atoms wherein 1 or 2 ring atoms are selected from N, O and S and the remaining ring atoms are C, wherein said bicyclic fused heterocyclic ring is optionally substituted with one, two or three additional substituents independently selected from alkyl, oxo and OH;

$R^3$ is selected from $C_{4-12}$alkylene, $C_{4-12}$alkenylene, $C_{4-12}$alkynylene, $R^4$—O—$R^4$, $R^4$—N($R^8$)—$R^4$, $C_{3-6}$cycloalkylene, $R^4$—$C_{3-6}$cycloalkylene, $C_{3-6}$cycloalkylene-$R^4$, $R^4$—$C_{3-6}$cycloalkylene-$R^4$, $C_{6-10}$arylene, $R^4$—$C_{6-10}$arylene, $C_{6-10}$arylene-$R^4$, $R^4$—$C_{6-10}$arylene-$R^4$, $R^4$—$C_{6-10}$arylene-O—$R^4$, $R^4$—$C_{6-10}$arylene-N($R^8$)—$R^4$, $R^4$—$C_{6-10}$arylene-$C_{6-10}$arylene, Het, $R^4$-Het, $R^4$-Het-$C_{6-10}$arylene, Het-$R^4$, $R^4$-Het-$R^4$, $R^4$—O-Het $R^4$—$C_{6-10}$arylene-O-Het, $R^4$—$C_{6-10}$arylene-C(O)-Het, and $R^4$—$C_{6-10}$arylene-N($R^8$)-Het;

wherein said alkylene, alkenylene, alkynylene, cycloalkylene, or arylene is optionally substituted with 1, 2 or 3 substituents selected from halo, oxo, and $OR^8$;

Het is 5-6 membered saturated or unsaturated heterocyclene wherein 1 or 2 ring atoms are selected from N, O and S, and wherein said heterocyclene is optionally substituted with 1, 2 or 3 substituents selected from halo, alkyl, alkoxy, oxo and OH;

$R^4$ is $C_{1-10}$alkylene, $C_{2-10}$alkenylene, or $C_{2-10}$alkynylene wherein each $R^4$ is optionally substituted with 1, 2 or 3 substituents selected from halo, oxo, and $OR^8$; with the proviso that the total number of carbon atoms in the $C_{1-10}$alkylene, $C_{2-10}$alkenylene, or $C_{2-10}$alkynylene chains of two $R^4$ groups in any definition of $R^3$ is not greater than 12;

Y is C(O), C(O)N($R^8$)$CH_2$, N($R^8$)C(O), O—C(O)N($R^8$)$CH_2$, N($R^8$)C(O)N($R^8$)$CH_2$, or $SO_2$N($R^8$)$CH_2$;

$R^5$ is alkyl;

$R^6$ is H or alkyl;

$R^7$ is selected from unsubstituted $C_{3-6}$cycloalkyl, substituted $C_{3-6}$cycloalkyl, and a heterocyclic group selected from formulas (i), (ii), and (iii):

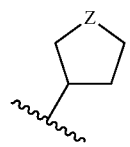 (i)

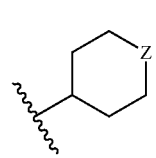 (ii)

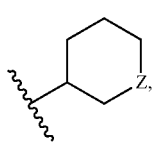 (iii)

wherein Z is O, S, S(O)$_2$, NH or N—$R^{7a}$, and
$R^{7a}$ is selected from alkyl, C(O)alkyl, C(O)$NH_2$, C(O)N(H)alkyl, and C(O)N(alkyl)$_2$; and
$R^8$ is H or alkyl.

In one embodiment, the present invention provides compounds of Formula I':

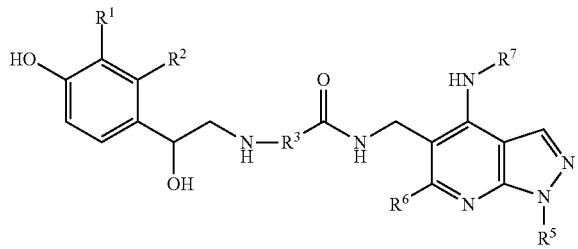

and pharmaceutically acceptable salts thereof, wherein all variables are as defined above.

As another aspect, the present invention provides a composition comprising a compound of Formula I or I' or a pharmaceutically acceptable salt thereof and a pharmaceutically acceptable carrier, diluent or excipient. In one embodiment, the composition is suitable for inhalation.

As another aspect, the present invention provides a method comprising administering to a human, an effective amount of a compound of Formula I or I' or a pharmaceutically acceptable salt thereof.

As another aspect, the present invention provides a method for treating pulmonary inflammation or bronchoconstriction in a human in need thereof. The method comprises administering to the human an effective amount of a compound of Formula I or I' or a pharmaceutically acceptable salt thereof.

As another aspect, the present invention provides a method for treating a disease associated with reversible or irreversible airway obstruction, chronic obstructive pulmonary disease (COPD), asthma, bronchiectasis (including bronchiectasis due to conditions other than cystic fibrosis), acute bronchitis, chronic bronchitis, post-viral cough, cystic fibrosis, emphysema, pneumonia, panbronchiolitis, transplant-associate bronchiolitis, sinusitis, and ventilator-associated tracheobronchitis or preventing ventilator-associated pneumonia, or treating sinusitis in a human in need thereof. The method comprises administering to the human an effective amount of a compound of Formula I or I' or a pharmaceutically acceptable salt thereof. In one embodiment, the present invention provides a method for treating chronic obstructive pulmonary disease (COPD) or asthma in a human in need thereof using a compound of Formula I or I' or a pharmaceutically acceptable salt thereof.

As another aspect, the present invention provides a compound of Formula I or I' or a pharmaceutically acceptable salt thereof for use as a medicament.

As another aspect, the present invention provides a compound of Formula I or I' or a pharmaceutically acceptable salt thereof for use in a method of treating of pulmonary inflammation or bronchoconstriction in a human.

As another aspect, the present invention provides a compound of Formula I or I' or a pharmaceutically acceptable salt thereof for use in a method of treating a disease associated with reversible or irreversible airway obstruction, chronic obstructive pulmonary disease (COPD), asthma, bronchiectasis (including bronchiectasis due to conditions other than cystic fibrosis), acute bronchitis, chronic bronchitis, post-viral cough, cystic fibrosis, emphysema, pneumonia, panbronchiolitis, transplant-associate bronchiolitis, sinusitis, and ventilator-associated tracheobronchitis or preventing ventilator-associated pneumonia, or treating sinusitis in a human. In one embodiment, the present invention provides a compound of Formula I or I' or a pharmaceutically acceptable salt thereof for use in a method of treating a disease associated with chronic obstructive pulmonary disease (COPD) or asthma, in a human.

As another aspect, the present invention provides the use of a compound of Formula I or I' or a pharmaceutically acceptable salt thereof for the manufacture of a medicament for the treatment of pulmonary inflammation or bronchoconstriction in a human.

As another aspect, the present invention provides the use of a compound of Formula I or I' or a pharmaceutically acceptable salt thereof for the manufacture of a medicament for the treatment of a disease associated with reversible or irreversible airway obstruction, chronic obstructive pulmonary disease (COPD), asthma, bronchiectasis (including bronchiectasis due to conditions other than cystic fibrosis), acute bronchitis, chronic bronchitis, post-viral cough, cystic fibrosis, emphysema, pneumonia, panbronchiolitis, transplant-associate bronchiolitis, sinusitis, and ventilator-associated tracheobronchitis or preventing ventilator-associated pneumonia, or treating sinusitis in a human.

As another aspect, the present invention provides a composition comprising a compound of Formula I or I' or a pharmaceutically acceptable salt thereof for use in the preparation of a medicament for the treatment of pulmonary inflammation or bronchoconstriction in a human.

As another aspect, the present invention provides a composition comprising a compound of Formula I or I' or a pharmaceutically acceptable salt thereof for use in the preparation of a medicament for the treatment of a disease associated with reversible or irreversible airway obstruction, chronic obstructive pulmonary disease (COPD), asthma, bronchiectasis (including bronchiectasis due to conditions other than cystic fibrosis), acute bronchitis, chronic bronchitis, post-viral cough, cystic fibrosis, emphysema, pneumonia, panbronchiolitis, transplant-associate bronchiolitis, sinusitis, and ventilator-associated tracheobronchitis or preventing ventilator-associated pneumonia, or treating sinusitis in a human.

DETAILED DESCRIPTION OF THE INVENTION

One aspect provided are compounds Formula I:

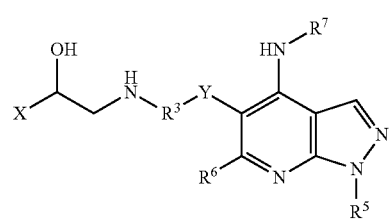

or a pharmaceutically acceptable salt thereof,
wherein:
X is selected from:

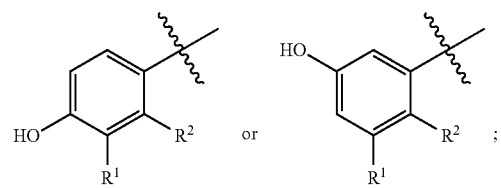

$R^1$ is $CH_2OH$, $CH_2CH_2OH$, $N(H)C(O)H$, $N(H)S(O_2)CH_3$, and $R^2$ is H;
or $R^1$ and $R^2$ together with the phenyl to which they are bound form a bicyclic, fused heterocyclic ring having 9 or 10 ring atoms wherein 1 or 2 ring atoms are selected from N, O and S and the remaining ring atoms are C, wherein said bicyclic fused heterocyclic ring is optionally substituted with one, two or three additional substituents independently selected from alkyl, oxo and OH;

$R^3$ is selected from $C_{4-12}$alkylene, $C_{4-12}$alkenylene, $C_{4-12}$alkynylene, $R^4$—O—$R^4$, $R^4$—N($R^8$)—$R^4$, $C_{3-6}$cycloalkylene, $R^4$—$C_{3-6}$cycloalkylene, $C_{3-6}$cycloalkylene-$R^4$, $R^4$—$C_{3-6}$cycloalkylene-$R^4$, phenylene, $R^4$-phenylene, phenylene-$R^4$, $R^4$-phenylene-$R^4$, $R^4$-phenylene-O—$R^4$, $R^4$-phenylene-N($R^8$)—$R^4$, $R^4$-phenylene-phenylene, Het, $R^4$-Het, $R^4$-Het-phenylene, Het-$R^4$, $R^4$-Het-$R^4$, $R^4$—O-Het $R^4$-phenylene-O-Het, $R^4$-phenylene-C(O)-Het, and $R^4$-phenylene-N($R^8$)-Het, wherein said alkylene, alkenylene, alkynylene, cycloalkylene, or arylene is optionally substituted with 1, 2 or 3 substituents selected from halo, oxo, and O$R^8$;

Het is 5-6 membered saturated or unsaturated heterocyclene wherein 1 or 2 ring atoms are selected from N, O and S, and wherein said heterocyclene is optionally substituted with 1, 2 or 3 substituents selected from halo, alkyl, alkoxy, oxo and OH;

$R^4$ is $C_{1-10}$alkylene, $C_{2-10}$alkenylene, or $C_{2-10}$alkynylene wherein each $R^4$ is optionally substituted with 1, 2 or 3 substituents selected from halo, oxo, and O$R^8$; with the proviso that the total number of carbon atoms in the $C_{1-10}$alkylene, $C_{2-10}$alkenylene, or $C_{2-10}$alkynylene chains of two $R^4$ groups in any definition of $R^3$ is not greater than 12;

Y is C(O), C(O)N($R^8$)CH$_2$, N($R^8$)C(O), O—C(O)N($R^8$)CH$_2$, N($R^8$)C(O)N($R^8$)CH$_2$, or SO$_2$N($R^8$)CH$_2$;

$R^5$ is alkyl;

$R^6$ is H or alkyl;

$R^7$ is selected from unsubstituted $C_{3-6}$cycloalkyl, substituted $C_{3-6}$cycloalkyl, and a heterocyclic group selected from formulas (i), (ii), and (iii):

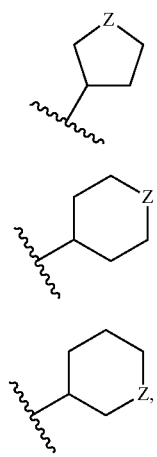

(i)

(ii)

(iii)

wherein Z is O, S, S(O)$_2$, NH or N—$R^{7a}$, and $R^{7a}$ is selected from alkyl, C(O)alkyl, C(O)NH$_2$, C(O)N(H)alkyl, and C(O)N(alkyl)$_2$, and $R^8$ is H or alkyl.

Also provided within the descriptions of each group of compounds herein, and the pharmaceutically acceptable salts thereof, is another set of embodiments wherein $R^1$ and $R^2$ together with the phenyl to which they are bound form a bicyclic, fused heterocyclic ring selected from;

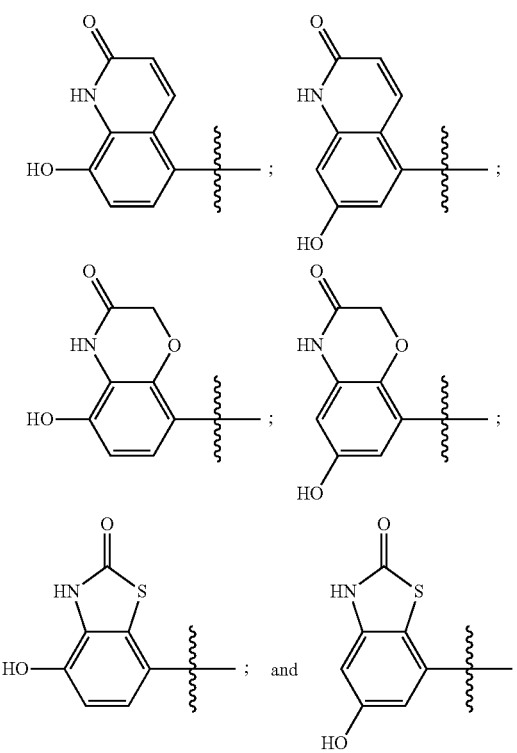

Other embodiments provide compounds of the Formula II(a) and Formula II(b):

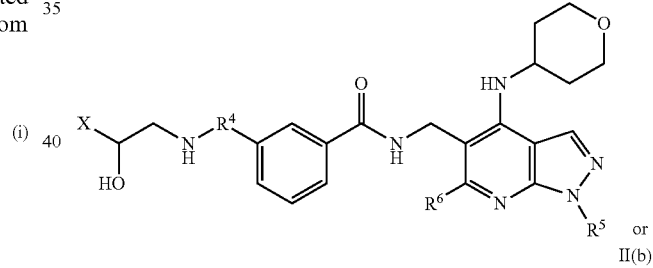

II(a)

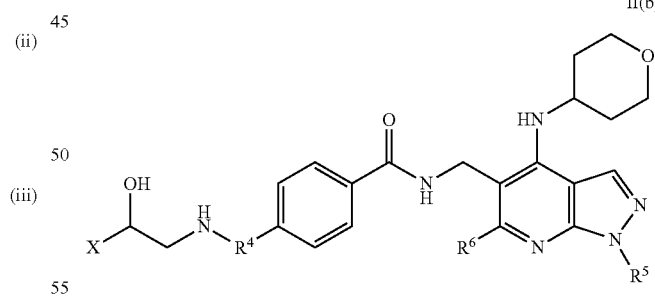

II(b)

X is selected from:

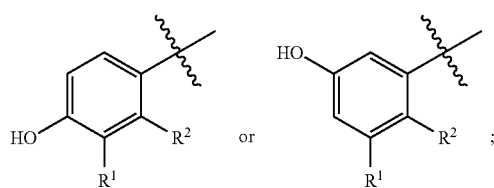

$R^1$ is —CH$_2$—OH, —NH—CHO, or —NH—SO$_2$—C$_1$-C$_3$ alkyl, and $R^2$ is H; or $R^1$ and $R^2$ together with the phenyl ring to which they are bound for a bicyclic, fused heterocyclic ring of the formula:

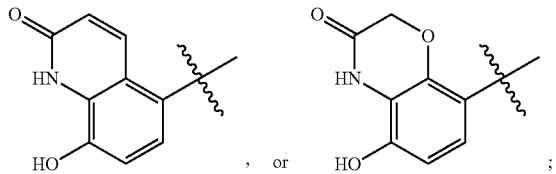 [SMILES: *c1ccc(O)c2[nH]c(=O)ccc12 ; "," ; "or" ; *c1ccc(O)c2c1OCC(=O)N2 ; ";"]

, or    ;

$R^4$ is C$_{1-10}$ alkylene, C$_{2-10}$ alkenylene, or C$_{2-10}$ alkynylene, wherein each $R^4$ is optionally substituted with 1, 2 or 3 substituents selected from halo, oxo, and OR$^B$;

$R^5$ is alkyl;

$R^6$ is H or alkyl, and $R^8$ is H or alkyl; or a pharmaceutically acceptable salt thereof.

Another embodiment provides compounds of the formula:

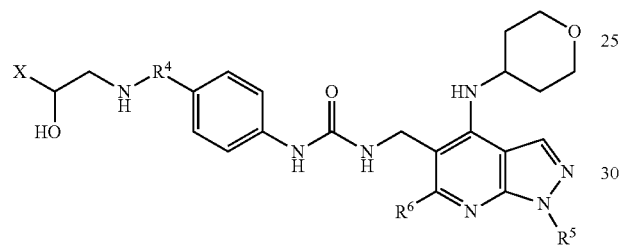

wherein

X is selected from:

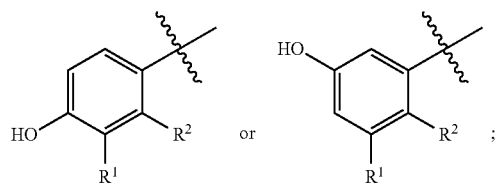

or    ;

$R^1$ is —CH$_2$—OH, —NH—CHO, or —NH—SO$_2$—C$_1$-C$_3$ alkyl, and $R^2$ is H; or $R^1$ and $R^2$ together with the phenyl ring to which they are bound for a bicyclic, fused heterocyclic ring of the formula:

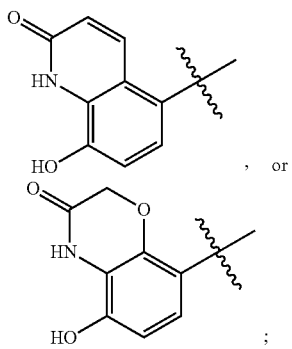

, or

;

$R^4$ is C$_{1-10}$ alkylene, C$_{2-10}$ alkenylene, or C$_{2-10}$ alkynylene, wherein each $R^4$ is optionally substituted with 1, 2 or 3 substituents selected from halo, oxo, and OR$^8$;

$R^5$ is alkyl;

$R^6$ is H or alkyl, and $R^8$ is H or alkyl; or a pharmaceutically acceptable salt thereof.

Additional embodiments are provided by compounds of Formulas IV, V, VI, VII, and VII:

IV

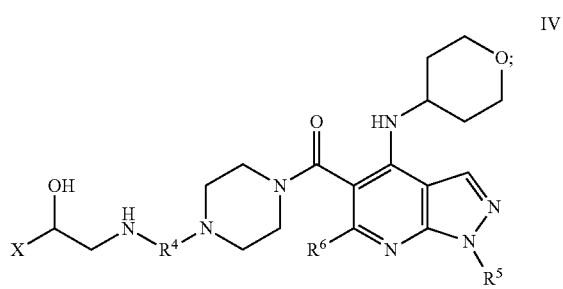

V

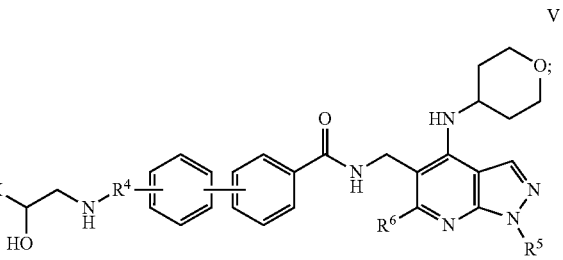

VII

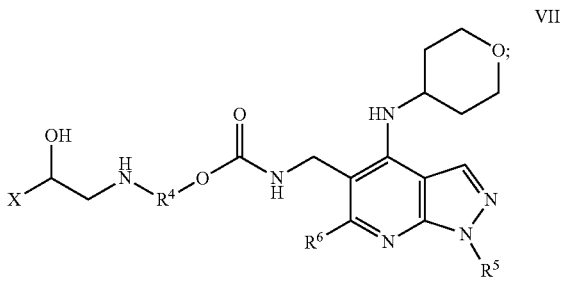

VIII

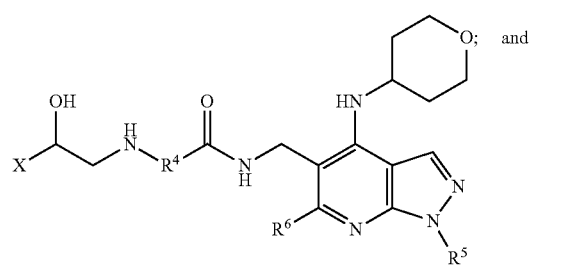

and

IX

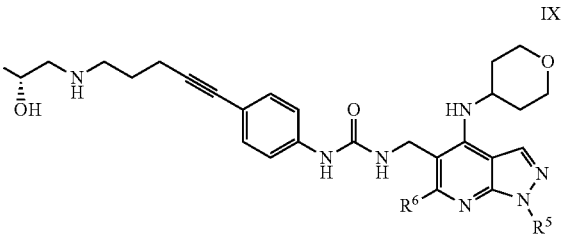

wherein, in the compounds of each embodiment,

X is a substituted phenyl ring selected from:

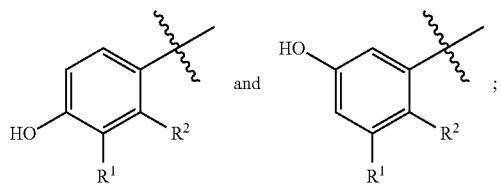

and;

$R^1$ is —$CH_2$—OH, —NH—CHO, or —NH—$SO_2$—$CH_3$, and $R^2$ is H; or $R^1$ and $R^2$ together with the phenyl ring to which they are bound for a bicyclic, fused heterocyclic ring of the formula:

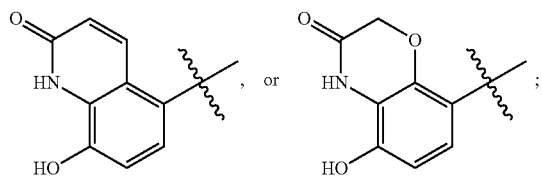 [SMILES: *c1ccc(O)c2[nH]c(=O)ccc12 ; *c1ccc(O)c2c1OCC(=O)N2]

, or ;

$R^4$ is $C_{1-10}$ alkylene, $C_{2-10}$ alkenylene, or $C_{2-10}$ alkynylene, wherein each $R^4$ is optionally substituted with 1, 2 or 3 substituents selected from halo, oxo, and $OR^8$;
$R^5$ is alkyl;
$R^6$ is H or alkyl, and
$R^8$ is H or alkyl; or a pharmaceutically acceptable salt thereof.

Within each group of compounds described herein, or the pharmaceutically acceptable salts thereof, there is also a further embodiment wherein the moiety indicated by the formula:

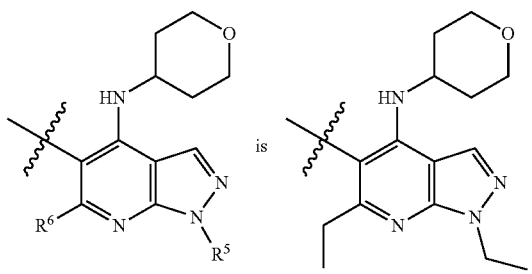

is .

A single molecule for inhaled use which has bifunctional activity as both a long-acting $\beta_2$ adrenoceptor agonist and a PDE4 inhibitor could provide both symptom control through bronchodilation and anti-inflammatory activity. Such compound would also have the potential to provide additive or synergistic anti-inflammatory activity through the complementary interaction of both molecular signaling pathways. Beta agonists when binding to a receptor through the action of G proteins will increase adenylate cyclase activity which causes elevation of cellular cyclic AMP. Inhibition of the PDE4 enzyme also serves to maintain cellular cAMP levels through inhibition of the enzyme responsible for its breakdown. An inhaled molecule that has both $\beta_2$ agonist and PDE4 inhibitory activity may provide additive effects and potentially synergistic anti-inflammatory activity, and thus could be dose-sparing. Deposition of a single bi-functional compound in the lung microenvironment should also maximize the opportunity for this molecular interaction to occur compared to a mixture of the single agents dosed together. High lung to systemic exposure levels through topical delivery allied with long lung retention times will dramatically reduce the opportunity for side-effects mediated through exposure via the systemic circulation to other tissues and organs.

As used herein, the following terms are defined as indicated.

"A compound of the invention" means a compound of Formula I or a salt, particularly a pharmaceutically acceptable salt thereof.

"A compound of Formula I" means a compound having the structural formula designated herein as Formula I or I' (as compounds of Formula I' are a subset of compounds of Formula I). Compounds of Formula I include solvates and hydrates (i.e., adducts of a compound of Formula I with a solvent). In those embodiments wherein a compound of Formula I includes one or more chiral centers, the phrase is intended to encompass racemic mixtures, each individual stereoisomer including optical isomers (enantiomers and diastereomers) and geometric isomers (cis-/trans-isomerism) and mixtures of stereoisomers. In addition, compounds of Formula I also include tautomers of the depicted formula (s).

"Alkyl" is a linear or branched hydrocarbon chain of 1 to 8 carbon atoms (i.e., $C_{1-8}$ alkyl), or typically, 1 to 6 carbon atoms (i.e., $C_{1-6}$ alkyl), unless the number of carbon atoms is otherwise specified. When the compound of Formula I includes more than one alkyl, the alkyls may be the same or different. Examples of suitable alkyl groups include, but are not limited to, methyl ("Me"), ethyl ("Et"), 1-propyl (n-propyl), isopropyl, n-butyl, isobutyl (2-methyl-1-propyl), sec-butyl (2-butyl), tert-butyl (—$C(CH_3)_3$), n-pentyl, 2-pentyl, 3-pentyl, hexyl, octyl, and the like.

"Alkenyl" is a linear or branched hydrocarbon chain with at least one site of unsaturation, i.e. a carbon-carbon double bond, and having from 2 to 8 carbon atoms (i.e., $C_{2-8}$ alkenyl), or typically, 2 to 6 carbon atoms (La, $C_{2-6}$ alkenyl) unless the number of carbon atoms is otherwise specified. When the compound of Formula I includes more than one alkenyl, the alkenyls may be the same or different. Examples of suitable alkenyl groups include, but are not limited to, ethylene or vinyl (—CH=$CH_2$), allyl (—$CH_2$CH=$CH_2$), 5-hexenyl (—$CH_2CH_2CH_2CH_2$CH=$CH_2$), and the like.

"Alkynyl" is a linear or branched hydrocarbon chain having at least one carbon-carbon triple bond, and optionally also one or more carbon-carbon double bonds, and having from 2 to 8 carbon atoms (i.e., $C_{2-8}$ alkynyl), or more typically 2 to 6 carbon atoms (i.e., $C_{2-6}$ alkynyl) unless the number of carbon atoms is otherwise specified. When the compound of Formula I includes more than one alkynyl, the alkynyls may be the same or different. Examples of suitable alkynyl groups include, but are not limited to, acetylenyl propargyl (—$CH_2$C≡CH), and the like.

"Alkylene" refers to a saturated, linear or branched divalent hydrocarbon radical having from 1 to 12 carbon atoms ("$C_{1-12}$ alkylene"), unless the number of carbon atoms is otherwise specified. When the compound of Formula I includes more than one alkylene, the alkylenes may be the same or different. Typical alkylene radicals include, but are not limited to, methylene (—$CH_2$—), ethylene (—CH($CH_3$)— or —$CH_2CH_2$—), propylene (e.g., —CH($CH_2CH_3$)—, —$CH_2$CH($CH_3$)— or —$CH_2CH_2CH_2$—), butylene (e.g., —$CH_2CH_2CH_2CH_2$—, —$C(CH_3)_2CH_2$—), and the like. In one embodiment, alkylene is linear. In one embodiment, alkylene is branched.

"Alkenylene" refers to an unsaturated, linear or branched divalent hydrocarbon radical having at least one carbon-carbon double bond, and having from 2 to 12 carbon atoms ("C$_{2-12}$ alkenylene"), unless the number of carbon atoms is otherwise specified. When the compound of Formula I includes more than one alkenylene the alkenylenes may be the same or different. Typical alkenylene radicals include, but are not limited to, 1,2-ethylene (—CH═CH—) and (—CH$_2$CH═CHCH$_2$CH$_2$—). In one embodiment, alkenylene is linear.

"Alkynylene" refers to an unsaturated, linear or branched divalent hydrocarbon radical having at least one carbon-carbon triple bond and optionally also one or more carbon-carbon double bonds, and having 2 to 12 carbon atoms ("C$_{2-12}$ alkenylene"), unless the number of carbon atoms is otherwise specified. When the compound of Formula I includes more than one alkenylene the alkenylenes may be the same or different. Typical alkynylene radicals include, but are not limited to, 1,2-ethynylene (—C≡C—) and (—CH$_2$C≡CCH$_2$CH$_2$—). In one embodiment, alkynylene is linear.

"Alkoxy" refers to O-alkyl, wherein "alkyl" is as defined above.

"Halo" or "halogen" are synonymous and refer to fluoro, chloro, bromo, and iodo. In one embodiment, halo is fluoro, chloro or bromo.

"Haloalkyl" is linear or branched hydrocarbon chain of 1 to 8 carbon atoms (i.e., C$_{1-8}$haloalkyl), or typically, 1 to 6 carbon atoms (i.e., C$_{1-6}$haloalkyl), unless the number of carbon atoms is otherwise specified, substituted by one or more halogens, fluoro, chloro, bromo and iodo. Haloalkyl include perhaloalkyls such as trifluoromethyl. When the compound of Formula I includes more than one haloalkyl, the haloalkyls may be the same or different. Examples of suitable haloalkyl groups include, but are not limited to, fluoromethyl, chloromethyl, trifluoromethyl, dichloromethyl, dichloroethyl, and the like.

"Oxo" as used herein refers to the group ═O attached directly to a carbon atom of a hydrocarbon ring or a C, N or S of a heterocyclic ring to result in oxides, —N-oxides, sulfones and sulfoxides.

"Cycloalkyl" refers to a monocyclic, saturated or partially unsaturated, non-aromatic ring having from 3 to 6 carbon atoms, (C$_{3-6}$cycloalkyl) unless a different number of carbon atoms is specified. Examples of specific cycloalkyl groups include cyclopropyl, cyclobutyl, cyclopentyl, and cyclohexyl. Cycloalkyl also includes cycloalkyl groups optionally substituted with 1 or 2 substituents, which substituents are the same or different and are selected from halo, alkyl, hydroxyl, O-alkyl, oxo, amino (e.g., NH$_2$), alkylamino (e.g., N(H)alkyl), dialkylamino (e.g., N(alkyl)$_2$), C(O)NH$_2$, C(O)N(H)alkyl, and C(O)N(alkyl)$_2$, or any subset thereof.

"Cycloalkylene" refers to a divalent, monocyclic, saturated or partially unsaturated, non-aromatic ring having from 3 to 6 carbon atoms, (C$_{3-6}$cycloalkylene) unless a different number of carbon atoms is specified. When the compound of Formula I includes more than one cycloalkylene, the cycloalkylene groups may be the same or different. Examples of specific cycloalkylene groups include cyclopropylene, cyclobutylene, cyclopentylene, and cyclohexylene. Cycloalkylene also includes cycloalkyl groups optionally substituted with 1 or 2 substituents, which substituents are the same or different and are selected from halo, alkyl, hydroxyl, O-alkyl, oxo, amino (e.g., NH$_2$), alkylamino (e.g., N(H)alkyl), and dialkylamino (e.g., N(alkyl)$_2$), or any subset thereof. In one embodiment, the cycloalkylene is unsubstituted.

"Arylene" refers to a divalent, monocyclic or fused bicyclic, aromatic ring having from 6 to 10 carbon atoms, (C$_{6-10}$arylene) unless a different number of carbon atoms is specified. When the compound of Formula I includes more than one arylene, the arylene groups may be the same or different. Examples of specific arylene groups include phenylene and naphthylene. Arylene also includes arylene groups optionally substituted with 1 or 2 substituents, which substituents are the same or different and are selected from halo, alkyl, hydroxyl, O-alkyl, amino (e.g., NH$_2$), alkylamino (e.g., N(H)alkyl), and dialkylamino (e.g., N(alkyl)$_2$), or any subset thereof. In one embodiment, arylene is phenylene. In one embodiment, arylene is unsubstituted phenylene.

"Heterocyclic group" or "heterocycle" are synonymous and refer to monocyclic and fused bicyclic, saturated or partially unsaturated, or aromatic rings having 5, 6, 9 or 10 ring atoms wherein 1, 2, 3, or 4 ring atoms is/are a heteroatom independently selected from N, O and S and all remaining ring atoms are C. In one embodiment, the heterocyclic group has 5, 6, 9 or 10 rings atoms wherein 1, 2 or 3 ring atoms is/are a heteroatom independently selected from N, O and S. In all embodiments wherein the heterocyclic group includes 2 or more heteroatoms (N, O and S) the heteroatoms may be the same or different. In all embodiments wherein the compound of Formula I includes 2 or more heterocyclic groups, the heterocyclic groups may be the same or different. Examples of heterocyclic groups include but are not limited to furanyl, tetrahydrofuranyl, thiophenyl, tetrahydrothiophenyl, sulfur oxidized tetrahydrothiophenyl, pyrrolyl, pyrrolinyl, pyrrolidinyl, dioxolanyl, oxazolidinyl, oxazolyl, isoxazolyl, thiazolyl, isothiazolyl, imidazolyl, imidazolinyl, imidazolidinyl, pyrazolyl, pyrazolinyl, pyrazolidinyl, triazolyl, tetrazolyl, pyranyl, dihydropyranyl, tetrahydropyranyl, pyridyl, dihydropyridyl, piperidyl, dioxanyl, morpholinyl, dithianyl, thiomorpholinyl, pyridazinyl, pyrimidinyl, pyrazinyl, piperazinyl, triazinyl, indolizinyl, indolyl, isoindolyl, oxindolyl, indolinyl, benzofuranyl, dihydrobenzofuranyl, isobenzofuranyl, benzothienyl, indazolyl, benzimidazolyl, benzoxazolinyl, benzoxazolyl, benzisoxazolyl, benzthiazolyl, benzotriazolyl, benzopyranyl, purinyl, quinolizinyl, quinolinyl, isoquinolinyl, tetrahydroquinolinyl, tetrahydroisoquinolinyl, decahydroquinolinyl, octahydroisoquinolinyl, cinnolinyl, phthalazinyl, quinazolinyl, quinoxalinyl, naphthyridinyl, pteridinyl, thianaphthalenyl and the like. Heterocyclic groups may be bound through any available ring carbon or ring heteroatom, such as N.

"Heterocyclene" refers to a bivalent heterocyclic group as defined herein. For example, heterocyclenes include:

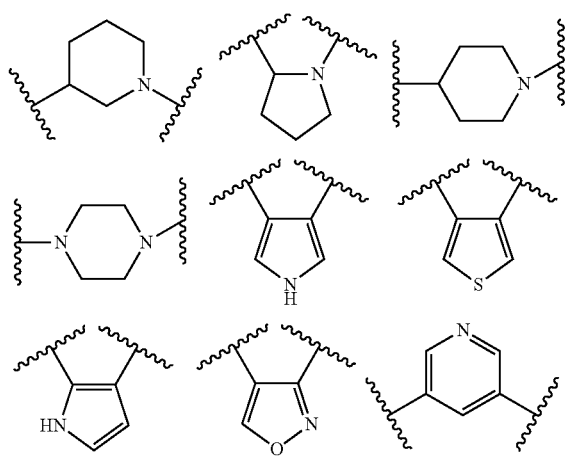

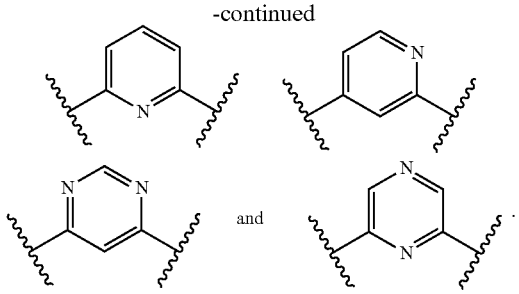

Preferably, the heterocyclene groups in the compounds of Formula I are monocyclic, saturated or partially unsaturated rings having 5 or 6 ring atoms wherein 1, 2, or 3 ring atoms is/are a heteroatom independently selected from N, O and S and all remaining ring atoms are C.

The term "optionally substituted" in reference to a particular moiety of the compound of Formula I (e.g., an optionally substituted alkylene) refers to that moiety having no substituents, and that moiety having the specified number of substituents; typically up to 4 substituents unless otherwise indicated. Unless otherwise indicated, when the term "substituted" is used in conjunction with groups which have multiple available sites for substitution or two or more moieties capable of substitution, the substituents can be attached to any available C or heteroatom.

Throughout the description and examples, compounds are named using standard IUPAC naming principles where possible.

In some chemical structure representations where carbon atoms do not have a sufficient number of attached variables or bonds depicted to produce a valence of four, the remaining carbon substituents needed to provide a valence of four are understood to be hydrogen. Similarly, in some chemical structures where a bond is drawn without specifying the terminal group, such bond is indicative of a methyl (Me, —CH$_3$) group, as is conventional in the art.

In one aspect, the invention comprises compounds of Formula I:

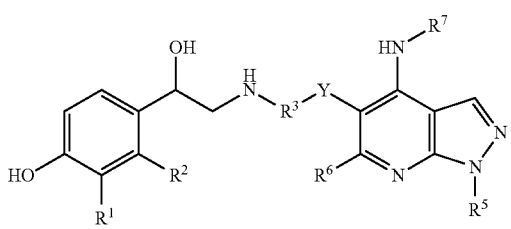

or a pharmaceutically acceptable salt thereof,
wherein:
$R^1$ is CH$_2$OH, CH$_2$CH$_2$OH, N(H)C(O)H, N(H)S(O$_2$)CH$_3$, and $R^2$ is H;
or $R^1$ and $R^2$ together with the phenyl to which they are bound form a bicyclic, fused heterocyclic ring having 9 or 10 ring atoms wherein 1 or 2 ring atoms are selected from N, O and S and the remaining ring atoms are C, wherein said bicyclic fused heterocyclic ring is optionally substituted with one, two or three additional substituents independently selected from alkyl, oxo and OH;
$R^3$ is selected from C$_{4-12}$alkylene, C$_{4-12}$alkenylene, C$_{4-12}$alkynylene, R$^4$—O—R$^4$, R$^4$—N(R$^8$)—R$^4$, C$_{3-6}$cycloalkylene, R$^4$—C$_{3-6}$cycloalkylene, C$_{3-6}$cycloalkylene-R$^4$, R$^4$—C$_{3-6}$cycloalkylene-R$^4$, C$_{6-10}$arylene, R$^4$—C$_{6-10}$arylene, C$_{6-10}$arylene-R$^4$, R$^4$—C$_{6-10}$arylene-R$^4$, R$^4$—C$_{6-10}$arylene-O—R$^4$, R$^4$—C$_{6-10}$arylene-N(R$^8$)—R$^4$, R$^4$—C$_{6-10}$arylene-C$_{6-10}$arylene, Het, R$^4$-Het, Het-R$^4$, R$^4$-Het-R$^4$, R$^4$—O-Het R$^4$—C$_{6-10}$arylene-O-Het, R$^4$—C$_{6-10}$arylene-C(O)-Het, and R$^4$—C$_{6-10}$arylene-N(R$^8$)-Het,
wherein said alkylene, alkynylene, alkynylene, cycloalkylene, or arylene is optionally substituted with 1, 2 or 3 substituents selected from halo, oxo, and OR$^8$;
Het is 5-6 membered saturated or unsaturated heterocyclene wherein 1 or 2 ring atoms are selected from N, O and S, and wherein said heterocyclene is optionally substituted with 1, 2 or 3 substituents selected from halo, alkyl, alkoxy, oxo and OH;
$R^4$ is C$_{1-10}$alkylene, C$_{2-10}$alkenylene, or C$_{2-10}$alkynylene wherein each R$^4$ is optionally substituted with 1, 2 or 3 substituents selected from halo, oxo, and OR$^8$; with the proviso that the total number of carbon atoms in the C$_{1-10}$alkylene, C$_{2-10}$alkenylene, or C$_{2-10}$alkynylene chains of two R$^4$ groups in any definition of R$^3$ is not greater than 12; Y is C(O), C(O)N(R$^8$)CH$_2$, N(R$^8$)C(O), O—C(O)N(R$^8$)CH$_2$, N(R$^8$)C(O)N(R$^8$)CH$_2$, or SO$_2$N(R$^8$)CH$_2$;
$R^5$ is alkyl;
$R^6$ is H or alkyl;
$R^7$ is selected from unsubstituted C$_{3-6}$cycloalkyl, substituted C$_{3-6}$cycloalkyl, and a heterocyclic group selected from formulas (i), (ii), and (iii):

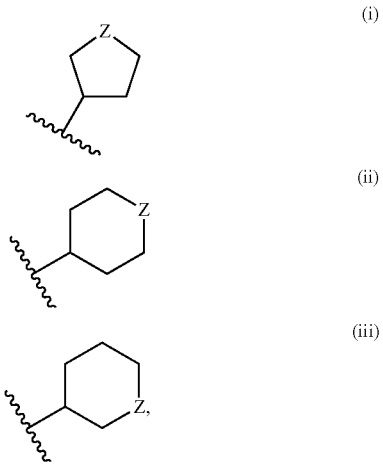

wherein Z is O, S, S(O)$_2$, NH or N—R$^{7a}$, and
$R^{7a}$ is selected from alkyl, C(O)alkyl, C(O)NH$_2$, C(O)N(H)alkyl, and C(O)N(alkyl)$_2$; and
$R^8$ is H or alkyl.

In one embodiment, the compounds of the invention are defined wherein $R^1$ is CH$_2$OH, N(H)C(O)H, or N(H)S(O$_2$)CH$_3$, and $R^2$ is H. In one particular embodiment the compounds of the invention are defined wherein $R^1$ is CH$_2$OH and $R^2$ is H.

In one embodiment, the compounds of the invention are defined wherein $R^1$ and $R^2$ together with the phenyl to which they are bound form a bicyclic, fused heterocyclic ring having 9 or 10 ring atoms wherein 1 or 2 ring atoms are selected from N, O and S, and the bicyclic fused heterocyclic ring is optionally substituted with one, two or three additional substituents independently selected from alkyl, oxo and OH. The phrase "one, two or three additional substituents" refers to one, two or three substituents in addition to the —OH indicated in Formula I as being bound to the same phenyl ring as $R^1$ and $R^2$. In one embodiment, wherein $R^1$ and $R^2$ together with the phenyl to which they are bound form a bicyclic, fused heterocyclic ring having 9 or 10 ring atoms wherein 1 or 2 ring atoms are selected from N, O and S, and the bicyclic fused heterocyclic ring is optionally substituted with one additional substituent selected from alkyl, oxo and OH. In one such embodiment, the compounds of the invention are defined wherein $R^1$ and $R^2$ together with the phenyl to which they are bound form

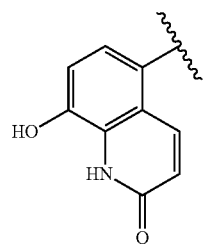

In one embodiment, the compounds of the invention are defined wherein $R^3$ is selected from $C_{4-12}$alkylene, $C_{4-12}$alkenylene, $C_{4-12}$alkynylene, $R^4$—O—$R^4$, and $R^4$—N($R^8$)—$R^4$, wherein said alkylene, alkenylene or alkynylene are each optionally substituted with 1, 2 or 3 substituents selected from halo, oxo, and $OR^8$. The alkylene, alkenylene or alkynylene groups of $R^3$ may be linear or branched. In one embodiment $R^3$ is selected from $C_{5-8}$alkylene, $C_{5-8}$alkenylene, $C_{5-8}$alkynylene, $R^4$—O—$R^4$, and $R^4$—N($R^8$)—$R^4$, wherein each $R^4$ is $C_{1-4}$alkylene, $C_{2-4}$alkenylene, or $C_{2-4}$alkynylene each alkylene, alkenylene and alkynylene being linear or branched and optionally substituted with 1 or 2 substituents selected from halo, oxo, and $OR^8$. As noted above, there is a proviso that the total number of carbon atoms in the $C_{1-10}$alkylene, $C_{2-10}$alkenylene, or $C_{2-10}$alkynylene chains of two $R^4$ groups in any definition of $R^3$ is not greater than 12. For instance, when $R^3$ is —$R^4$—O—$R^4$—, if the first $R^4$ group is an ethylene (—CH2-CH2-) chain, the maximum number of carbon atoms in the second $R^4$ group in that $R^3$ member would be ten.

The alkylene, alkenylene or alkynylene groups of $R^4$ may also be linear or branched. In one embodiment $R^3$ is defined such that each alkylene, alkenylene and alkynylene and each group $R^4$ is linear or branched, but unsubstituted by halo, oxo, and $OR^8$. In one particular embodiment $R^3$ is unsubstituted, linear or branched $C_{5-8}$alkylene. In one preferred embodiment $R^3$ is unsubstituted, linear $C_5$alkylene. In one preferred embodiment $R^3$ is unsubstituted, linear $C_6$alkylene. In one preferred embodiment $R^3$ is unsubstituted, linear $C_7$alkylene. In one particular embodiment $R^3$ is unsubstituted, linear $C_5$alkynylene.

In one embodiment, the compounds of the invention are defined wherein $R^3$ is selected from $C_{3-6}$cycloalkylene, $R^4$—$C_{3-6}$cycloalkylene, $C_{3-6}$cycloalkylene-$R^4$, $R^4$—$C_{3-6}$cycloalkylene-$R^4$, $C_{6-10}$arylene, $R^4$—$C_{6-10}$arylene, $C_{6-10}$arylene-$R^4$, $R^4$—$C_{6-10}$arylene-$R^4$, $R^4$—$C_{8-10}$arylene-O—$R^4$, $R^4$—$C_{6-10}$arylene-N($R^8$)—$R^4$, $R^4$—$C_{6-10}$arylene-$C_{6-10}$arylene, Het, $R^4$-Het, Het-$R^4$, $R^4$-Het-$R^4$, $R^4$—O-Het $R^4$—$C_{6-10}$arylene-O-Het, $R^4$—$C_{6-10}$arylene-C(O)-Het, and $R^4$—$C_{6-10}$arylene-N($R^8$)-Het. In one particular embodiment, $R^3$ is selected from $C_{6-10}$arylene, $R^4$—$C_{6-10}$arylene, $R^4$—$C_{6-10}$arylene-$R^4$, Het, $R^4$-Het, and $R^4$-Het-$R^4$. In one particular embodiment, $R^3$ is selected from $R^4$—$C_{6-10}$arylene, Het, $R^4$-Het, and $R^4$-Het-$R^4$. In one particular embodiment, $R^3$ is selected from $R^4$-phenylene, $R^4$-phenylene-$R^4$, Het, $R^4$-Het, and $R^4$-Het-$R^4$. In one particular embodiment, $R^3$ is selected from $R^4$-phenylene, Het, and $R^4$-Het. In one particular embodiment, $R^3$ is selected from $R^4$-phenylene, Het, and $R^4$-Het, and $R^4$ is unsubstituted, linear or branched $C_{1-6}$alkylene, $C_{3-6}$alkenylene, or $C_{3-6}$alkynylene. In one preferred embodiment, $R^3$ is selected from $R^4$-phenylene, and $R^4$-Het, and $R^4$ is unsubstituted, linear or branched $C_{1-6}$alkylene, $C_{3-6}$alkenylene, or $C_{3-6}$alkynylene.

In one preferred embodiment, $R^3$ is $R^4$—$C_{6-10}$arylene, particularly $R^4$-phenylene. In one such particular embodiment, $R^4$ is unsubstituted, linear or branched $C_{1-6}$alkylene, $C_{3-6}$alkenylene, or $C_{3-6}$alkynylene, more particularly $R^4$ is unsubstituted, linear or branched $C_{1-6}$alkylene. In one preferred embodiment, $R^3$ is $R^4$-phenylene and $R^4$ is selected from —$CH_2$—, —$(CH_2)_5$—, —$CH(CH_3)CH_2$—, and —$C(CH_3)_2CH_2$—. In one preferred embodiment, $R^3$ is selected from

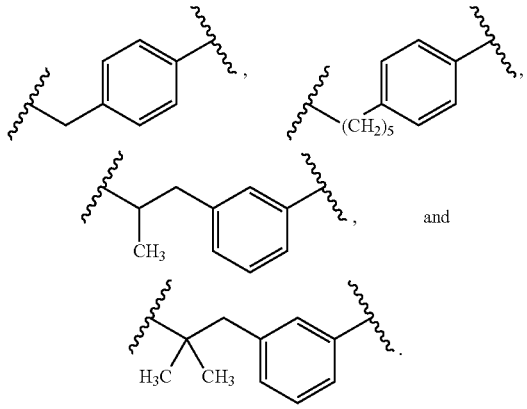

In one embodiment, Het is a 6-membered saturated heterocyclene wherein 1 ring atom is N, and one ring atom is selected from C, N, O and S, wherein the heterocyclene is optionally substituted once with halo, alkyl, alkoxy, oxo or OH. In one particular embodiment, Het is a 6-membered saturated heterocyclene wherein 1 ring atom is N, one ring atoms is selected from C, N, O and S, and all other ring atoms are C and wherein the heterocyclene is optionally substituted once with halo (particularly Cl), alkyl, alkoxy (particularly $OCH_3$), oxo or OH. In one particular embodiment, Het is unsubstituted heterocyclene. In one preferred embodiment, Het is unsubstituted, 6-membered saturated heterocyclene wherein 1 or 2 ring atom(s) is/are N, and all other ring atoms are C.

In those embodiments wherein $R^3$ includes a Het moiety, $R^3$ may be bound to Y through any suitable carbon or heteroatom. However, the selection of variables $R^3$ and Y should be made in view of each other in order to avoid embodiments which are clearly unstable or inoperative based upon the knowledge of those skilled in the art of organic chemistry. For example, when $R^3$ is Het and Het is a nitrogen-containing heterocyclene which is bound to Y through N, one skilled in the art will appreciate that Y is not, for example N($R^8$)C(O) or N($R^8$)C(O)N($R^8$) as such embodiments would result in a N—N bond.

In one embodiment, the compounds of the invention are defined wherein Y is C(O), C(O)N($R^8$)$CH_2$, N($R^8$)C(O), or O—C(O)N($R^8$)$CH_2$. In one particular embodiment Y is C(O) or C(O)N($R^8$)$CH_2$. In one preferred embodiment Y is C(O)N($R^8$)$CH_2$. In one preferred embodiment Y is C(O)N(H)$CH_2$.

Thus in one preferred embodiment, the present invention provides compounds of Formula I';

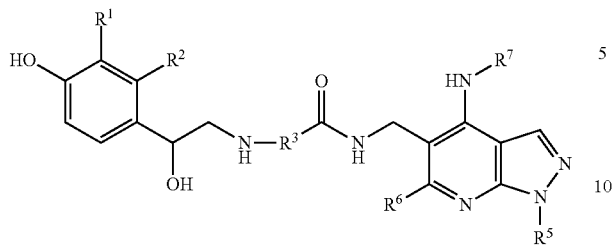

and pharmaceutically acceptable salts thereof, wherein all variables are as defined herein, including all particular and preferred embodiments of variables as described herein.

When Y is bound to a ring of $R^3$ (e.g., arylene such as phenylene, or heterocyclene), Y may be bound in the ortho, meta or para positions of the ring of $R^3$. In one embodiment Y is bound in the meta or para position of the ring of $R^3$.

In one embodiment, the compounds of the invention are defined wherein $R^5$ is alkyl, particularly, $C_{1-3}$alkyl, more particularly —$CH_2CH_3$.

In one embodiment, the compounds of the invention are defined wherein $R^6$ is alkyl, particularly, $C_{1-3}$alkyl, more particularly —$CH_2CH_3$. In one embodiment, $R^6$ is H.

In one embodiment, $R^7$ is selected from an unsubstituted $C_{3-6}$cycloalkyl, substituted $C_{3-6}$cycloalkyl. Substituted cycloalkyl refers to cycloalkyl substituted halo, alkyl, hydroxyl, O-alkyl, oxo, $NH_2$, N(H)alkyl, N(alkyl)$_2$, C(O)$NH_2$, C(O)N(H)alkyl, and C(O)N(alkyl)$_2$.

In one embodiment, $R^7$ is a heterocyclic group selected from formulas (i), (ii), and (iii):

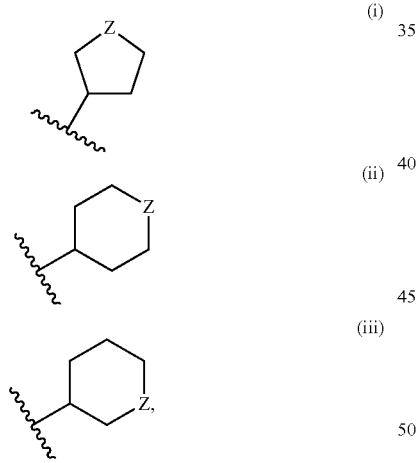

wherein Z is O, S, S(O)$_2$, NH or N—$R^{7a}$, and
$R^{7a}$ is selected from alkyl, C(O)alkyl, C(O)$NH_2$, C(O)N(H)alkyl, and C(O)N(alkyl)$_2$.

In one embodiment, $R^7$ is a heterocyclic group of formula (ii):

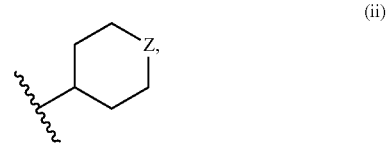

wherein Z is as defined above.

In one embodiment, $R^7$ is a heterocyclic group of formula (ii), wherein Z is O, S, S(O)$_2$, NH or N—$R^{7a}$, and $R^{7a}$ is selected from methyl, ethyl, n-propyl, isopropyl, C(O)methyl, C(O)$NH_2$, C(O)N(H)methyl, and C(O)N(methyl)$_2$.

In one embodiment, $R^7$ is

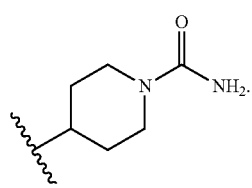 [SMILES: *C1CCN(C(N)=O)CC1]

In one preferred embodiment, $R^7$ is

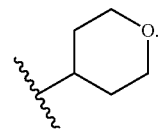

In one embodiment, the compounds of the invention are defined wherein $R^8$ is H or $C_{1-4}$alkyl; more particularly H or $C_{1-3}$alkyl. In one embodiment $R^8$ is H or methyl.

Specific examples of compounds of Formula I set forth in the examples which follow. Preferred compounds of Formula I are selected from:

N-[[1,6-Diethyl-4-[(tetrahydro-2H-pyran-4-yl)-amino]-1H-pyrazolo[3,4-b]pyridin-5-yl]methyl]-3-[2-[[(R)-2-hydroxy-2-(8-hydroxy-2-oxo-1,2-dihydroquinolin-5-yl)ethyl]amino]propyl]benzamide

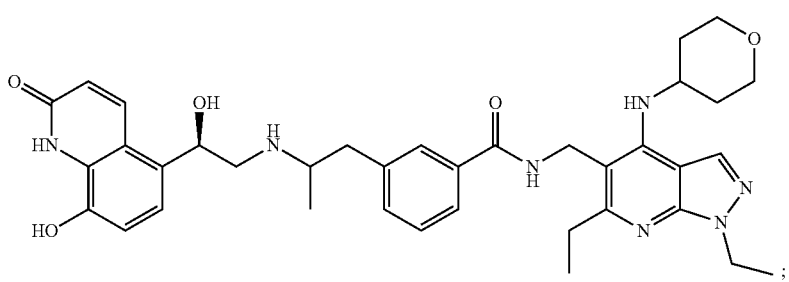 [SMILES: CCc1nc2c(cnn2CC)c(NC2CCOCC2)c1CNC(=O)c1cccc(CC(C)NC[C@H](O)c2ccc(O)c3[nH]c(=O)ccc23)c1]

(R)—N-[[1,6-Diethyl-4-[(tetrahydro-2H-pyran-4-yl)
amino]-1H-pyrazolo[3,4-b]pyridin-5-yl]methyl]-3-[[[2-
hydroxy-2-(8-hydroxy-2-oxo-1,2-dihydroquinolin-5-yl)
ethyl]amino]methyl]benzamide

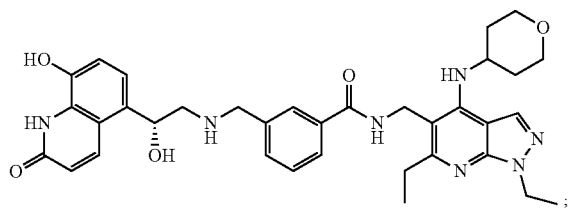 [SMILES: CCc1nc2c(cnn2CC)c(NC2CCOCC2)c1CNC(=O)c1cccc(CNC[C@H](O)c2ccc(O)c3[nH]c(=O)ccc23)c1]

(R)—N-[[1,6-diethyl-4-[(tetrahydro-2H-pyran-4-yl)amino]-
1H-pyrazolo[3,4-b]pyridin-5-yl]methyl]-4-[[[2-hydroxy-
2-(8-hydroxy-2-oxo-1,2-dihydroquinolin-5-yl)ethyl]
amino]methyl]benzamide

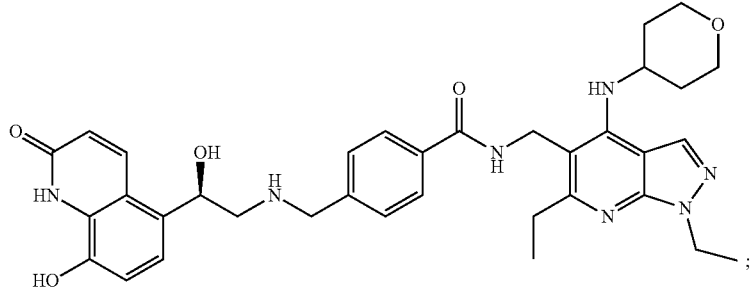 [SMILES: CCc1nc2c(cnn2CC)c(NC2CCOCC2)c1CNC(=O)c1ccc(CNC[C@H](O)c2ccc(O)c3[nH]c(=O)ccc23)cc1]

(R)—N-[[1,6-diethyl-4-[(tetrahydro-2H-pyran-4-yl)amino]-
1H-pyrazolo[3,4-b]pyridin-5-yl]methyl]-4-[5-[[2-hy-
droxy-2-(8-hydroxy-2-oxo-1,2-dihydroquinolin-5-yl)
ethyl]amino]pentyl]benzamide

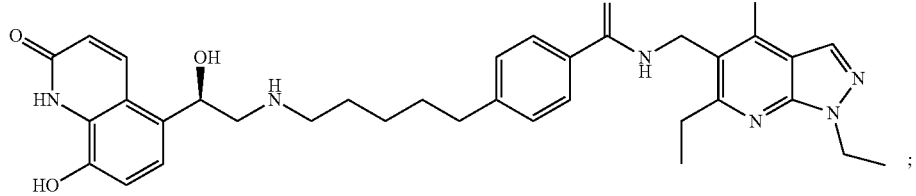

(R)—N-[[1,6-Diethyl-4-[(tetrahydro-2H-pyran-4-yl)
amino]-1H-pyrazolo[3,4-b]pyridin-5-yl]methyl]-8-[[2-
hydroxy-2-(8-hydroxy-2-oxo-1,2-dihydroquinolin-5-yl)
ethyl]amino]octanamide

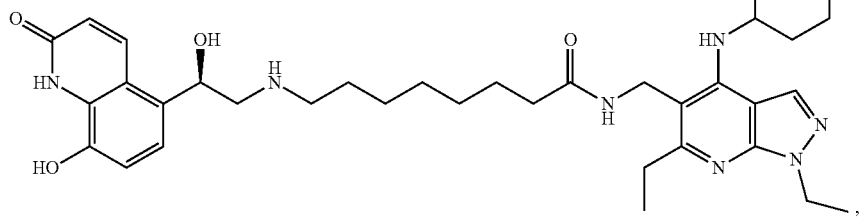

and pharmaceutically acceptable salts thereof.

The compounds of Formula I, may be in the form of a free base or a salt, particularly a pharmaceutically acceptable salt.

For a review of pharmaceutically acceptable salts see Berge et al., *J. Pharma Sci.* (1977) 66:1-19.

Pharmaceutically acceptable salts formed from inorganic or organic acids include for example, hydrochloride, hydrobromide, hydroiodide, sulfate, bisulfate, nitrate, sulfamate, phosphate, hydrogen phosphate, acetate, trifluoroacetate, maleate, malate, fumarate, lactate, tartrate, citrate, formate, gluconate, succinate, pyruvate, tannate, ascorbate, palmitate, salicylate, stearate, phthalate, alginate, polyglutamate, oxalate, oxaloacetate, saccharate, benzoate, alkyl or aryl sulfonates (e.g., methanesulfonate, ethanesulfonate, benzenesulfonate, p-toluenesulfonate or naphthalenesulfonate) and isothionate; complexes formed with amino acids such as lysine, arginine, glutamic acid, glycine, serine, threonine, alanine, isoleucine, leucine and the like. The compounds of the invention may also be in the form of salts formed from elemental anions such as chlorine, bromine or iodine.

For therapeutic use, salts of active ingredients of the compounds of Formula I will be pharmaceutically acceptable, i.e. they will be salts derived from a pharmaceutically acceptable acid. However, salts of acids which are not pharmaceutically acceptable may also find use, for example, in the preparation or purification of a pharmaceutically acceptable compound. Trifluoroacetate salts, for example, may find such use. All salts, whether or not derived from a pharmaceutically acceptable acid, are within the scope of the present invention. In one embodiment, the compounds of Formula I are in the form of the trifluoroacetate salt. In one embodiment, the compounds of Formula I are in the form of the hydrochloride salt.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space. "Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography. "Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York.

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species.

The term "tautomers" refers to a type of stereoisomers in which migration of a hydrogen atom results in two or more structures. The compounds of Formula I may exist in different tautomeric forms. One skilled in the art will recognize that amidines, amides, guanidines, ureas, thioureas, heterocycles and the like can exist in tautomeric forms. All possible tautomeric forms of the amidines, amides, guanidines, ureas, thioureas, heterocycles and the like of all of the embodiments of Formula I are within the scope of the instant invention. Tautomers exist in equilibrium and thus the depiction of a single tautomer in the formulas provided will be understood by those skilled in the art to refer equally to all possible tautomers.

It is to be noted that all enantiomers, diastereomers, and racemic mixtures, tautomers, polymorphs, pseudopolymorphs of compounds within the scope of Formula I and pharmaceutically acceptable salts thereof are embraced by the present invention. All mixtures of such enantiomers and diastereomers, including enantiomerically enriched mixtures and diastereomerically enriched mixtures are within the scope of the present invention. Enantionmerically enriched mixtures are mixtures of enantiomers wherein the ratio of the specified enantiomer to the alternative enantiomer is greater than 50:50. More particularly, an enantiomerically enriched mixture comprises at least about 75% of the specified enantiomer, and preferably at least about 85% of the specified enantiomer. In one embodiment, the enantiomerically enriched mixture is substantially free of the other enantiomer. Similarly, diastereomerically enriched mixtures are mixtures of diastereomers wherein the amount of the specified diastereomer is greater than the amount of each alternative diastereomer. More particularly, a diastereomerically enriched mixture comprises at least about 75% of the specified diastereomer, and preferably at least about 85% of the specified diastereomer. In one embodiment, the diastereomerically enriched mixture is substantially free of all other diastereomers. The term "substantially free of" will be understood by those skilled in the art to indicate less than a 5% presence of other diastereomers, preferably less than 1%, more preferably less than 0.1%. In other embodiments no other diastereomers will be present or the amount of any other diastereomers present will be below the level of detection. Stereoisomers may be separated by techniques known in the art, including high performance liquid chromatography (HPLC) and crystallization of chiral salts.

For illustrative purposes, specific examples of enantiomers within the scope of the present invention include:
N-[[1,6-Diethyl-4-[(tetrahydro-2H-pyran-4-yl)amino]-1H-pyrazolo[3,4-b]pyridin-5-yl]methyl]-3-[2-[[(R)-2-hydroxy-2-(8-hydroxy-2-oxo-1,2-dihydroquinolin-5-yl)ethyl]amino]propyl]benzamide

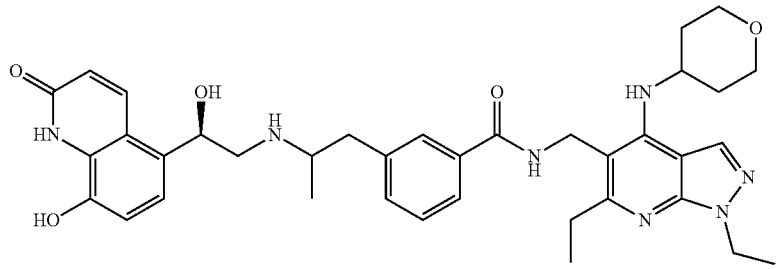 [SMILES: CCc1nc2c(cnn2CC)c(NC2CCOCC2)c1CNC(=O)c1cccc(CC(C)NC[C@H](O)c2ccc(O)c3[nH]c(=O)ccc23)c1]

and
N-[[1,6-Diethyl-4-[(tetrahydro-2H-pyran-4-yl)amino]-1H-pyrazolo[3,4-b]pyridin-5-yl]methyl]-3-[2-[[(S)-2-hydroxy-2-(8-hydroxy-2-oxo-1,2-dihydroquinolin-5-yl)ethyl]amino]propyl]benzamide

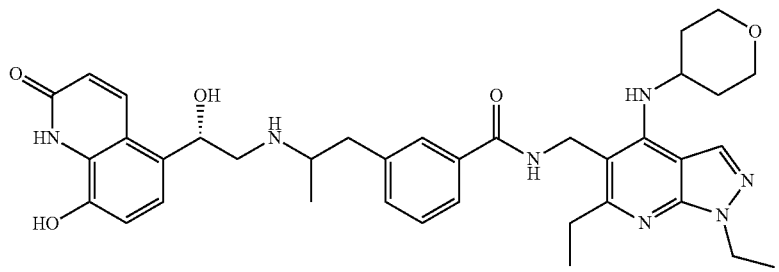 [SMILES: CCc1nc2c(cnn2CC)c(NC2CCOCC2)c1CNC(=O)c1cccc(CC(C)NC[C@@H](O)c2ccc(O)c3[nH]c(=O)ccc23)c1]

In one embodiment, the present invention provides an enantiomerically enriched mixture comprising (R)—N-[[1,6-diethyl-4-[(tetrahydro-2H-pyran-4-yl)amino]-1H-pyrazolo[3,4-b]pyridin-5-yl]methyl]-4-[5-[[2-hydroxy-2-(8-hydroxy-2-oxo-1,2-dihydroquinolin-5-yl)ethyl]amino]pentyl]benzamide

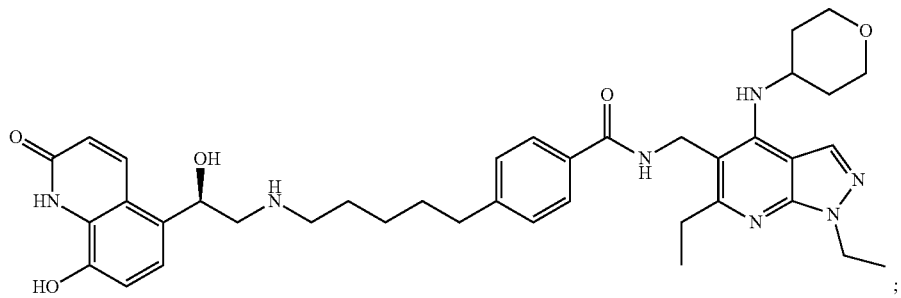 [SMILES: CCc1nc2c(cnn2CC)c(NC2CCOCC2)c1CNC(=O)c1ccc(CCCCCNC[C@H](O)c2ccc(O)c3[nH]c(=O)ccc23)cc1 ; ";"]

or a pharmaceutically acceptable salt thereof, as the predominant isomer.

A compound of Formula I and pharmaceutically acceptable salts thereof may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism also includes the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of Formula I and pharmaceutically acceptable salts thereof.

A compound of Formula I and pharmaceutically acceptable salts thereof may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of Formula I and pharmaceutically acceptable salts thereof.

The compounds of the invention may also be in the form of prodrugs. More specifically, the compounds may be present in the form of in vivo cleavable esters of the compounds of Formula I and salts of such esters. Examples of suitable esters include acetate, pivalate, tartrate, maleate, succinate and the like.

Uses

The compounds of the invention exhibit bifunctional activity as a dual pharmacophore phosphodiesterase 4 inhibitor (PDE4i), and beta agonists. Without being bound by any particular theory, it is believed that the compounds of the invention may function in vivo by reducing pulmonary inflammation (by elevation of cytosolic levels of 3',5'-cyclic adenosine monophosphate (cAMP) through inhibition of the PDE4 enzyme and potentially other pro-inflammatory mechanisms) and inducing bronchodilation (by the beta adrenergic receptor agonist moiety). There may also be further positive cooperative anti-inflammatory effects through simultaneous interaction of downstream signaling pathways via modulation of both targets with the same cell.

Local delivery of a single bi-functional compound which has dual activity as a PDE4i and beta agonist offers advantages over combination and conjunctive therapies. In particular, such bi-functional compounds may provide cooperative anti-inflammatory or bronchodilator effects though simultaneous modulation of the same pathways. Utilizing the bi-functional compounds of the present invention allows co-disposition in the same microenvironment which cannot be ensured with the individual drug compounds of combination or conjunctive therapy. In addition, such bi-functional compounds may provide reduced off-target effects leading to decreased risk of adverse events which may be associated with individual PDE4i or beta agonist compounds. If desired however, the dual active compounds of the present invention may nevertheless be combined with other pharmaceutical and non-pharmaceutical therapies which are conventionally employed in the treatment of respiratory diseases. Further detail regarding combination therapies utilizing the compounds of the present invention are described below.

As a consequence, the compounds of the invention are useful as medicaments, particularly for the treatment of clinical conditions for which a PDE4i or beta agonist may be indicated. Such conditions include the treatment of pulmonary inflammation or bronchoconstriction and a variety of respiratory diseases. For a review of potential therapeutic activities of PDE4i in the treatment of respiratory diseases see e.g., Kroegel & Foerster, Phosphdiesterase-4 inhibitors as a novel approach for the treatment of respiratory disease: cilomilast, *Expert Opin. Investig. Drugs* (2007) 16:109-124; Dastidar et al., Therapeutic benefit of PDE4 Inhibitors in inflammatory diseases, *Curr Opin Investig Drugs* (2007) 8:364-372; Krymskaya, et al., Phosphodiesterases regulate airway smooth muscle function in health and disease, *Curr. Top. Dev. Biol.* (2007) 79:61-74; and Spina, PDE4 inhibitors: current status, *Brit. J. Pharmacol.* 2008; 155:308-15.

In particular, the compounds of the invention are useful in methods of treating a variety of respiratory conditions such as diseases associated with reversible or irreversible airway obstruction, chronic obstructive pulmonary disease (COPD), including acute exacerbations of COPD, asthma, bronchiectasis (including bronchiectasis due to conditions other than cystic fibrosis), acute bronchitis, chronic bronchitis, post-viral cough, cystic fibrosis, emphysema, pneumonia, panbronchiolitis, and transplant-associated bronchiolitis, including lung- and bone marrow-transplant associated bronchiolitis, in a human in need thereof. The compounds of the invention may also be useful for treating ventilator-associated tracheobronchitis and/or preventing ventilator-associated pneumonia in ventilated patients. With respect to the treatment of acute exacerbations of COPD, the compounds of the invention are useful for reducing the frequency, severity or duration of acute exacerbation of COPD and/or for reducing the frequency, severity or duration of one of more symptoms of acute exacerbation of COPD.

All therapeutic uses and methods described herein are carried out by the step of administering an effective amount of a compound of the invention (a compound of Formula I or a pharmaceutically acceptable salt thereof) to a subject (typically mammal and preferably human) in need of treatment.

In one aspect, the present invention provides a method for the treatment of a condition in a mammal, such as a human, for which a PDE 4I or a beta agonist is indicated.

The terms "treating" and "treatment", as used herein refers to reversing, alleviating, inhibiting the progress of, or preventing the disorder or condition or one or more symptoms of such disorder or condition.

In one embodiment the invention provides a method for the treatment of a respiratory disease. In one embodiment the invention provides a method for the treatment of a disease associated with reversible or irreversible airway obstruction in a mammal, particularly a human, in need thereof. In one particular embodiment the present invention provides a method for the treatment of COPD in a mammal, particularly a human in need thereof. In one particular embodiment the present invention provides a method for reducing the frequency, severity or duration of acute exacerbation of COPD or for the treatment of one or more symptoms of acute exacerbation of COPD in a mammal, particularly a human in need thereof. In one embodiment the invention provides a method for the treatment of asthma in a mammal, particularly a human, in need thereof. In one embodiment the invention provides a method for the treatment of bronchiectasis (including bronchiectasis due to conditions other than cystic fibrosis) in a mammal, particularly a human, in need thereof. In one embodiment the invention provides a method for the treatment of bronchitis, including acute and chronic bronchitis in a mammal, particularly a human, in need thereof. In one embodiment the invention provides a method for the treatment of post-viral cough in a mammal, particularly a human, in need thereof. In one embodiment the invention provides a method for the treatment of cystic fibrosis in a mammal, particularly a human, in need thereof. In one embodiment the invention provides a method for the treatment of emphysema in a mammal, particularly a human in need thereof. In one embodiment the invention provides a method for the treatment of pneumonia in a mammal, particularly a human in need thereof. In one embodiment the invention provides a method for the treatment of panbronchiolitis in a mammal, particularly a human in need thereof. In one embodiment the invention provides a method for the treatment of transplant-associated bronchiolitis, including lung- and bone marrow-transplant associated bronchiolitis in a mammal, particularly a human in need thereof. In one embodiment the invention provides a method for treating ventilator-associated tracheobronchitis and/or preventing ventilator-associated pneumonia in a ventilated human in need thereof. In one embodiment the invention provides a method for treating sinusitis in a mammal, particularly a human in need thereof. There is also provided a compound of the invention for use in medical therapy, particularly for use in the treatment of condition in a mammal, such as a human, for which a PDE4i or beta agonist is indicated. In one embodiment the invention provides a method for the treatment of a respiratory disease. In one embodiment there is provided a compound of the invention for use in the treatment of a disease associated with reversible or irreversible airway obstruction in a mammal, particularly a human, in need thereof. In one particular embodiment there is provided a compound of the invention for use in the treatment of chronic obstructive pulmonary disease (COPD) in a mammal, particularly a human in need thereof. In one embodiment, there is provided a compound of the invention for use in reducing the frequency, severity or duration of acute exacerbation of COPD or for the treatment of one or more symptoms of acute exacerbation of COPD, in a mammal, particularly a human, in need thereof. In one embodiment there is provided a compound of the invention for use in the treatment of asthma in a mammal, particularly a human, in need thereof. In one embodiment there is provided a compound for use in the treatment of bronchiectasis, including bronchiectasis due to conditions other than cystic fibrosis, in a mammal, particularly a human, in need thereof. In one embodiment there is provided a compound for use in the treatment of bronchitis, including acute bronchitis and chronic bronchitis, in a mammal, particularly a human, in need thereof. In one embodiment there is provided a compound for use in the treatment of post-viral cough, in a mammal, particularly a human, in need thereof. In one embodiment there is provided a compound for use in the treatment of cystic fibrosis in a mammal, particularly a human in need thereof. In one embodiment there is provided a compound of the invention for use in the treatment of emphysema in a mammal, particularly a human, in need thereof. In one embodiment there is provided a compound of the invention for use in the treatment of pneumonia in a mammal, particularly a human, in need thereof. In one embodiment there is provided a compound of the invention for use in the treatment of panbronchiolitis or transplant-associated bronchiolitis, including lung- and bone marrow-transplant associated bronchiolitis in a mammal, particularly a human, in need thereof. In one embodiment there is provided a compound of the invention for use in the treatment of ventilator-associated tracheobronchitis or preventing ventilator-associated pneumonia in a ventilated human in need thereof. In one embodiment there is provided a compound of the invention for use in the treatment of sinusitis in a mammal, particularly a human, in need thereof.

The present invention also provides the use of a compound of the invention in the manufacture of a medicament for the treatment of a condition in a mammal, such as a human, for which a PDE4i or beta agonist is indicated. In one embodiment is provided the use of a compound of the invention in the manufacture of a medicament for the treatment of a respiratory disease. In one embodiment is provided the use of a compound of the invention in the manufacture of a medicament for the treatment of diseases associated with reversible or irreversible airway obstruction, chronic obstructive pulmonary disease (COPD), acute exacerbations of COPD, asthma, bronchiectasis (including bronchiectasis due to conditions other than cystic fibrosis), bronchitis (including acute bronchitis and chronic bronchitis), post-viral cough, cystic fibrosis, emphysema, pneumonia, panbronchiolitis, transplant-associated bronchiolitis, (including lung- and bone marrow-transplant associated bronchiolitis), ventilator-associated tracheobronchitis or preventing ventilator-associated pneumonia or treating sinusitis.

The term "effective amount", as used herein, is an amount of compound of the invention which is sufficient in the subject to which it is administered, to elicit the biological or medical response of a cell culture, tissue, system, or mammal (including human) that is being sought, for instance by a researcher or clinician. The term also includes within its scope, amounts effective to enhance normal physiological function. In one embodiment, the effective amount is the amount needed to provide a desired level of drug in the secretions and tissues of the airways and lungs, or alternatively, in the bloodstream of a subject to be treated to give an anticipated physiological response or desired biological effect when such a composition is administered by inhalation. For example, an effective amount of a compound of the invention for the treatment of a condition for which a PDE4i or beta agonist is indicated is sufficient in the subject to which it is administered to treat the particular condition. In one embodiment an effective amount is an amount of a compound of the invention which is sufficient for the treatment of COPD or cystic fibrosis in a human.

The precise effective amount of the compounds of the invention will depend on a number of factors including but not limited to the species, age and weight of the subject being treated, the precise condition requiring treatment and its severity, the bioavailability, potency, and other properties of the specific compound being administered, the nature of the formulation, the route of administration, and the delivery device, and will ultimately be at the discretion of the attendant physician or veterinarian. Further guidance with respect to appropriate dose may be found in considering conventional dosing of other PDE4i's such as cilomilast or roflumilast and other beta agonist's such as salmeterol, with due consideration also being given to any differences in potency between those compounds and the compounds of the present invention and that bi-functional nature of the compounds of the present invention.

An estimated dose administered topically to the airway surfaces of a subject (e.g., by inhalation) of a compound of the invention for treatment of a 70 kg human may be in the range of from about 20 to about 1000 µg. The selection of the specific dose for a patient will be determined by the attendant physician, clinician or veterinarian of ordinary skill in the art based upon a number of factors including those noted above. In one particular embodiment the dose of a compound of the invention for the treatment of a 70 kg human will be in the range of from about 50 to about 750 µg. In one preferred embodiment, the dose of a compound of the invention for the treatment of a 70 kg human will be in the range of from about 50 to about 750 µg. The foregoing suggested doses may be adjusted using conventional dose calculations if the compound is administered via a different route. Determination of an appropriate dose for administration by other routes is within the skill of those in the art in light of the foregoing description and the general knowledge in the art.

Delivery of an effective amount of a compound of the invention may entail delivery of a single dosage form or multiple unit doses which may be delivered contemporaneously or separate in time over a designated period, such as 24 hours. A dose of a compound of the invention (alone or in the form of a composition comprising the same) may be administered from one to ten times per day. Typically, a compound of the invention (alone or in the form of a composition comprising the same) will be administered four, three, two, or most preferably once per day (24 hours).

Compositions

While it is possible for a compound of the invention to be administered alone, it is preferable to present it in the form of a composition, particularly a pharmaceutical composition (formulation). Thus, in another aspect, the invention provides compositions, and particularly pharmaceutical compositions (such as an inhalable pharmaceutical composition) comprising a compound of the invention as an active ingredient, and a pharmaceutically acceptable excipient, diluent or carrier. The term "active ingredient" as employed herein refers to any compound of the invention or combination of two or more compounds of the invention in a pharmaceutical composition. The pharmaceutically acceptable excipient(s), diluent(s) or carrier(s) must be acceptable in the sense of being compatible with the other ingredients of the formulation and not deleterious to the recipient thereof. Generally, the pharmaceutically acceptable excipient(s), diluent(s) or carrier(s) employed in the pharmaceutical formulation are "non-toxic" meaning that it/they is/are deemed safe for consumption in the amount delivered in the formulation and "inert" meaning that it/they does/do not appreciable react with or result in an undesired effect on the therapeutic activity of the active ingredient(s). Pharmaceutically acceptable excipients, diluents and carriers are conventional in the art and may be selected using conventional techniques, based upon the desired route of administration. See, REMINGTON'S, PHARMACEUTICAL SCIENCES, Lippincott Williams & Wilkins; $21^{st}$ Ed (May 1, 2005). Preferably, the pharmaceutically acceptable excipient(s), diluent(s) or carrier(s) are Generally Regarded As Safe (GRAS) according to the FDA.

Pharmaceutical compositions according to the invention include those suitable for topical administration and administration to the respiratory tract, including the nasal cavities and sinuses, oral and extrathoracic airways, and the lungs, including by use of aerosols which may be delivered by means of various types of dry powder inhalers, pressurized metered dose inhalers, softmist inhalers, nebulizers, or insufflators. The most suitable route of administration may depend upon, several factors including the patient and the condition or disorder being treated.

The formulations may be presented in unit dosage form or in bulk form as for example in the case of formulations to be metered by an inhaler and may be prepared by any of the methods well known in the art of pharmacy. Generally, the methods include the step of bringing the active ingredient into association with the carrier, diluent or excipient and optionally one or more accessory ingredients. In general the formulations are prepared by uniformly and intimately bringing into association the active ingredient with one or more liquid carriers, diluents or excipients or finely divided solid carriers, diluents or excipients, or both, and then, if necessary, shaping the product into the desired formulation.

In one preferred embodiment, the composition is an inhalable pharmaceutical composition which is suitable for inhalation and delivery to the endobronchial space. Typically, such composition is in the form of an aerosol comprising particles for delivery using a nebulizer, pressurized metered dose inhaler (MDI), softmist inhaler, or dry powder inhaler (DPI). The aerosol formulation used in the methods of the present invention may be a liquid (e.g., solution) suitable for administration by a nebulizer, softmist inhaler, or MDI, or a dry powder suitable for administration by an MDI or DPI.

Aerosols used to administer medicaments to the respiratory tract are typically polydisperse; that is they are comprised of particles of many different sizes. The particle size distribution is typically described by the Mass Median Aerodynamic Diameter (MMAD) and the Geometric Standard Deviation (GSD). For optimum drug delivery to the endobronchial space the MMAD is in the range from about 1 to about 10 µm and preferably from about 1 to about 5 µm, and the GSD is less than 3, and preferably less than about 2. Aerosols having a MMAD above 10 µm are generally too large when inhaled to reach the lungs. Aerosols with a GSD greater than about 3 are not preferred for lung delivery as they deliver a high percentage of the medicament to the oral cavity. To achieve these particle sizes in powder formulation, the particles of the active ingredient may be size reduced using conventional techniques such as micronisation or spray drying. Non-limiting examples of other processes or techniques that can be used to produce respirable particles include spray drying, precipitation, supercritical fluid, and freeze drying. The desired fraction may be separated out by air classification or sieving. In one embodiment, the particles will be crystalline. For liquid formulations, the particle size is determined by the selection of a particular model of nebulizer, softmist inhaler, or MDI. Aerosol particle size distributions are determined using devices well known in the art. For example a multi-stage Anderson cascade impactor or other suitable method such as those specifically cited within the US Pharmacopoeia Chapter 601 as characterizing devices for aerosols emitted from metered-dose and dry powder inhalers.

Dry powder compositions for topical delivery to the lung by inhalation may be formulated without excipient or carrier and instead including only the active ingredients in a dry powder form having a suitable particle size for inhalation. Dry powder compositions may also contain a mix of the active ingredient and a suitable powder base (carrier/diluent/excipient substance) such as mono-, di- or poly-saccharides (e.g., lactose or starch). Lactose is typically the preferred excipient for dry powder formulations. When a solid excipient such as lactose is employed, generally the particle size of the excipient will be much greater than the active ingredient to aid the dispersion of the formulation in the inhaler.

Non-limiting examples of dry powder inhalers include reservoir multi-dose inhalers, pre-metered multi-dose inhalers, capsule-based inhalers and single-dose disposable inhalers. A reservoir inhaler contains a large number of doses (e.g. 60) in one container. Prior to inhalation, the patient actuates the inhaler which causes the inhaler to meter one dose of medicament from the reservoir and prepare it for inhalation. Examples of reservoir DPIs include but are not limited to the Turbohaler® by AstraZeneca and the ClickHaler® by Vectura. In a pre-metered multi-dose inhaler, each individual dose has been manufactured in a separate container, and actuation of the inhaler prior to inhalation causes a new dose of drug to be released from its container and prepared for inhalation. Examples of multidose DPI inhalers include but are not limited to Diskus® by GSK, Gyrohaler® by Vectura, and Prohaler® by Valois. During inhalation, the inspiratory flow of the patient accelerates the powder out of the device and into the oral cavity. For a capsule inhaler, the formulation is in a capsule and stored outside the inhaler. The patient puts a capsule in the inhaler, actuates the inhaler (punctures the capsule), then inhales. Examples include the Rotohaler™ (GlaxoSmithKline), Spinhaler™ (Novartis), HandiHaler™ (IB), TurboSpin™ (PH&T). With single-dose disposable inhalers, the patient actuates the inhaler to prepare it for inhalation, inhales, then disposes of the inhaler and packaging. Examples include the Twincer™ (U Groningen), One-Dose™ (GFE), and Manta Inhaler™ (Manta Devices).

Generally, dry powder inhalers utilize turbulent flow characteristics of the powder path to cause the excipient-drug aggregates to disperse, and the particles of active ingredient are deposited in the lungs. However, certain dry powder inhalers utilize a cyclone dispersion chamber to produce particles of the desired respirable size. In a cyclone dispersion chamber, the drug enters a coin shaped dispersion chamber tangentially so that the air path and drug move along the outer circular wall. As the drug formulation moves along this circular wall it bounces around and agglomerates are broken apart by impact forces. The air path spirals towards the center of the chamber exiting vertically. Particles that have small enough aerodynamic sizes can follow the air path and exit the chamber. In effect, the dispersion chamber works like a small jet mill. Depending on the specifics of the formulation, large lactose particles may be added to the formulation to aid in the dispersion through impact with the API particles.

The Twincer™ single-dose disposable inhaler appears to operate using a coin-shaped cyclone dispersion chamber referred to as an "air classifier." See, U.S. Published Patent Application No. 2006/0237010 to Rijksuniversiteit Groningen. Papers published by the University of Groningen, have stated that a 60 mg dose of pure micronized colistin sulfomethate could be effectively delivered as an inhalable dry powder utilizing this technology.

In preferred embodiments, the aerosol formulation is delivered as a dry powder using a dry powder inhaler wherein the particles emitted from the inhaler have an MMAD in the range of about 1 μm to about 5 μm and a GSD about less than 2.

Examples of suitable dry powder inhalers and dry powder dispersion devices for use in the delivery of compounds and compositions according to the present invention include but are not limited to those disclosed in U.S. Pat. No. 7,520,278; U.S. Pat. No. 7,322,354; U.S. Pat. No. 7,246,617; U.S. Pat. No. 7,231,920; U.S. Pat. No. 7,219,665; U.S. Pat. No. 7,207,330; U.S. Pat. No. 6,880,555; U.S. Pat. No. 5,522,385; U.S. Pat. No. 6,845,772; U.S. Pat. No. 6,637,431; U.S. Pat. No. 6,329,034; U.S. Pat. No. 5,458,135; U.S. Pat. No. 4,805,811; and U.S. Published Patent Application No. 2006/0237010.

In one embodiment, the pharmaceutical formulation according to the invention is a dry powder for inhalation which is formulated for delivery by a Diskus®-type device. The Diskus® device comprises an elongate strip formed from a base sheet having a plurality of recesses spaced along its length and a lid sheet hermetically but peelably sealed thereto to define one or more containers, each container having therein an inhalable formulation containing a predetermined amount of active ingredient either alone or in admixture with one or more carriers or excipients (e.g., lactose) and/or other therapeutically active agents. Preferably, the strip is sufficiently flexible to be wound into a roll. The lid sheet and base sheet will preferably have leading end portions which are not sealed to one another and at least one of the leading end portions is constructed to be attached to a winding means. Also, preferably the hermetic seal between the base and lid sheets extends over their whole width. To prepare the dose for inhalation, the lid sheet may preferably be peeled from the base sheet in a longitudinal direction from a first end of the base sheet.

In one embodiment, the pharmaceutical formulation according to the invention is a dry powder for inhalation which is formulated for delivery using a single-dose disposable inhaler, and particularly the Twincer™ inhaler. The Twincer™ inhaler comprises a foil laminate blister with one or more recesses and a lid sheet hermetically but peelably sealed thereto to define a plurality of containers. Each container has therein an inhalable formulation containing a predetermined amount of active ingredient(s) either alone or in admixture with one or more carriers or excipeints (e.g., lactose). The lid sheet will preferably have a leading end portion which is constructed to project from the body of the inhaler. The patient would operate the device and thereby administer the aerosol formulation by 1) removing the outer packaging overwrap, 2) pulling the foil tab to uncover the drug in the blister and 3) inhaling the drug from the blister.

In another embodiment, the pharmaceutical formulation according to the invention is a dry powder for inhalation wherein the dry powder is formulated into microparticles as described in PCT Publication No. WO2009/015286 or WO2007/114881, both to NexBio. Such microparticles are generally formed by adding a counterion to a solution containing a compound of the invention in a solvent, adding an antisolvent to the solution; and gradually cooling the solution to a temperature below about 25° C., to form a composition containing microparticles comprising the compound. The microparticles comprising the compound may then be separated from the solution by any suitable means such as sedimentation, filtration or lyophilization. Suitable counterions, solvents and antisolvents for preparing microparticles of the compounds of the invention are described in WO2009/015286.

In another embodiment, a pharmaceutical composition according to the invention is delivered as a dry powder using a metered dose inhaler. Non-limiting examples of metered dose inhalers and devices include those disclosed in U.S. Pat. No. 5,261,538; U.S. Pat. No. 5,544,647; U.S. Pat. No. 5,622,163; U.S. Pat. No. 4,955,371; U.S. Pat. No. 3,565,070; U.S. Pat. No. 3,361,306 and U.S. Pat. No. 6,116,234 and U.S. Pat. No. 7,108,159. In a preferred embodiment, a compound of the invention is delivered as a dry powder using a metered dose inhaler wherein the emitted particles have an MMAD that is in the range of about 1 µm to about 5 µm and a GSD that is less than about 2.

Liquid aerosol formulations for delivery to the endobronchial space or lung by inhalation may for example be formulated as aqueous solutions or suspensions or as aerosols delivered from pressurized packs, such as metered dose inhalers, with the use of suitable liquefied propellants, softmist inhalers, or nebulizers. Such aerosol compositions suitable for inhalation can be either a suspension or a solution and generally contain the active ingredient(s) together with a pharmaceutically acceptable carrier or diluent (e.g., water (distilled or sterile), saline, hypertonic saline, or ethanol) and optionally one or more other therapeutically active agents.

Aerosol compositions for delivery by pressurized metered dose inhalers typically further comprise a pharmaceutically acceptable propellant. Examples of such propellants include fluorocarbon or hydrogen-containing chlorofluorocarbon or mixtures thereof, particularly hydrofluoroalkanes, e.g., dichlorodifluoromethane, trichlorofluoromethane, dichlorotetrafluoroethane, especially 1,1,1,2-tetrafluoroethane, 1,1,1,2,3,3,3,-heptafluoro-n-propane or a mixture thereof. The aerosol composition may be excipient free or may optionally contain additional formulation excipients well known in the art such as surfactants e.g., oleic acid or lecithin and cosolvents e.g., ethanol. Pressurized formulations will generally be retained in a canister (e.g., an aluminum canister) closed with a valve (e.g., a metering valve) and fitted into an actuator provided with a mouthpiece.

In another embodiment, a pharmaceutical composition according to the invention is delivered as a liquid using a metered dose inhaler. Non-limiting examples of metered dose inhalers and devices include those disclosed in U.S. Pat. Nos. 6,253,762, 6,413,497, 7,601,336, 7,481,995, 6,743,413, and 7,105,152. In a preferred embodiment, a compound of the invention is delivered as a dry powder using a metered dose inhaler wherein the emitted particles have an MMAD that is in the range of about 1 µm to about 5 µm and a GSD that is less than about 2.

In one embodiment the aerosol formulation is suitable for aerosolization by a jet nebulizer, or ultrasonic nebulizer including static and vibrating porous plate nebulizers. Liquid aerosol formulations for nebulization may be generated by solubilizing or reconstituting a solid particle formulation or may be formulated with an aqueous vehicle with the addition of agents such as acid or alkali, buffer salts, and isotonicity adjusting agents. They may be sterilized by in-process techniques such as filtration, or terminal processes such as heating in an autoclave or gamma irradiation. They may also be presented in non-sterile form.

Patients can be sensitive to the pH, osmolality, and ionic content of a nebulized solution. Therefore these parameters should be adjusted to be compatible with the active ingredient and tolerable to patients. The most preferred solution or suspension of active ingredient will contain a chloride concentration>30 mM at pH 4.5-8.0 and an osmolality of from about 800-1600 mOsm/kg. The pH of the solution can be controlled by either titration with common acids (hydrochloric acid or sulfuric acid, for example) or bases (sodium hydroxide, for example) or via the use of buffers. Commonly used buffers include citrate buffers, acetate buffers, and phosphate buffers. Buffer strengths can range from 2 mM to 50 mM.

Such formulations may be administered using commercially available nebulizers or other atomizer that can break the formulation into particles or droplets suitable for deposition in the respiratory tract. Non-limiting examples of nebulizers which may be employed for the aerosol delivery of a composition of the invention include pneumatic jet nebulizers, vented or breath enhanced jet nebulizers, or ultrasonic nebulizers including static or vibrating porous plate nebulizers.

A jet nebulizer utilizes a high velocity stream of air blasting up through a column of water to generate droplets. Particles unsuitable for inhalation impact on walls or aerodynamic baffles. A vented or breath enhanced nebulizer works in essentially the same way as a jet nebulizer except that inhaled air passes through the primary droplet generation area to increase the output rate of the nebulizer while the patient inhales.

In an ultrasonic nebulizer, vibration of a piezoelectric crystal creates surface instabilities in the drug reservoir that cause droplets to be formed. In porous plate nebulizers pressure fields generated by sonic energy force liquid through the mesh pores where it breaks into droplets by Rayleigh breakup. The sonic energy may be supplied by a vibrating horn or plate driven by a piezoelectric crystal, or by the mesh itself vibrating. Non-limiting examples of atomizers include any single or twin fluid atomizer or nozzle that produces droplets of an appropriate size. A single fluid atomizer works by forcing a liquid through one or more holes, where the jet of liquid breaks up into droplets. Twin fluid atomizers work by either forcing both a gas and liquid through one or more holes, or by impinging a jet of liquid against another jet of either liquid or gas.

The choice of nebulizer which aerosolizes the aerosol formulation is important in the administration of the active ingredient(s). Different nebulizers have differing efficiencies based their design and operation principle and are sensitive to the physical and chemical properties of the formulation. For example, two formulations with different surface tensions may have different particle size distributions. Additionally, formulation properties such as pH, osmolality, and permeant ion content can affect tolerability of the medication, so preferred embodiments conform to certain ranges of these properties.

In a preferred embodiment, the formulation for nebulization is delivered to the endobronchial space as an aerosol having an MMAD between about 1 μm and about 5 μm and a GSD less than 2 using an appropriate nebulizer. To be optimally effective and to avoid upper respiratory and systemic side effects, the aerosol should not have a MMAD greater than about 5 μm and should not have a GSD greater than about 2. If an aerosol has an MMAD larger than about 5 μm or a GSD greater than about 2, a large percentage of the dose may be deposited in the upper airways decreasing the amount of drug delivered to the site of inflammation and bronchoconstriction in the lower respiratory tract. If the MMAD of the aerosol is smaller than about 1 μm, then a large percentage of the particles may remain suspended in the inhaled air and may then be exhaled during expiration.

The compounds of the invention may also be administered by transbronchoscopic lavage.

Compositions designed for nasal administration include aerosols, solutions, suspensions, sprays, mists and drops. Aerosolable formulations for nasal administration may be formulated in much the same ways as aerosolable formulations for inhalation with the condition that particles of non-respirable size will be preferred in formulations for nasal administration. Typically, particles of about 5 microns in size, up to the size of visible droplets may be employed. Thus, for nasal administration, a particle size in the range of 10-500 μm may be used to ensure retention in the nasal cavity.

In another aspect, the invention provides a method for treating a respiratory disease in a human in need thereof, comprising administering to the human a pharmaceutical composition comprising a compound of the invention, wherein the compound is administered in an effective amount. In one preferred embodiment, the method comprises administering the pharmaceutical composition as an inhalable composition comprising from about 20 to about 1000 μg of a compound of the invention.

In another aspect, the invention provides a method of treating any one of: a disease associated with reversible or irreversible airway obstruction, chronic obstructive pulmonary disease (COPD), asthma, bronchiectasis (including bronchiectasis due to conditions other than cystic fibrosis), acute bronchitis, chronic bronchitis, post-viral cough, cystic fibrosis, emphysema, pneumonia, panbronchiolitis, transplant-associate bronchiolitis, and ventilator-associated tracheobronchitis or preventing ventilator-associated pneumonia, or treating sinusitis in a human in need thereof, comprising administering to the human a pharmaceutical composition comprising a compound of the invention, wherein the compound is administered in an effective amount. In one preferred embodiment, the method comprises administering the pharmaceutical composition as an inhalable composition comprising from about 20 to about 1000 micrograms of a compound of the invention.

Preferred unit dosage formulations for the compounds of the invention are those containing an effective amount of the active ingredient or an appropriate fraction thereof.

It should be understood that in addition to the ingredients particularly mentioned above, the formulations of this invention may include other agents conventional in the art having regard to the type of formulation in question.

The compositions of the present invention may be formulated for immediate, controlled or sustained release as desired for the particular condition being treated and the desired route of administration. Because the free base of a compound is generally less soluble in aqueous solutions than the salt, compositions comprising a free base of a compound of Formula I may be employed to provide more sustained release of active agent delivered by inhalation to the lungs. An active agent present in the lungs in particulate form which has not dissolved into solution is not available to induce a physiological response, but serves as a depot of bioavailable drug which gradually dissolves into solution. As another example, a formulation may employ both a free base and salt form of a compound of the invention to provide both immediate release and sustained release of the active ingredient for dissolution into the mucus secretions of, for example, the nose.

Combinations

The compounds of the invention may be formulated and/or used in combination with other therapeutically active agents. Examples of other therapeutically active agents which may be formulated or used in combination with the compounds of the invention include but are not limited to anti-inflammatory agents, anticholinergic agents, peroxisome proliferator-activated receptor (PPAR) gamma agonists, PPAR delta agonists, epithelial sodium channel blockers (ENaC blockers), kinase inhibitors (e.g. p38 MAPK, PI3K, JNK, ERK, IKK2), anti-infective agents, and antihistamines.

The present invention thus provides, as another aspect, a composition comprising an effective amount of a compound of the invention and one or more other therapeutically active agents selected from anti-inflammatory agents, anticholinergic agents, P2Y2 receptor agonists, PPAR gamma agonists, PPAR delta agonists, ENaC blockers, kinase inhibitors (e.g. p38 MAPK, PI3K, JNK, ERK, IKK2), antiinfective agents, and antihistamines. Use of the compounds of the invention in combination with one or more other therapeutically active agents may lower the dose of the compound of the invention that is required to treat the respiratory disease, thereby reducing the potential for undesired side-effects attributable to systemically absorbed beta agonists.

Suitable anti-inflammatory agents for use in combination with the compounds of the invention include corticosteroids and non-steroidal anti-inflammatory drugs (NSAIDs), particularly phosphodiesterase (PDE) inhibitors. Examples of corticosteroids for use in the present invention include oral or inhaled corticosteroids or prodrugs thereof. Specific examples include but are not limited to ciclesonide, desisobutyryl-ciclesonide, budesonide, flunisolide, mometasone and esters thereof (e.g., mometasone furoate), fluticasone propionate, fluticasone furoate, beclomethasone, methyl prednisolone, prednisolone, dexamethasone, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-1,6-hydroxy-16α-methyl-3-oxo-17α-propionyloxy-androsta-1,4-diene-17β-carbothioic acid S-(2- oxo-tetrahydro-furan-3S-yl) ester, beclomethasone esters (e.g., the 17-propionate ester or the 17,21-dipropionate ester, fluoromethyl ester, triamcinolone acetonide, rofleponide, or any combination or subset thereof. Preferred corticosteroids for formulation or use in combination with the compounds of the invention are selected from ciclesonide, desisobutyryl-ciclesonide, budesonide, mometasone, fluticasone propionate, and fluticasone furoate, or any combination or subset thereof.

NSAIDs for use in the present invention include but are not limited to sodium cromoglycate, nedocromil sodium, phosphodiesterase (PDE) inhibitors (e.g., theophylline, aminophylline, PDE4 inhibitors, mixed PDE3/PDE4 inhibitors or mixed PDE4/PDE7 inhibitors), leukotriene antagonists, inhibitors of leukotriene synthesis (e.g., 5 LO and FLAP inhibitors), nitric oxide synthase (iNOS) inhibitors, protease inhibitors (e.g., tryptase inhibitors, neutrophil elastase inhibitors, and metalloprotease inhibitors) β2-integrin antagonists and adenosine receptor agonists or antagonists (e.g., adenosine 2a agonists), cytokine antagonists (e.g., chemokine antagonists) or inhibitors of cytokine synthesis (e.g., prostaglandin D2 (CRTh2) receptor antagonists).

The PDE4 inhibitor, mixed PDE3/PDE4 inhibitor or mixed PDE4/PDE7 inhibitor may be any compound that is known to inhibit the PDE4 enzyme or which is discovered to act as a PDE4 inhibitor, and which are selective PDE4 inhibitors (i.e., compounds which do not appreciably inhibit other members of the PDE family). Examples of specific PDE4 inhibitors for formulation and use in combination with the compounds of the present invention include but are not limited to roflumilast, pumafentrine, arofylline, cilomilast, tofimilast, oglemilast, tolafentrine, piclamilast, ibudilast, apremilast, 2-[4-[6,7-diethoxy-2,3-bis(hydroxymethyl)-1-naphthalenyl]-2-pyridinyl]-4-(3-pyridinyl)-1(2H)-phthalazinone (T2585), N-(3,5-dichloro-4-pyridinyl)-1-[(4-fluorophenyl)methyl]-5-hydroxy-α-oxo-1H-indole-3-acetamide (AWD-12-281, 4-[(2R)-2-[3-(cyclopentyloxy)-4-methoxyphenyl]-2-phenylethyl]-pyridine (CDP-840), 2-[4-[[[[2-(1,3-benzodioxol-5-yloxy)-3-pyridinyl]carbonyl]amino]methyl]-3-fluorophenoxy]-(2R)-propanoic acid (CP-671305), N-(4,6-dimethyl-2-pyrimidinyl)-4-[4,5,6,7-tetrahydro-2-(4-methoxy-3-methylphenyl)-5-(4-methyl-1-piperazinyl)-1H-indol-1-yl]benzenesulfonamide, (2E)-2-butenedioate (YM-393059), 9-[(2-fluorophenyl)methyl]-N-methyl-2-(trifluoromethyl)-9H-purin-6-amine (NCS-613), N-(2,5-dichloro-3-pyridinyl)-8-methoxy-5-quinolinecarboxamide (D-4418), N-[(3R)-9-amino-3,4,6,7-tetrahydro-4-oxo-1-phenylpyrrolo[3,2,1-][1,4]benzo-diazepin-3-yl]-3H-purin-6-amine (PD-168787), 3-[[3-(cyclopentyloxy)-4-methoxyphenyl]methyl]-N-ethyl-8-(1-methylethyl)-3H-purin-6-amine hydrochloride (V-11294A), N-(3,5-dichloro-1-oxido-4-pyridinyl)-8-methoxy-2-(trifluoromethyl)-5-quinolinecarboxamide (Sch351591), 5-[3-(cyclopentyloxy)-4-methoxyphenyl]-3-[(3-methylphenyl)methyl]-(3S,5S)-2-piperidinone (HT-0712), 5-[2-[(1R,4R)-4-amino-1-(3-(cyclopentyloxy)-4-methyoxyphenyl]cyclohexyl]ethynyl]pyrimidine-2-amine, 6-[3-(dimethylcarbamoyl)phenylsulfonyl]-4-(3-methoxyphenylamino)-8-methylquinoline-3-carboxamide (GSK-256066), cis-[4-cyano-4-(3-cyclopropylmethoxy-4-difluoromethoxyphenyl)cyclohexan-1-ol], and 4-[6,7-diethoxy-2,3-bis(hydroxymethyl)-1-naphthalenyl]-1-(2-methoxyethyl)-2 (1H)-pyridinone (T-440), and any combination or subset thereof.

Leukotriene antagonists and inhibitors of leukotriene synthesis include zafirlukast, montelukast sodium, zileuton, and pranlukast.

Anticholinergic agents for formulation or use in combination with the compounds of the invention include but are not limited to muscarinic receptor antagonists, particularly including pan antagonists and antagonists of the $M_3$ receptors. Exemplary compounds include the alkaloids of the belladonna plants, such as atropine, scopolamine, homatropine, hyoscyamine, and the various forms including salts thereof (e.g., anhydrous atropine, atropine sulfate, atropine oxide or HCl, methylatropine nitrate, homatropine hydrobromide, homatropine methyl bromide, hyoscyamine hydrobromide, hyoscyamine sulfate, scopolamine hydrobromide, scopolamine methyl bromide), or any combination or subset thereof.

Additional anticholinergics for formulation and use in combination with the methantheline, propantheline bromide, anisotropine methyl bromide or Valpin 50, aclidinium bromide, glycopyrrolate (Robinul), isopropamide iodide, mepenzolate bromide, tridihexyl chloride, hexocyclium methylsulfate, cyclopentolate HCl, tropicamide, trihexyphenidyl CCl, pirenzepine, telenzepine, and methoctramine, or any combination or subset thereof.

Preferred anticholinergics for formulation and use in combination with the compounds of the invention include ipratropium (bromide), oxitropium (bromide) and tiotropium (bromide), or any combination or subset thereof.

Examples of ENaC receptor blockers for formulation and use in combination with the compounds of the invention include but are not limited to amiloride and derivatives thereof such as those compounds described in U.S. Pat. No. 6,858,615, and PCT Publication Nos. WO2003/070182, WO2004/073629, WO2005/018644, WO2006/022935, WO2007/018640, and WO2007/146869, all to Parion Sciences, Inc.

Examples of kinase inhibitors include inhibitors of NFkB, PI3K (phosphatidylinositol 3-kinase) (CAL-263 (oral), Trial trove and Calistoga web site), p38-MAP kinase (SB-681323 (oral); Singh et al., *J Clin Pharmacol.* 2010 January; 50(1): 94-100).

Antiinfective agents for formulation and use in combination with the compounds of the invention include antivirals and antibiotics. Examples of suitable antivirals include Tamiflu® and Relenza®. Examples of suitable antibiotics include but are not limited to aztreonam (arginine or lysine), fosfomycin, and aminoglycosides such as tobramycin, or any combination or subset thereof.

Antihistamines (i.e., H1-receptor antagonists) for formulation and use in combination with the compounds of the invention include but are not limited to:

ethanolamines such as diphenhydramine HCl, carbinoxamine maleate, doxylamine, clemastine fumarate and dimenhydrinate;

ethylenediamines such as pyrilamine maleate (metpyramine), tripelennamine HCl, tripelennamine citrate, and antazoline;

alkylamines such as pheniramine, chlorpheniramine, bromopheniramine, dexchlorpheniramine, triprolidine and acrivastine;

pyridines such as methapyrilene, piperazines such as hydroxyzine HCl, hydroxyzine pamoate, cyclizine HCl, cyclizine lactate, meclizine HCl and cetirizine HCl;

piperidines such as astemisole, levocabastine HCl, loratadine, descarboethoxy loratadine, terfenadine, and fexofenadine HCl;

tri- and tetracyclics such as promethazine, chlorpromethazine trimeprazine and azatadine; and azelastine HCl, or any combination or subset thereof.

In the above-described methods of treatment and uses, a compound of the invention may be employed alone, or in combination with one or more other therapeutically active agents. Typically, any therapeutically active agent that has a therapeutic effect in the disease or condition being treated with the compound of the invention may be utilized in combination with the compounds of the invention, provided that the particular therapeutically active agent is compatible with therapy employing a compound of the invention. Typical therapeutically active agents which are suitable for use in combination with the compounds of the invention include agents described above.

In one preferred embodiment, the compounds of the invention are used in combination with one or more anti-inflammatory agents, particularly PDE4i or an inhaled corticosteroid. In one preferred embodiment, the compounds of the invention are used in combination with one or more anticholinergics, particularly muscarinic (M3) receptor antagonists.

In another aspect, the invention provides methods for treatment and uses as described above, which comprise administering an effective amount of a compound of the invention and at least one other therapeutically active agent. The compounds of the invention and at least one additional therapeutically active agent may be employed in combination concomitantly or sequentially in any therapeutically appropriate combination. The administration of a compound of the invention with one or more other therapeutically active agents may be by administration concomitantly in 1) a unitary pharmaceutical composition, such as the compositions described above, or 2) separate pharmaceutical compositions each including one or more of the component active ingredients. The components of the combination may be administered separately in a sequential manner wherein the compound of the invention is administered first and the other therapeutically active agent is administered second or vice versa.

When a compound of the invention is used in combination with another therapeutically active agent, the dose of each compound may differ from that when the compound of the invention is used alone. Appropriate doses will be readily determined by one of ordinary skill in the art. The appropriate dose of the compound of the invention, the other therapeutically active agent(s) and the relative timings of administration will be selected in order to achieve the desired combined therapeutic effect, and are within the expertise and discretion of the attendant physician, clinician or veterinarian.

Synthetic Processes

The present invention also provides processes for preparing the compounds of the invention and to the synthetic intermediates useful in such processes, as described in detail below.

Certain abbreviations and acronyms are used in describing the synthetic processes and experimental details. Although most of these would be understood by one skilled in the art, the following table contains a list of many of these abbreviations and acronyms.

| Abbreviation | Meaning |
| --- | --- |
| AIBN | azobisisobutyronitrile |
| Bn | benzyl |
| Boc | tert-butoxycarbonyl |
| (Boc)$_2$O | di-tert-butyldicarbonate |
| BOP | benzotriazole-1-yl-oxy-tris-(dimethylamino)-phosphonium hexafluorophosphate |
| Cbz | Carbobenzyloxy |
| DCC | N,N'-dicyclohexylcarbodiimide |
| DCE | dichloroethane |
| DCM | dichloromethane |
| DIEA | N,N-diisopropylethylamine |
| DME | dimethoxyethane |
| DMF | dimethylformamide |
| DMSO | dimethylsulfoxide |
| Et | ethyl |
| EtOAc | ethyl acetate |
| EtOH | ethanol |
| Et$_3$N and TEA | triethylamine |
| ESI | electrospray ionization |
| g | gram(s) |
| h | hour(s) |
| H$_2$ | hydrogen gas |
| HATU | 2-(1H-7-Azabenzotriazol-1-yl)-1,1,3,3-tetramethyl uronium hexafluorophosphate |
| HPLC | High performance liquid chromatography |
| iPrOH | Isopropyl alcohol |
| LAH | lithium aluminum hydride |
| M | Molar |
| mg | milligram(s) |
| Me | methyl |
| MeOH | methanol |
| m/z or m/e | mass to charge ratio |
| MH$^+$ | mass plus 1 |
| MH$^-$ | mass minus 1 |
| MIC | minimal inhibitory concentration |
| min | minute(s) |
| mL | milliliter(s) |
| mmol | millimole(s) |
| MS or ms | mass spectrum |
| MsCl | methanesulfonyl chloride, mesyl chloride |
| Ms | methanesulfonate; mesylate |
| N | Normal |
| NaBH(OAc)$_3$ | sodium triacetoxy borohydride |
| NaCNBH$_3$ | sodium cyanoborohydride |
| NaN$_3$ | sodium azide |
| PDC | Pyridinium dichromate |
| Pd(OH)$_2$/C | Palladium hydroxide on carbon |
| Ph | phenyl |
| PMP | 1,2,2,6,6-pentamethylpiperidine |
| PPh$_3$ | triphenylphosphine |
| PtO$_2$ | Platinum oxide |
| Py | Pyridyl or pyridine |
| rt or r.t. | room temperature (aka ambient temperature) |
| t-Bu | tert-butyl |
| TBAF | tetrabutylammoniumfluoride |
| TBS | tert-butyldimethylsilyl |
| TBSCl | tert-butyldimethyisilyl chloride |
| TFA | trifluoroacetic acid |
| THF | tetrahydrofuran |
| TLC or tlc | thin layer chromatography |
| δ | parts per million down field from tetramethylsilane |

In the following synthetic processes, it may be desirable for the preparation of certain compounds of the invention to install protecting groups on reactive sites of the intermediate. One skilled in the art will readily be able to determine the desirability of using protecting groups, suitable protecting groups to employ based on the compounds and reaction conditions and methods for the installation and removal of such protecting groups. Suitable protecting groups include TBS, Bn, and Boc. Conventional techniques for installing and removing such protecting groups may be employed in the instant reaction as well.

A general procedure to prepare compounds of the invention is shown in Scheme 1 below.

Scheme 1

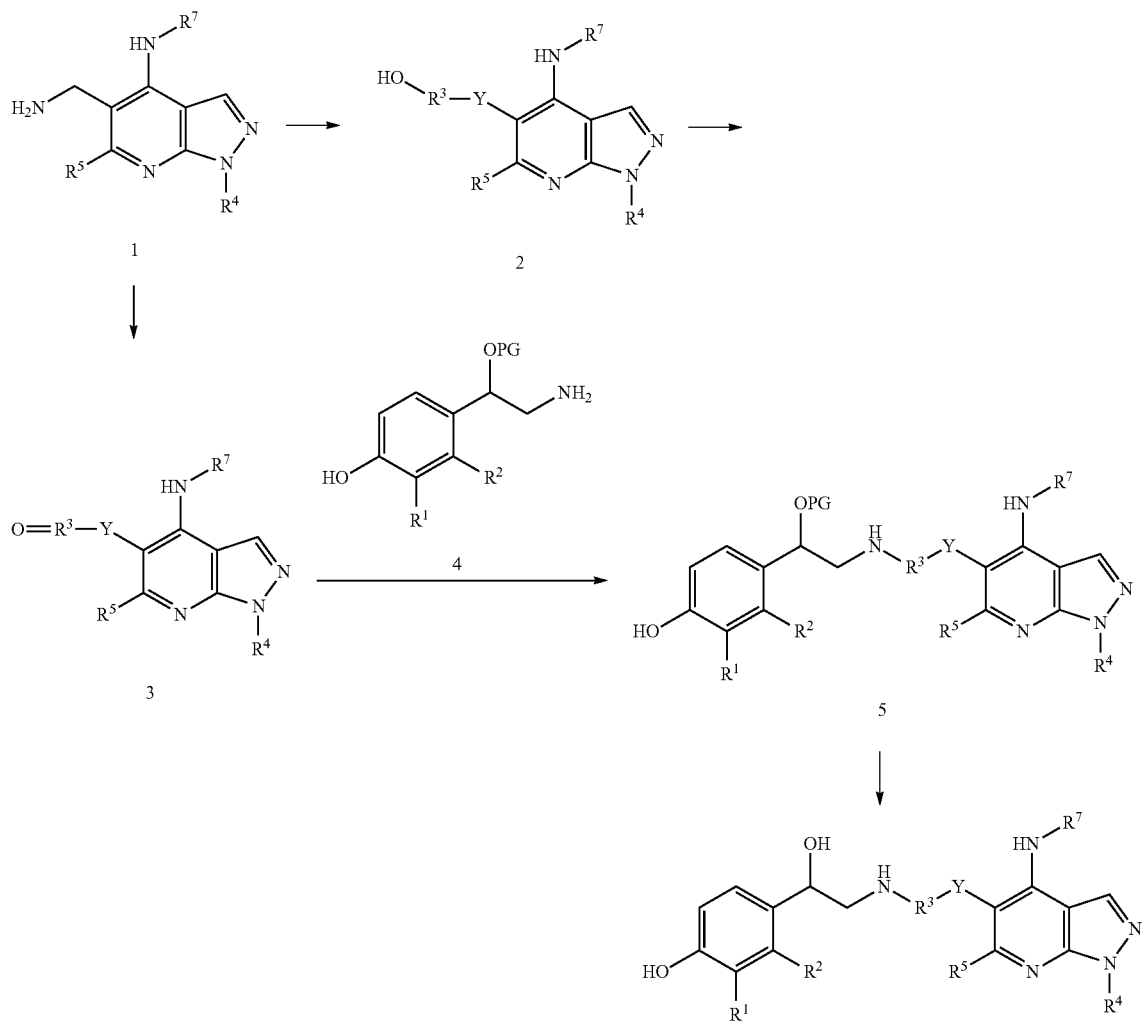

wherein:
Y is C(O), C(O)NHCH$_2$, N(R$^7$)C(O)NHCH$_2$, OC(O)NHCH$_2$, or SO$_2$NHCH$_2$;
PG is a suitable protecting group, such as H or TBS;
and all other variables are as defined above.

Generally, one process for preparing compounds of the invention comprises the steps of
a) reductive alkylation of a compound 3 or a salt thereof with a compound 4 or a salt thereof to prepare compound 5 or a salt thereof; and
b) optionally deprotecting the compound 5 or a salt thereof, to prepare a compound of Formula I or a salt thereof.

Coupling of compound 1 with an acid under standard conditions, such as for example, HATU couplings, mixed anhydrides, DCC couplings, and the like, gives the amide compound 2. Coupling of Compound 1 with a phosgene equivalent, such as carbonyldiimidazole or 4-nitrophenylochloroformate at low temperature, between −78° C. and 0° C., gives an activated species, which can be subsequently reacted with an appropriately substituted alcohol or amine at higher temperature, between rt and 100° C., to give compound 2 with a carbamate or urea respectively. Compound 1 is known in the literature. Compound 2 is oxidized under standard conditions (Dess-Martin, PDC, Swern) to give the corresponding carbonyl compound 3. Alternatively, compound 3 may be formed directly from compound 1 under standard conditions, such as for example, HATU coupling, mixed anhydride, DCC coupling, and the like, if the appropriately substituted carbonyl containing acid is available. Alternatively, compounds 2 or 3 may be formed directly if the appropriately substituted acid chloride or sulfonyl chloride is available.

Compound 4, which is known in the literature, is coupled with compound 3 under reductive alkylation conditions, such as NaCNBH$_3$ or NaBH(OAc)$_3$, in an appropriate solvent, such as an alcohol or DMF, to give the corresponding compound 5. Compound 5 is converted to the compounds of the invention by removal of any protecting group. A TBS protecting group was often used and in those cases, deprotection was accomplished using conventional techniques, such as deprotection with TBAF.

In another embodiment, compounds of the invention may be prepared by displacement of a leaving group as shown in Scheme 2.

Scheme 2

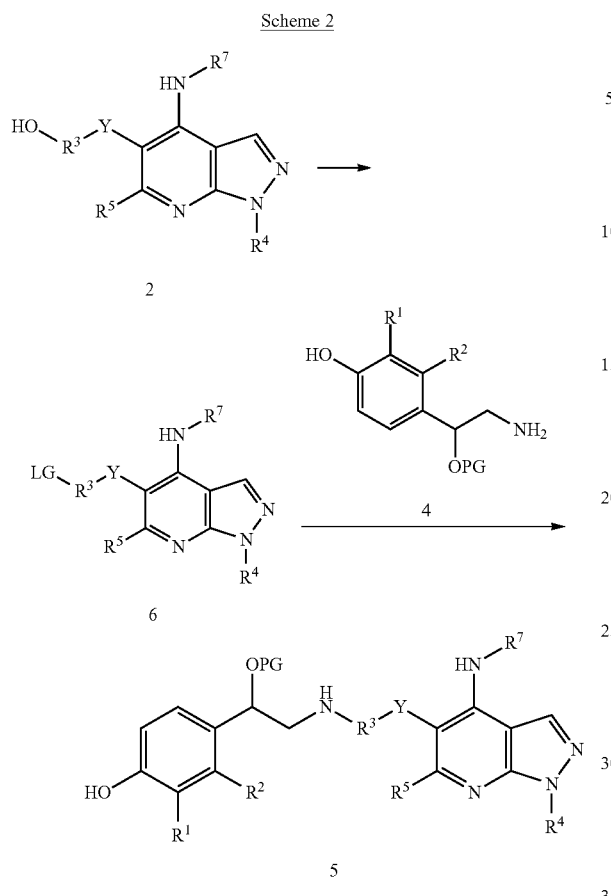

Scheme 3

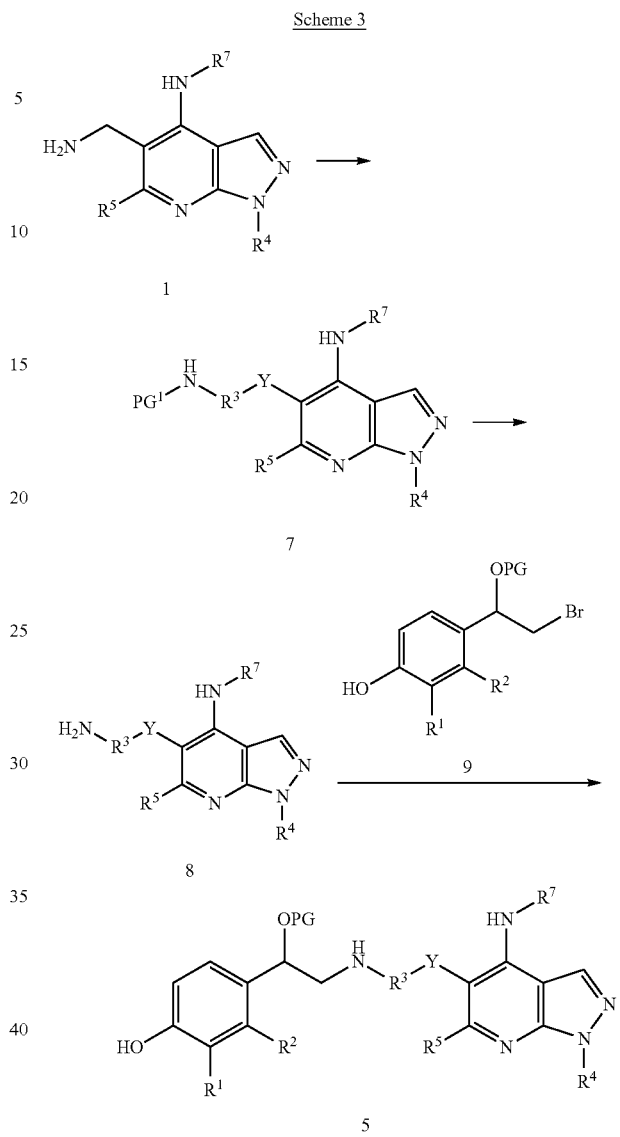

wherein:
Y is C(O)NHCH$_2$, N(R$^8$)C(O)NHCH$_2$, OC(O)NHCH$_2$, or SO$_2$NHCH$_2$;
PG is a suitable protecting group, such as H or TBS;
LG is a suitable leaving group such as bromide, chloride, iodide, OMs, or O-triflate;
and all other variables are as defined above.

Generally, this process for preparing compounds of the invention comprises the steps of
a) coupling a compound 6 or a salt thereof with a compound 4 or a salt thereof by alkylation to prepare a compound 5 or a salt thereof; and
b) optionally deprotecting the compound 5 or a salt thereof, to prepare a compound of Formula I or a salt thereof.

More specifically, according to this embodiment, the alcohol in compound 2 may be converted to a suitable leaving group under standard conditions to give compound 6. For example, conversion of the alcohol of compound 2 to a mesylate may occur through treatment of compound 2 with MsCl and an appropriate base, such as TEA or pyridine, in an appropriate solvent such as CH$_2$Cl$_2$ at rt. Alternatively, conversion of the alcohol of compound 2 to a bromide may occur under standard conditions such as CBr$_4$ and PPh$_3$. Alternatively, compound 6 may be formed directly under standard conditions, by coupling compound 1 with the appropriately substituted acid that contains a leaving group. Compound 6 is then coupled with compound 4 at elevated temperatures, such as about 50 to about 150° C., in an appropriate solvent such as DMSO or DMF with an appropriate base, such as K$_2$CO$_3$, DIEA, or PMP, to give compound 5. Compound 5 may then be deprotected to provide compounds of Formula I as described above in Scheme 1.

wherein:
Y is C(O)NHCH$_2$, N(R$^8$)C(O)NHCH$_2$, OC(O)NHCH$_2$, or SO$_2$NHCH$_2$;
PG is a suitable protecting group, such as H or TBS;
PG$^1$ is a suitable protecting group such as Cbz or Boc;
and all other variables are as defined above.

Generally, this process for preparing compounds of the invention comprises the steps of
a) coupling a compound 8 or a salt thereof with a compound 9 or a salt thereof to prepare a compound 5 or a salt thereof; and
b) optionally deprotecting the compound 5 or a salt thereof, to prepare a compound of Formula I or a salt thereof.

Additionally, according to this embodiment, compound 1 may be coupled to an appropriately protected amino acid, which are commercially available or known, to produce compound 7. Appropriate protecting groups include Boc or Cbz. Coupling of Compound 1 with a phosgene equivalent, such as carbonyldiimidazole or 4-nitrophenylochloroformate at low temperature, between −78° C. and 0° C., gives an activated species, which can be subsequently reacted with an appropriately substituted alcohol or amine at higher temperature, between rt and 100° C., to give compound 7 as a carbamate or urea respectively. Alternatively, compounds 7 may be formed directly if the appropriately substituted acid chloride or sulfonyl chloride is available. The protecting group may be removed under standard conditions to give compound 8. Reaction of compound 8 with the bromide compound 9 at elevated temperatures, such as about 50 to about 150° C., neat or in an appropriate solvent such as DMSO or DMF, produces compound 5.

Intermediate compounds of formula 7 wherein Y is $N(R^8)C(O)$ may be prepared from the corresponding compound 10 according to the following Scheme 4. These intermediate compounds 7 may then be used as described above to prepare compounds of Formula I wherein Y is $N(R^8)C(O)$.

Scheme 4

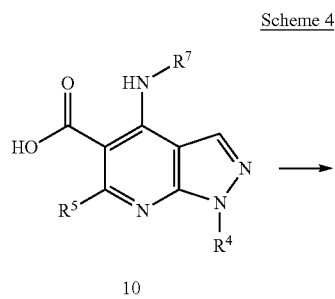

10

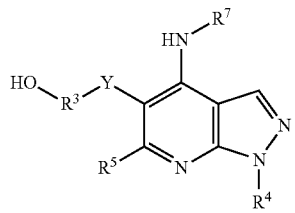

2 wherein:

Y is $C(O)$ or $N(R^8)C(O)$;

and all other variables are as defined above.

Coupling of compound 10 with an amino-alcohol under standard conditions, such as for example, HATU couplings, mixed anhydrides, DCC couplings, and the like, gives the amide compound 2.

The order of steps in the foregoing reactions is not critical to the practice of the present invention and the steps may be carried out in any suitable order according to the knowledge of those skilled in the art, to provide the compounds of formula I.

The foregoing detailed description may be further understood from the following examples, which are presented for the purposes of illustration only and are not intended to limit the scope of the invention. The invention is defined solely by the claims which follow. In the following examples, compounds are named using standard IUPAC naming principles where possible. The naming convention employed for the novel compounds are exemplified by Examples below.

7 wherein:

Y is $N(R^8)C(O)$;

$PG^1$ is a suitable protecting group such as Cbz or Boc; and all other variables are as defined above.

Coupling of compound 10 with an monoprotected diamine under standard conditions, such as for example, HATU couplings, mixed anhydrides, DCC couplings, and the like, gives the amide compound 7. Compound 10 is known in the literature.

Compound 10 may also be used to prepare compound 2 wherein Y is $N(R^8)C(O)$ as shown in Scheme 5 below.

Scheme 5

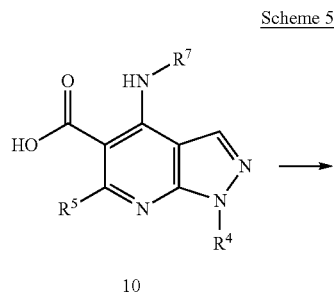

10

EXAMPLES

Intermediate 1: (R)-5-[2-Azido-1-[(tert-butyldimethylsilyl)oxy]ethyl]-8-(benzyloxy)quinolin-2(1H)-one

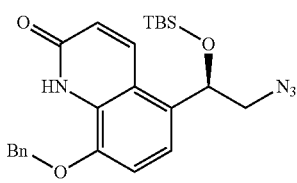

NaN$_3$ (266 mg, 4.1 mmol) was added to a stirred solution of (R)-8-(benzyloxy)-5-[2-bromo-1-[(tert-butyldimethylsilyl)oxy]ethyl]quinolin-2(1H)-one (1 g, 2.05 mmol) in DMF (20 mL) at rt and warmed to 80° C. for 3 h. The resulting solution was poured into H$_2$O (80 mL) and extracted with EtOAc (3×50 mL). The combined organic layers were washed with H$_2$O (2×100 mL), brine (100 mL), dried over Na$_2$SO$_4$ (s), and concentrated to give the title compound (1.37 g) as a yellow solid. The compound was used with no further purification. ES/MS calcd. for C$_{24}$H$_{31}$N$_4$O$_3$Si$^+$ 451.2. found m/z=451.3 (M+H)$^+$.

Intermediate 2: (R)-5-[2-Amino-1-[(tert-butyldimethylsilyl)oxy]ethyl]-8-hydroxyquinolin-2(1H)-one

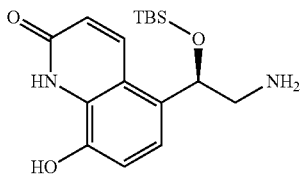

Intermediate 1 (1.37 g) was dissolved in MeOH (20 mL) and Pd(OH)$_2$/C (20% w/w, 288 mg, 0.41 mmol) was added. Nitrogen gas was bubbled through the solution for 5 min. The resulting suspension was attached to a balloon filled with H$_2$ and stirred over night. The reaction mixture was filtered through celite and concentrated to give a brown oil (1.208 g). Chromatography (9:1, CH$_2$Cl$_2$/MeOH, 0.1% Et$_3$N) afforded the title compound (597 mg, 87% 2 steps) as a light yellow solid. ES/MS calcd. for C$_{17}$H$_{27}$N$_2$O$_3$Si$^+$ 335.2. found m/z=335.2 (M+H)$^+$.

Intermediate 3: (R)-5-(2-Azido-1-hydroxyethyl)-8-(benzyloxy)quinolin-2(1H)-one

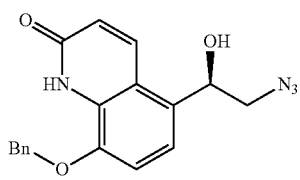 [SMILES: [N-]=[N+]=NC[C@H](O)c1ccc(OCc2ccccc2)c2[nH]c(=O)ccc12]

TBAF (1.0 M in THF, 0.443 mL, 0.443 mmol) was added to a stirring solution of Intermediate 1 (200 mg, 0.443 mmol) in THF (4 mL) at rt. The resulting mixture was stirred over night then concentrated. Chromatography (1:3, Hexanes/EtOAc) afforded the title compound (137 mg, 92%) as an off-white solid. ES/MS calcd. for C$_{18}$H$_{17}$N$_4$O$_3$$^+$ 337.1. found m/z=337.2 (M+H)$^+$.

Intermediate 4: (R)-5-(2-Amino-1-hydroxyethyl)-8-hydroxyquinolin-2(1H)-one

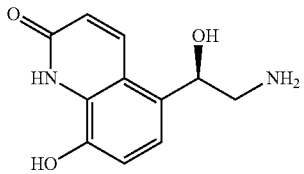 [SMILES: NC[C@H](O)c1ccc(O)c2[nH]c(=O)ccc12]

The title compound was synthesized in a manner analogous to that described for Intermediate 2, using Intermediate 3 as a substrate. ES/MS calcd. for C$_{11}$H$_{13}$N$_2$O$_3$$^+$ 221.1. found m/z=221.1 (M+H)$^+$.

Intermediate 5: (R)-1-[4-(Benzyloxy)-3-[[(tert-butyldimethylsilyl)oxy]methyl]phenyl]-2-bromoethanol

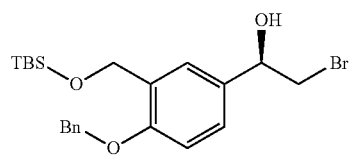

TBSCl (5 g, 33.2 mmol) and imidazole (3.7 g, 55.4 mmol) were added to a stirring solution of (R)-4-(2-bromo-1-hydroxyethyl)-2-(hydroxymethyl)phenol (10 g, 27.7 mmol) in CH$_2$Cl$_2$ (200 mL) at rt. The resulting suspension was stirred for 1 h then quenched with H$_2$O (200 mL). The aqueous layer was extracted with CH$_2$Cl$_2$ (3×100 mL). The combined organic layer was washed with brine (300 mL), dried over Na$_2$SO$_4$ (s), and concentrated to give title compound (13.9 g) as a clear oil. The compound was used with no further purification. ES/MS calcd. for C$_{22}$H$_{31}$BrNaO$_3$Si$^+$ 473.1. found m/z=473.1 (M+Na)$^+$.

Intermediate 6: (R)-[1-[4-(Benzyloxy)-3-[[(tert-butyldimethylsilyl)oxy]methyl]phenyl]-2-bromoethoxy](tert-butyl)dimethylsilane

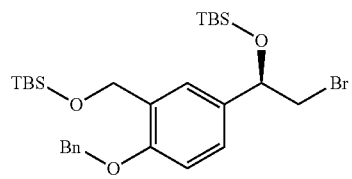

The title compound was synthesized in a manner analogous to that described for Intermediate 5. Excess TBSCl and a higher reaction temperature were used.

Intermediate 7: (R)-2-Azido-1-[4-(benzyloxy)-3-[[(tert-butyldimethylsilyl)oxy]methyl]phenyl]ethanol

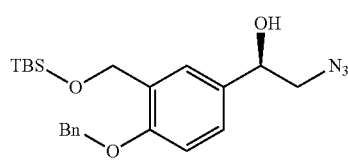

The title compound was synthesized in a manner analogous to that described for Intermediate 1, using Intermediate 5 in place of (R)-8-(benzyloxy)-5-[2-bromo-1-[(tert-butyldimethylsilyl)oxy]ethyl]quinolin-2(1H)-one. ES/MS calcd. for C$_{22}$H$_{31}$N$_3$NaO$_3$Si$^+$ 436.2. found m/z=436.2 (M+Na)$^+$.

Intermediate 8: (R)-4-(2-Amino-1-hydroxyethyl)-2-[[(tert-butyldimethylsilyl)oxy]methyl]phenol

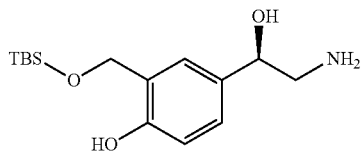

The title compound was synthesized in a manner analogous to that described in Intermediate 2, using Intermediate 7 as a substrate. ES/MS calcd. for $C_{15}H_{27}NNaO_3Si^+$ 320.2. found m/z=320.2 (M+Na)$^+$.

Intermediate 9: (R)—N-[2-(Benzyloxy)-5-(2-bromo-1-hydroxyethyl)phenyl]formamide

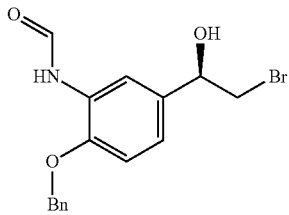 [SMILES: O=CNc1cc([C@@H](O)CBr)ccc1OCc1ccccc1]

(R)-1-[4-(Benzyloxy)-3-nitrophenyl]-2-bromoethanol (0.2 g, 5.7 mmol) in THF:toluene (1:1, 5 mL) was reacted with PtO$_2$ (1% w/w) on a Parr shaker at 45 psi at rt overnight. The next morning the PtO$_2$ was removed by filtration over celite. The filtered solution was cooled to 0° C. and a solution of acetic anhydride (0.161 mL, 0.569 mmol) and formic acid (0.043 mL, 1.140 mmol) was added dropwise to a mixing solution of the aniline. The reaction was allowed to proceed at 0° C. for 30 min then warmed to rt and reacted for another 2 h. The reaction mixture was concentrated to near dryness then water was added. The aqueous layer was extracted with EtOAc (3×25 mL). The combined organic layers were washed with NaHCO$_3$, brine, dried over Na$_2$SO$_4$ (s), and concentrated to give a residue. Chromatography (1:1 Hexanes/EtOAc) gives the title compound (156 mg, 78% 2 steps). ES/MS calcd. $C_{16}H_{17}BrNO_3^+$ 350.0. found m/z=350 (M+H)$^+$.

Intermediate 10: (R)—N-[5-(2-Azido-1-hydroxyethyl)-2-(benzyloxy)phenyl]formamide

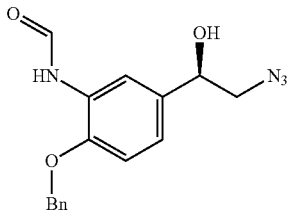 [SMILES: [N-]=[N+]=NC[C@H](O)c1ccc(OCc2ccccc2)c(NC=O)c1]

The title compound was synthesized in a manner analogous to that described for Intermediate 1, using Intermediate 9 as substrate. ES/MS calcd. $C_{16}H_{17}N_4O_3^+$ 313.1. found m/z=313 (M+H)$^+$.

Intermediate 11: (R)—N-[5-[2-Azido-1-[(tert-butyldimethylsilyl)oxy]ethyl]-2-(benzyloxy)phenyl]formamide

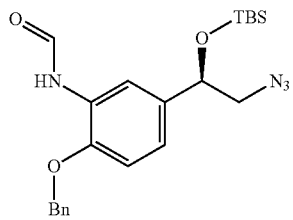

The title compound was synthesized in a manner analogous to that described for Intermediate 5, using Intermediate 10 in place of (R)-4-(2-bromo-1-hydroxyethyl)-2-(hydroxymethyl)phenol. ES/MS calcd. $C_{22}H_{31}N_4O_3Si^+$ 427.2. found m/z=427 (M+H)$^+$.

Intermediate 12: (R)—N-[5-[2-Amino-1-[(tert-butyldimethylsilyl)oxy]ethyl]-2-hydroxyphenyl]formamide

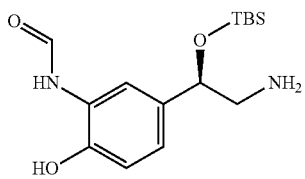

The title compound was synthesized in a manner analogous to that described for Intermediate 2, using Intermediate 11 in place of Intermediate 1. ES/MS calcd. $C_{15}H_{27}N_2O_3Si^+$ 311.2. found m/z=311 (M+H)$^+$ Intermediate 13: (R)-1-[3-Amino-4-(benzyloxy)phenyl]-2-bromoethanol

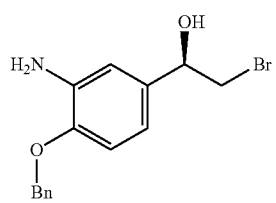

(R)-1-[4-(benzyloxy)-3-nitrophenyl]-2-bromoethanol (0.200 g, 0.569 mmol) in 1:1 THF:toluene (5 mL) was reacted with 1% (w/w) PtO$_2$ on a Parr shaker at 45 psi at rt overnight. The next morning the PtO$_2$ was removed by filtration over celite. The product was concentrated to give the title compound. ES/MS calcd. for $C_{15}H_{17}BrNO_2^+$ 322.0. found m/z=322 (M+H)$^+$.

Intermediate 14: (R)-1-[3-Amino-4-(benzyloxy)phenyl]-2-azidoethanol

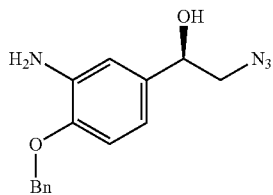 [SMILES: [N-]=[N+]=NC[C@H](O)c1ccc(OCc2ccccc2)c(N)c1]

The title compound was synthesized in a manner analogous to that described for Intermediate 1, using Intermediate 13 in place of (R)-8-(benzyloxy)-5-[2-bromo-1-[(tert-butyldimethylsilyl)oxy]ethyl]quinolin-2(1H)-one. ES/MS calcd. for $C_{15}H_{17}N_4O_2^+$ 285.1. found m/z=285 (M+H)$^+$.

Intermediate 15: of (R)-8-(Benzyloxy)-5-[2-bromo-1-[(tert-butyldimethylsilyl)oxy]ethyl]quinolin-2(1H)-one

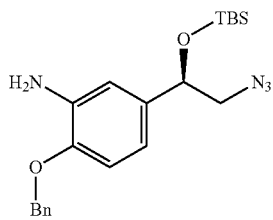

The title compound was synthesized in a manner analogous to that described for intermediate 5, using Intermediate 14 in place of (R)-4-(2-bromo-1-hydroxyethyl)-2-(hydroxymethyl)phenol. ES/MS calcd. for $C_{21}H_{31}N_4O_2Si^+$ 399.2. found m/z=399 (M+H)$^+$.

Intermediate 16: (R)—N-[5-[2-Azido-1-[(tert-butyldimethylsilyl)oxy]ethyl]-2-(benzyloxy)phenyl]methanesulfonamide

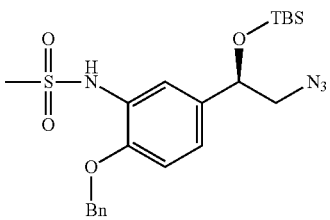

Methanesulfonyl chloride (0.044 mL, 0.569 mmol) was added to a stirring solution of Intermediate 15 (275 mg, 0.569 mmol) in pyridine (10 mL) at 0° C. The resulting mixture was warmed to rt and monitored for completeness by LC/MS. An additional 1 equivalent of MsCl was added after 1 h followed by an additional 0.5 equivalent after another hour for a total of 2.5 equivalents. After an additional 1 h, H$_2$O (50 mL) was added and stirred at rt for 2 h. The reaction was extracted with CH$_2$Cl$_2$ (4×25 mL). The combined organic layers were washed with said. NaHCO$_3$, brine, dried over Na$_2$SO$_4$ (s), and concentrated. Chromatography (1:1 Hexanes/EtOAc) afforded the title compound (197 mg, 72%, 3 steps). ES/MS calcd. for $C_{22}H_{33}N_4O_4SSi^+$ 477.2. found m/z=477 (M+H)$^+$ Intermediate 17: (R)—N-[5-[2-Amino-1-[(tert-butyldimethylsilyl)oxy]ethyl]-2-hydroxyphenyl]methanesulfonamide

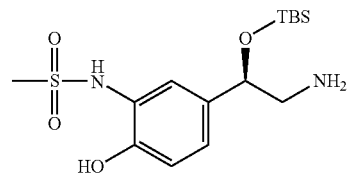

The title compound was synthesized in a manner analogous to that described for Intermediate 2, using Intermediate 16 in place of Intermediate 1. The compound was used with no further purification. ES/MS calcd. for $C_{15}H_{29}N_2O_4SSi^+$ 361.2. found m/z=361 (M+H)$^+$.

Intermediate 18: 3-(2-Hydroxy-2-methylpropyl)benzoic acid

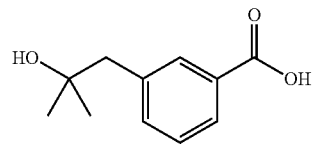

CH$_3$MgBr (3.0 M in THF, 11.2 mL, 33.7 mmol) was added slowly to a stirring solution of 3-(2-oxopropyl)benzoic acid (2 g, 11.2 mmol) in THF (100 mL) at 0° C. The resulting suspension was allowed to warm to rt then stirred overnight. The reaction mixture was diluted with H$_2$O (50 mL) then quenched with 5 N HCl (pH<3). The aqueous layer was extracted with EtOAc (3×50 mL). The combined organic layers were washed with H$_2$O (100 mL), brine (100 mL), dried over Na$_2$SO$_4$ (s), and concentrated to give a yellow oil. Chromatography (9:1, CH$_2$Cl$_2$/MeOH) afforded the title compound (1.36 g, 62%) as a white solid. ES/MS calcd. for $C_{11}H_{14}NaO_3^+$ 217.1. found m/z=217.2 (M+Na)$^+$.

Intermediate 19: methyl 3-(2-Amino-2-methylpropyl)benzoate

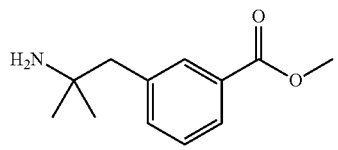

Chloroacetonitrile (0.845 mL, 13.4 mmol) and conc. H$_2$SO$_4$ (3 mL, 55.2 mmol) were added to a stirring solution of Intermediate 18 (1.3 g, 0.69 mmol) in glacial acetic acid (3 mL) at 0° C. The resulting mixture was allowed to warm to rt then stirred for an additional 2 h. The reaction mixture was poured into ice and made basic with $K_2CO_3$ (s) (pH ~4). The aqueous layer was extracted with EtOAc (3×50 mL). The combined organic layers were washed with brine (100 mL), dried over $Na_2SO_4$ (s), and concentrated to give an off white solid. The solid was redissolved in glacial acetic acid (20 mL) and thiourea (904 mg, 11.9 mmol) was added. The reaction mixture was warmed to 95° C. for 3 h, cooled, then concentrated. The residue was dissolved in MeOH (20 mL) and HCl (g) was bubbled through for 5 min. The resulting solution was refluxed overnight, cooled, and then concentrated. The residue was diluted with $Et_2O$ (100 mL) and washed with $H_2O$ (100 mL). The aqueous layer was made basic with satd. $NaHCO_3$ (pH>10) and then extracted with $CHCl_3$ (3×50 mL). The combined organic layers were washed with brine (100 mL), dried over $Na_2SO_4$ (s), and concentrated to the title compound (1.26 g) as a clear oil. The compound was used with no further purification. ES/MS calcd. for $C_{12}H_{18}NO_2^+$ 208.1. found m/z=208.2 (M+H)$^+$.

Intermediate 20: Methyl 4-(5-hydroxypent-1-yn-1-yl)benzoate

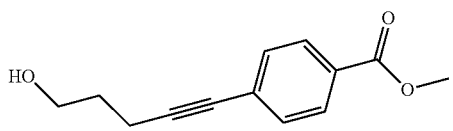 [SMILES: COC(=O)c1ccc(C#CCCCO)cc1]

Methyl 4-iodobenzoate (13.1 g, 60 mmol), $PdCl_2(PPh_3)_2$ (2.0 g, 3 mmol), and CuI (855 mg, 4.5 mmol) were added to TEA (60 mL). The mixture is degassed while stirring by bubbling $N_2$ vigorously into the solution. Pent-4-yn-1-ol (5.5 g, 66 mmol) was added by syringe. The mixture was heated at 90° C. overnight. After cooling, the crude mixture was concentrated by rotary evaporation and pumped on the high vacuum for 1 h. The oil was dissolved in DCM and adsorbed onto Celite followed by purification by chromatography (gradient 10-100% EtOAc/Hexanes) to give the title compound as a light yellow powder (9 g, 69%). $^1$H NMR (400 MHz, $CDCl_3$) δ 7.95 (dd, 2H, J=9.0, 1.5 Hz), 7.44 (dd, 2H, J=9.0, 1.5 Hz), 3.90 (s, 3H), 3.85 (m, 2H), 2.57 (t, 2H, J=5.5 Hz), 1.87 (m, 2H), 1.42 (t, 1H, J=5.5 Hz); ES/MS calcd. for $C_{13}H_{15}O_3^+$ 219.1. found m/z=219 (M+H)$^+$.

Intermediate 21: 4-(5-Hydroxypent-1-yn-1-yl)benzoic acid

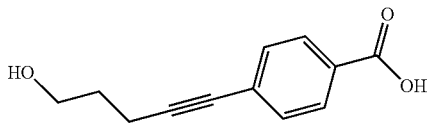 [SMILES: O=C(O)c1ccc(C#CCCCO)cc1]

LiOH (2 g, 83 mmol) in $H_2O$ (30 mL) was added dropwise to a stirring solution of Intermediate 20 (2 g, 9.2 mmol) in THF (30 mL). The resulting mixture was stirred at 42° C. for 4 h. After cooling, water (100 mL) and EtOAc (200 mL) were added. The mixture was extracted with EtOAc. The organic layer and the $H_2O$ layer were independently neutralized with 1N HCl. The aqueous layer was extracted with EtOAc and the combined organic layers dried over $MgSO_4$ (s). The material was concentrated by rotary evaporation and the crude solid was purified by trituration with EtOAc and hexanes to give the title compound as a white powder (1.75 g, 93%). $^1$H NMR (400 MHz, DMSO-$d_6$) δ 13.05 (brs, 1H), 7.88 (dd, 2H, J=8.5, 1.5 Hz), 7.47 (dd, 2H, J=8.5, 1.5 Hz), 4.55 (brs, 1H), 3.50 (t, 2H, J=5.5 Hz), 2.50 (m, 2H), 1.68 (m, 2H); ES/MS calcd. for $C_{12}H_1O_3^+$ 205.1. found m/z=205 (M+H)$^+$.

Intermediate 22: 1-(5-chloropent-1-yn-1-yl)-4-nitrobenzene

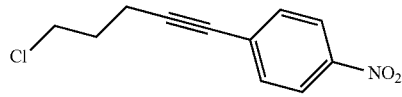

A mixture of 4-iodonitrobenzene (25 g, 100 mmol), dichlorobis(triphenylphosphine)palladium(II) (0.30 g, 0.43 mmol) and copper (I) iodide (0.18 g, 0.95 mmol) in tetrahydrofuran (300 mL) and triethylamine (150 mL) was degassed under Argon for 10 minutes. The mixture was then heated to 55° C. and treated with 5-chloropentyne (12 mL, 110 mmol) via syringe. After 30 minutes of stirring, additional quantities of dichlorobis(triphenylphosphine)palladium(II) (0.10 g) and 5-chloropentyne (1 mL) were added. After another 30 minutes of stirring, the mixture was allowed to cool to room temperature and then was filtered through a pad of Celite diatomaceous earth. The filtrate was concentrated to dryness under reduced pressure to provide 1-(5-chloropent-1-ynyl)-4-nitrobenzene, which was carried on without further purification. ES/MS calcd. for $C_{11}H_{11}ClNO_2^+$ 224.1. found m/z=224.2 (M+1-1)$^+$.

Intermediate 23: 1-(5-bromopent-1-yn-1-yl)-4-nitrobenzene

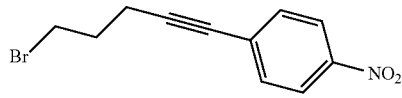 [SMILES: O=[N+]([O-])c1ccc(C#CCCCCl)cc1]

A solution of crude Intermediate 22 (approximately 200 mmol) in 3-pentanone (1 L) was treated with lithium bromide (10 eq, 174 g, 2 moles). The mixture was heated to reflux for 30 minutes, followed by concentration to dryness under reduced pressure. The residue was partitioned between ethyl acetate and water. The aqueous phase was extracted with ethyl acetate. The combined organics was washed with a 1% aqueous hydrochloric acid solution and with saturated aqueous sodium chloride solution, dried over anhydrous magnesium sulfate, and concentrated to dryness under reduced pressure. The residue was taken up again in 3-pentanone (1 L) and heated to reflux overnight in the presence of lithium bromide (250 g). The mixture was allowed to cool to room temperature and concentrated to dryness under reduced pressure. The residue was partitioned between ethyl acetate and water. The organic phase was washed with saturated aqueous sodium chloride solution, dried over anhydrous magnesium sulfate, filtered, and concentrated to dryness under reduced pressure.

The crude product was carried on without further purification. ES/MS calcd. for $C_{11}H_{11}BrNO_2^+$ 268.0. found m/z=268.1 (M+H)$^+$.

Intermediate 24: 4-(5-bromopent-1-yn-1-yl)aniline

A mixture of crude Intermediate 23 (200 mmol) was dissolved in a mixture of N-methylpyrrolidine/dichloromethane (1:1, 800 mL) and treated with tin (II) chloride dehydrate (218, 960 mmol) in 30 g portions. The exothermic reaction mixture was cooled in an ice-water bath. Following completion of the tin chloride addition, the cooling bath was removed and the mixture was allowed to regain room temperature. After 45 minutes of stirring, the mixture was quenched by adding it portion-wise to a mixture of ice and concentrated ammonium hydroxide solution. The slurry was filtered through a fritted glass funnel, washing with dichloromethane. The filtrates were concentrated under reduced pressure and diluted with diethyl ether. This organic phase was washed four times with water and once with a saturated aqueous sodium chloride solution, dried over anhydrous magnesium sulfate, filtered, and concentrated to dryness under reduced pressure. The residue was taken up in ethyl acetate and filtered through a ceramic filter. The filtrate was concentrated and the residue was triturated with benzene and filtered. The concentration-trituration cycle was performed five times. After the final iteration, the concentrated filtrate was purified by automated flash silica gel chromatography (hexanes/ethyl acetate). The desire fractions were concentrated to a lesser volume and then treated dropwise with methanesulfonic acid until the precipitation of further material appeared to cease. The solid was collected by Büchner filtration, washed with diethyl ether and ethyl acetate, and dried under house vacuum to provide the methanesulfonic acid salt of the title material as an off-white solid. ES/MS calcd. for $C_{11}H_{13}BrN^+$ 240.0. found m/z=240.1 (M+H)$^+$.

Intermediate 25: N-(4-(5-chloropent-1-yn-1-yl)phenyl)-2,2,2-trifluoroacetamide

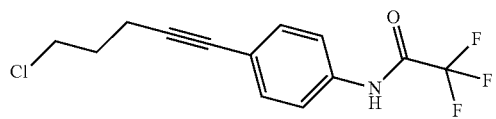

A mixture of 2,2,2-trifluoro-N-(4-iodophenyl)acetamide (3.2 g, 10 mmol, prepared according to Melissaris, A. P. and Litt, M. H. J Org Chem 1994, 59, 5818-5821), dichlorobis (triphenylphosphine)palladium(II) (0.14 g, 0.2 mmol), triphenylphosphine (19 mg, 0.07 mmol), and copper (I) iodide (0.019 g, 0.1 mmol) in triethylamine (50 mL) was degassed under Argon for 10 minutes while stirring in a 55° C. oil bath. The mixture was then treated with 5-chloropentyne (1.1 mL, 10 mmol). After four hours of heating, the mixture was allowed to cool to room temperature and was then filtered through a pad of Celite diatomaceous earth. The filtrate was concentrated under reduced pressure to provide the crude title compound, which was carried forward without further purification. ES/MS calcd. for $C_{14}H_{14}ClF_3NO^+$ : 290.1. found m/z=290.1 (M+H)$^+$ Intermediate 26: N-(4-(5-bromopent-1-yn-1-yl)phenyl)-2,2,2-trifluoroacetamide

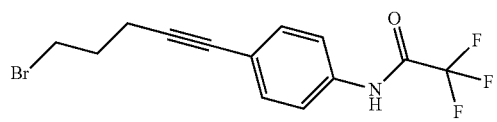 [SMILES: O=C(Nc1ccc(C#CCCCBr)cc1)C(F)(F)F]

A solution of Intermediate 25 (approximately 10 mmol) in 3-pentanone (200 mL) was treated with lithium bromide (10 eq, 100 mmol). The mixture was heated to reflux for 16 hours, followed by concentration to dryness under reduced pressure. The residue was taken up in ethyl acetate and washed with water. The concentrated organic phase was taken up again in 3-pentanone (200 mL) and heated to reflux for four hours in the presence of lithium bromide (10 eq, 100 mmol). The mixture was concentrated to dryness under reduced pressure. The residue was partitioned between ethyl acetate and water. The organic phase was washed with saturated aqueous sodium chloride solution, dried over anhydrous magnesium sulfate, filtered, and concentrated to dryness under reduced pressure. The crude product was purified via automated flash silica gel chromatography, using a 40 g SiliSep flash column (hexanes/ethyl acetate). Concentration of the desired fractions under reduced pressure provided the title compound as an off-white solid. ES/MS calcd. for $C_{13}H_{12}BrF_3NO^+$ 334.0. found m/z=334.1 (M+H)$^+$.

Intermediate 27: 1-(4-((6-bromohexyl)oxy)butyl)-4-nitrobenzene

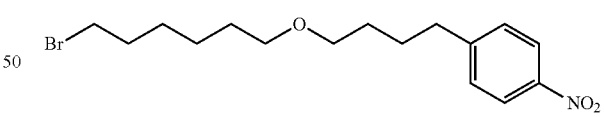

A stirred mixture of 4-(4-nitrophenyl)butan-1-ol (2.0 g, 10 mmol), tetra-n-butylammonium hydrogen sulfate (0.17 g, 0.5 mmol), and 1,6-dibromohexane (3.2 mL, 20 mmol) in dichloromethane (10 mL) was treated with aqueous sodium hydroxide solution (10 M, 1 mL). The reaction mixture was stirred for 6 days at room temperature. The organic and aqueous phases were separated. The aqueous phase was extracted thrice with dichloromethane. The combined organics were washed with water, dried over anhydrous magnesium sulfate, filtered, and concentrated under reduced pressure. The crude residue was purified via automated flash silica gel chromatography, using a 40 g SiliSep flash column (hexanes/ethyl acetate). Concentration of the desired fractions under reduced pressure provided the title compound as a pale straw-colored oil (0.72 g, 20%). ES/MS calcd. for $C_{16}H_{25}BrNO_3^+$ 358.1. found m/z=358.2 (M+H)$^+$.

Intermediate 28: 3-(((1,6-diethyl-4-((tetrahydro-2H-pyran-4-yl)amino)-1H-pyrazolo[3,4-b]pyridin-5-yl)methyl)amino)-4-ethoxycyclobut-3-ene-1,2-dione

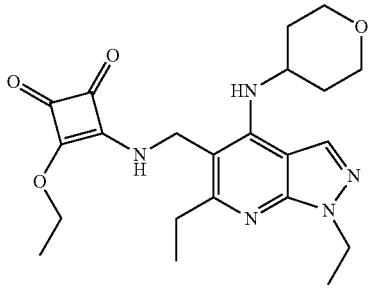 [SMILES: CCOc1c(NCc2c(CC)nc3c(cnn3CC)c2NC2CCOCC2)c(=O)c1=O]

A suspension of 5-(aminomethyl)-1,6-diethyl-N-(tetrahydro-2H-pyran-4-yl)-1H-pyrazolo[3,4-b]pyridin-4-amine dihydrochloride (0.60 g, 1.6 mmol) in ethanol (8 mL) was treated with N,N-diisopropylethylamine (DIEA, 0.57 mL, 3.3 mmol), giving a clear, homogeneous mixture, which was then cooled in an ice-water bath. 3,4-Diethoxycyclobut-3-ene-1,2-dione (TCI America, 0.41 g, 0.36 mmol) was then added dropwise via syringe. Following completion of the addition, the mixture was allowed to regain room temperature and stir overnight. The precipitated solid was collected by Büchner filtration, washed with ethanol, and dried under house vacuum to provide the title compound as a white solid. ES/MS calcd. for $C_{22}H_{30}N_5O_4^+$ 428.2. found m/z=428.3 (M+H)$^+$.

Intermediate 29: N-[[1,6-Diethyl-4-[(tetrahydro-2H-pyran-4-yl)amino]-1H-pyrazolo[3,4-b]pyridin-5-yl]methyl]-3-(2-oxopropyl)benzamide

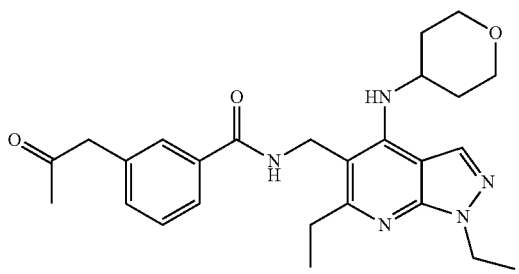 [SMILES: CCc1nc2c(cnn2CC)c(NC2CCOCC2)c1CNC(=O)c1cccc(CC(C)=O)c1]

HATU (202 mg, 0.531 mmol) and DIEA (0.294 mL, 1.69 mmol) were added to a stirring solution 3-(2-oxopropyl)benzoic acid (86 mg, 0.483 mmol) in DMF (5 mL) at rt. After 5 min, 5-(aminomethyl)-1,6-diethyl-N-(tetrahydro-2H-pyran-4-yl)-1H-pyrazolo[3,4-b]pyridin-4-amine (200 mg, 0.531 mmol) was added and the resulting solution was stirred an additional 2 h. The reaction mixture was poured into H$_2$O (50 mL) and the aqueous layer was extracted with EtOAc (3×30 mL). The combined organic layers were washed with H$_2$O (2×100 mL), brine (100 mL), dried over Na$_2$SO$_4$ (s), and concentrated to give a yellow oil (376 mg). Chromatography (9:1, CH$_2$Cl$_2$/MeOH, 0.1% Et$_3$N) afforded the title compound (212 mg, 95%) as a yellow solid. ES/MS calcd. for $C_{26}H_{34}N_5O_3^+$ 464.3. found m/z=464.3 (M+H)$^+$.

Intermediate 30: N-[[1,6-Diethyl-4-[(tetrahydro-2H-pyran-4-yl)amino]-1H-pyrazolo[3,4-b]pyridin-5-yl]methyl]-3-formylbenzamide

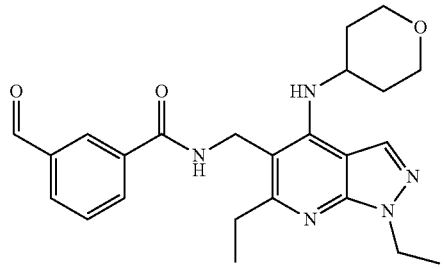 [SMILES: CCc1nc2c(cnn2CC)c(NC2CCOCC2)c1CNC(=O)c1cccc(C=O)c1]

The title compound was synthesized in a manner analogous to that described for Intermediate 29, using 3-formylbenzoic acid in place of 3-(2-oxopropyl)benzoic acid. ES/MS calcd. for $C_{24}H_{30}N_5O_3^+$ 436.2. found m/z=436.2 (M+H)$^+$.

Intermediate 31: N-[[1,6-Diethyl-4-[(tetrahydro-2H-pyran-4-yl)amino]-1H-pyrazolo[3,4-b]pyridin-5-yl]methyl]-4-formylbenzamide

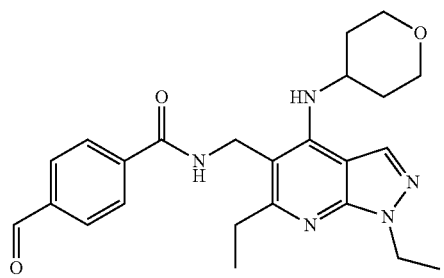 [SMILES: CCc1nc2c(cnn2CC)c(NC2CCOCC2)c1CNC(=O)c1ccc(C=O)cc1]

The title compound was synthesized in a manner analogous to that described for Intermediate 29, using 4-formylbenzoic acid in place of 3-(2-oxopropyl)benzoic acid. ES/MS calcd. for $C_{24}H_{30}N_5O_3^+$ 436.2. found m/z=436.2 (M+H)$^+$.

Intermediate 32: N-[[1,6-Diethyl-4-[(tetrahydro-2H-pyran-4-yl)amino]-1H-pyrazolo[3,4-b]pyridin-5-yl]methyl]-4-(5-hydroxypent-1-yn-1-yl)benzamide

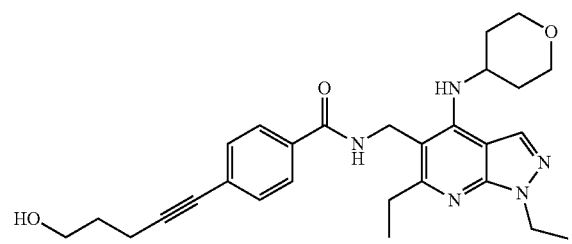 [SMILES: CCc1nc2c(cnn2CC)c(NC2CCOCC2)c1CNC(=O)c1ccc(C#CCCCO)cc1]

The title compound was synthesized in a manner analogous to that described for Intermediate 29, using Intermediate 21 in place of 3-(2-oxopropyl)benzoic acid. ES/MS calcd. for $C_{28}H_{36}N_5O_3^+$ 490.3. found m/z=490.4 (M+H)$^+$.

Intermediate 33: 8-Bromo-N-[[1,6-diethyl-4-[(tetrahydro-2H-pyran-4-yl)amino]-1H-pyrazolo[3,4-b]pyridin-5-yl]methyl]octanamide

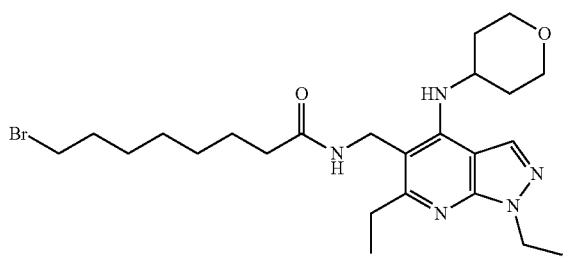 [SMILES: CCc1nc2c(cnn2CC)c(NC2CCOCC2)c1CNC(=O)CCCCCCCBr]

The title compound was synthesized in a manner analogous to that described for Intermediate 29, using 8-bromooctanoic acid in place of 3-(2-oxopropyl)benzoic acid. ES/MS calcd. for $C_{24}H_{39}BrN_5O_2^+$ 508.2. found m/z=508.2 (M+H)$^+$.

Intermediate 34: N-[[1,6-Diethyl-4-[(tetrahydro-2H-pyran-4-yl)amino]-1H-pyrazolo[3,4-b]pyridin-5-yl]methyl]-4-(5-hydroxypentyl)benzamide

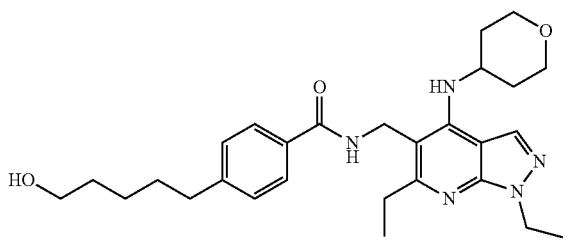 [SMILES: CCc1nc2c(cnn2CC)c(NC2CCOCC2)c1CNC(=O)c1ccc(CCCCCO)cc1]

Pd(OH)$_2$ (200 mg) was added to a solution of Intermediate 32 (200 mg, 0.40 mmol) in THF/MeOH (5 mL each). The solution was treated with H$_2$ at ambient pressure for 3 h. The reaction mixture was then filtered through a plug of celite. The plug was washed with MeOH (50 mL) and the solvent was concentrated in vacuo to afford the title compound as a pale yellow solid (200 mg). ES/MS calcd. for $C_{28}H_{40}N_5O_3^+$ 494.3. found m/z=494.4 (M+H)$^+$.

Intermediate 35: 1-(4-(5-bromopent-1-yn-1-yl)phenyl)-3-((1,6-diethyl-4-((tetrahydro-2H-pyran-4-yl)amino)-1H-pyrazolo[3,4-b]pyridin-5-yl)methyl)urea

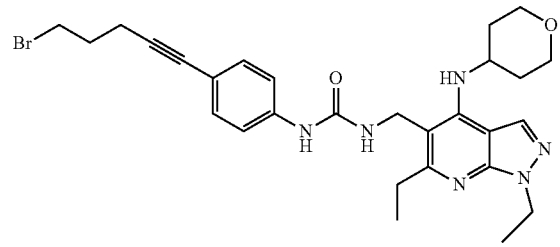 [SMILES: CCc1nc2c(cnn2CC)c(NC2CCOCC2)c1CNC(=O)Nc1ccc(C#CCCCBr)cc1]

A suspension of Intermediate 24 methanesulfonic acid salt (1.4 g, 4.2 mmol) in dichloromethane (50 mL) was treated with triethylamine (8.8 mL, 63 mmol) and then the mixture was cooled in an ice-water bath and treated with triphosgene (0.93 g, 3.2 mmol), followed by 5-(aminomethyl)-1,6-diethyl-N-(tetrahydro-2H-pyran-4-yl)-1H-pyrazolo[3,4-b]pyridin-4-amine dihydrochloride (1.3 g, 3.4 mmol). The mixture was quenched by the addition of methanol and concentrated under reduced pressure. The residue was partitioned between ethyl acetate and water. The aqueous phase was extracted twice with ethyl acetate. The combined organics were washed with a 5% aqueous potassium hydrogen sulfate solution and saturated aqueous sodium chloride solution and then concentrated under reduced pressure. The crude residue was purified via automated flash silica gel chromatography, using a SiliSep flash column (dichloromethane/methanol/ammonium hydroxide). Concentration of the desired fractions under reduced pressure provided the title compound as a pale tan foam. ES/MS calcd. for $C_{28}H_{36}BrN_6O_2^+$ 567.2. found m/z=567.2 (M+H)$^+$.

Intermediate 36: N-[[1,6-Diethyl-4-[(tetrahydro-2H-pyran-4-yl)amino]-1H-pyrazolo[3,4-b]pyridin-5-yl]methyl]-4-(5-oxopentyl)benzamide

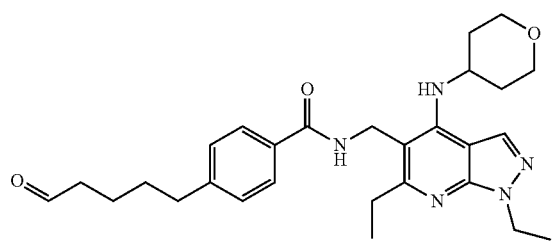 [SMILES: CCc1nc2c(cnn2CC)c(NC2CCOCC2)c1CNC(=O)c1ccc(CCCCC=O)cc1]

Dess Martin Reagent (432 mg, 1.02 mmol) was added to a solution of Intermediate 34 (250 mg, 0.51 mmol) in THF (5 mL) and DCM (5 mL). The resultant mixture was stirred at rt for 2 h. The solvent was removed in vacuo and the crude solid was purified by column chromatography on silica gel eluting with 0-10% DCM-MeOH to afford the title compound as a white solid (250 mg). ES/MS calcd. for $C_{28}H_{38}N_5O_3^+$ 492.3. found m/z=492.3 (M+H)$^+$.

Intermediate 37: (R)—N-(4-(5-((2-((tert-butyldimethylsilyl)oxy)-2-(8-hydroxy-2-oxo-1,2-dihydroquinolin-5-yl)ethyl)amino)pent-1-yn-1-yl)phenyl)-2,2,2-trifluoroacetamide

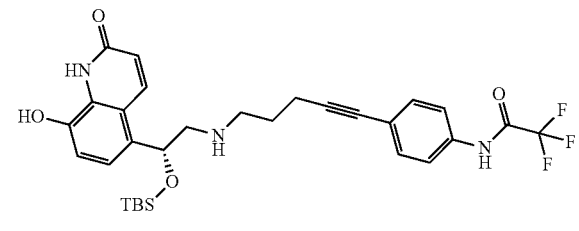

A mixture of Intermediate 26 (0.33 g, 1.0 mmol) and Intermediate 2 (0.40 g, 1.2 mmol) in DMF (5 mL) was treated with N,N-diisopropylethylamine (DIEA, 0.25 mL, 1.5 mmol) and catalytic potassium iodide. The mixture was heated overnight in a 55° C. oil bath. The mixture was concentrated under reduced pressure and purified via automated flash silica gel chromatography, using a 12 g Isco RediSep flash column (dichloromethane/methanol/ammonium hydroxide). Concentration of the desired fractions under reduced pressure provided the title compound (0.53 g, 90%). ES/MS calcd. for $C_{30}H_{37}F_3N_3O_4Si^+$ 588.3. found m/z=588.4 (M+H)$^+$.

Intermediate 38: (R)-tert-butyl (5-(4-aminophenyl)pent-4-yn-1-yl)(2-((tert-butyldimethylsilyl)oxy)-2-(8-hydroxy-2-oxo-1,2-dihydroquinolin-5-yl)ethyl)carbamate

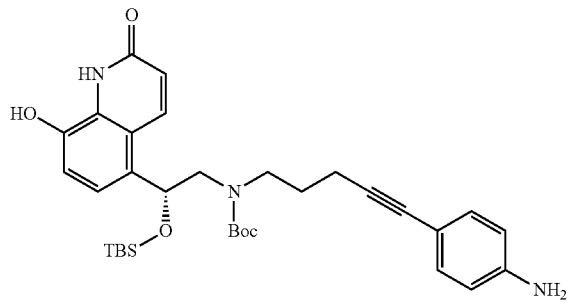

A solution of Intermediate 37 (approximately 0.35 g, 0.60 mmol) in dichloromethane (5 mL) was treated successively with triethylamine (0.42 g, 3.0 mmol), di-tert-butyldicarbonate (0.39 g, 1.8 mmol), and N,N-dimethylaminopyridine (DMAP, 50 mg). After two hours the mixture was concentrated to dryness under reduced pressure and taken up in methanol/water (2:1, 5 mL). Tetrahydrofuran was added dropwise until a homogeneous mixture was obtained, which was then treated with potassium carbonate (approximately 500 mg). The mixture was left stirring overnight at room temperature. It was concentrated to an aqueous suspension under reduced pressure and then adjusted to pH 7 with the addition of a 5% aqueous potassium hydrogen sulfate solution. The aqueous mixture was extracted thrice with dichloromethane. The combined extracts were concentrated to a reddish-brown foam, which was then purified by automated flash silica gel chromatography, using a 12 g Silicycle SiliSep flash column (dichloromethane/methanol/ammonium hydroxide). Concentration of the desired fractions under reduced pressure provided the title compound (0.11 g, 30%) as a pale tan foam. ES/MS calcd. for $C_{33}H_{46}N_3O_5Si^+$ 592.3. found m/z=592.4 (M+H)$^+$.

Intermediate 39: (R)-8-hydroxy-5-(2,2,3,3-tetramethyl-18-(4-nitrophenyl)-4,14-dioxa-7-aza-3-silaoctadecan-5-yl)quinolin-2(1H)-one

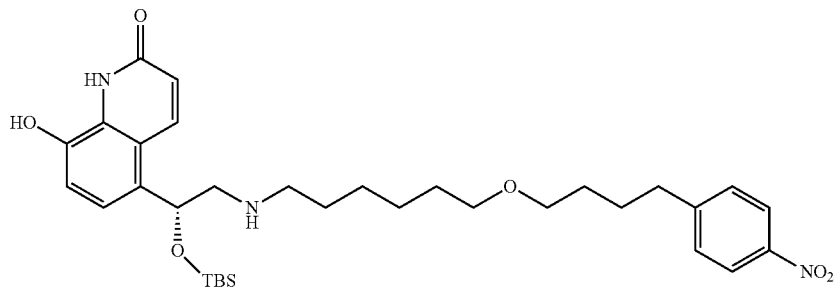

The title compound was prepared in a manner analogous to that described for Intermediate 37, using Intermediate 27 in place of Intermediate 26. ES/MS calcd. for $C_{33}H_{50}N_3O_6Si^+$ 612.4. found m/z=612.5 (M+H)$^+$.

Intermediate 40: (R)-tert-butyl (2-(8-((tert-butoxycarbonyl)oxy)-2-oxo-1,2-dihydroquinolin-5-yl)-2-((tert-butyldimethylsilyl)oxy)ethyl)(6-(4-(4-nitrophenyl)butoxy)hexyl)carbamate

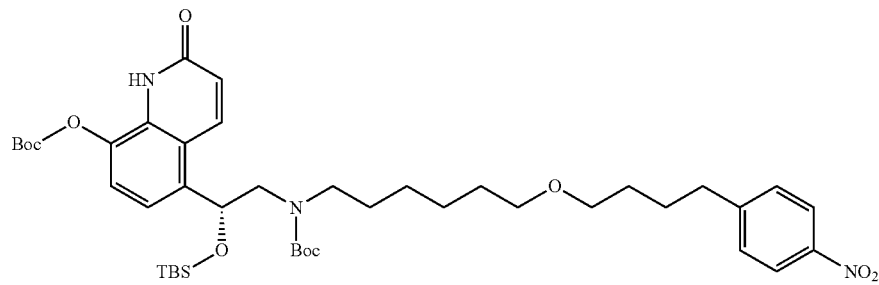

A solution of Intermediate 39 (0.53 g, 0.87 mmol) in dichloromethane (5 mL) was treated with di-tert-butyldicarbonate (0.57 g, 2.6 mmol), triethylamine (0.61 mL, 4.4 mmol) and N,N-dimethylaminopyridine (DMAP, 20 mg). The reaction mixture was stirred overnight at room temperature and then concentrated to dryness under reduced pressure. The residue was purified via automated flash silica gel chromatography, using a 25 g SiliSep flash column (hexanes/ethyl acetate). Concentration of the desired fractions under reduced pressure provided the title compound as clear, colorless oil, which turned into a white foam under reduced pressure. ES/MS calcd. for $C_{43}H_{66}N_3O_{10}Si^+$ 812.5. found m/z=812.6 (M+H)$^+$.

Intermediate 41: (R)-tert-butyl (2-(2,8-bis((tert-butoxycarbonyl)oxy)quinolin-5-yl)-2-((tert-butyldimethylsilyl)oxy)ethyl)(6-(4-(4-nitrophenyl)butoxy)hexyl)carbamate

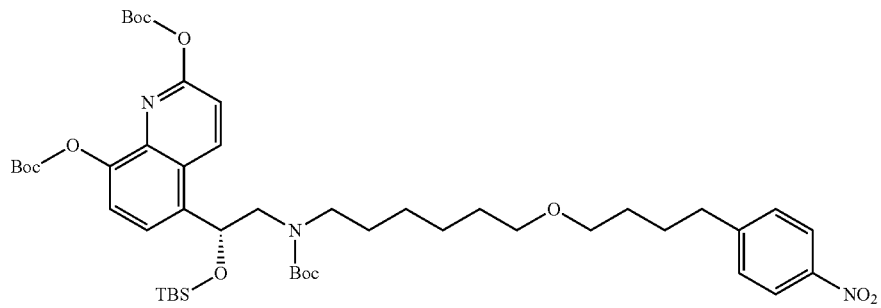

A solution of Intermediate 40 (approximately 150 mg) in dichloromethane (5 mL) was treated with di-tert-butyldicarbonate and triethylamine (both q.s.) and catalytic N,N-dimethylaminopyridine (DMAP) at room temperature. Upon LC/MS analysis of a complete tris-Boc protection, the mixture was concentrated to dryness under reduced pressure, and the residue was purified by automated flash silica gel chromatography, using a 25 g SiliSep flash column (hexanes/ethyl acetate). Concentration of the desired fractions under reduced pressure provided the title compound (175 mg) as sticky colorless foam. ES/MS calcd. for $C_{48}H_{73}N_3NaO_{12}Si^+$ 934.5. found m/z=934.5 (M+Na)$^+$.

Intermediate 42: (R)-tert-butyl (6-(4-(4-aminophenyl)butoxy)hexyl)(2-(2,8-bis((tert-butoxycarbonyl)oxy)quinolin-5-yl)-2-((tert-butyldimethylsilyl)oxy)ethyl)carbamate

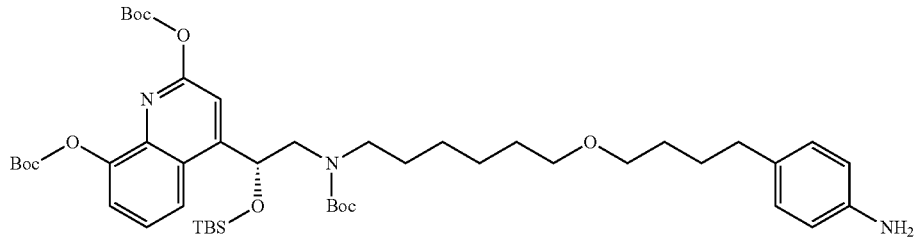

Intermediate 41 (175 mg, 0.19 mmol) was dissolved in methanol (4 mL) and ethyl acetate (1 mL) and treated with palladium on carbon (10% w/w, wet Degussa-type, catalytic amount). The suspension was stirred under a balloon of hydrogen gas for 45 minutes. The mixture was then filtered through a pad of Celite diatomaceous earth, and the filtrate was concentrated to dryness under reduced pressure to provide the title material. ES/MS calcd. for $C_{48}H_{76}N_3O_{10}Si^+$ 882.5. found m/z=882.5 (M+H)$^+$.

Intermediate 43: 3-[2-[[(R)-2-[(3-[[(tert-Butyldimethylsilyl)oxy]methyl]-4-hydroxyphenyl]-2-hydroxyethyl]amino]propyl]-N-[[1,6-diethyl-4-[(tetrahydro-2H-pyran-4-yl)amino]-1H-pyrazolo[3,4-b]pyridin-5-yl]methyl]benzamide

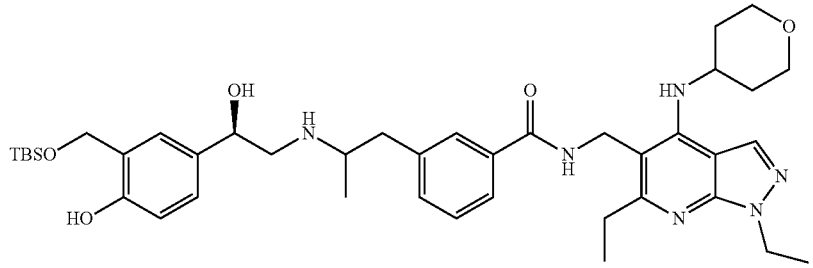 [SMILES: CCc1nc2c(cnn2CC)c(NC2CCOCC2)c1CNC(=O)c1cccc(CC(C)NC[C@H](O)c2ccc(O)c(CO[Si](C)(C)C(C)(C)C)c2)c1]

Glacial acetic acid (0.024 mL, 0.421 mmol) and Intermediate 8 (125 mg, 0.421 mmol) were added to a stirring solution of Intermediate 29 (130 mg, 0.28 mmol) in DMF (3 mL) at rt. The resulting solution was stirred for 2 h. NaBH(OAc)$_3$ (178 mg, 0.84 mmol) was added in portions. The reaction mixture was stirred overnight then poured into satd. NaHCO$_3$ (40 mL). The precipitate was filtered, washed with H$_2$O (50 mL), and dried to give the title compound (118 mg) as an off-white solid. The compound was used with no further purification. ES/MS calcd. for $C_{41}H_{61}N_6O_5Si^+$ 745.5. found m/z=745.5 (M+H)$^+$.

Intermediate 44: (R)-4-[5-[[2-[[tert-Butyldimethylsilyl)oxy]-2-(8-hydroxy-2-oxo-1,2-dihydroquinolin-5-yl)ethyl]amino]pentyl]-N-[[1,6-diethyl-4-[(tetrahydro-2H-pyran-4-yl)amino]-1H-pyrazolo[3,4-b]pyridin-5-yl]methyl]benzamide NaCNBH$_3$ (160 mg, 2.55 mmol) was added to a solution of Intermediate 2 (240 mg, 0.61 mmol), Intermediate 36 (250 mg, 0.51 mmol), and acetic acid (0.032 mL, 0.561 mmol) in THF (5 mL). The reaction mixture was stirred at rt for 1 h. H$_2$O (2 mL) was added followed by satd. NaHCO$_3$ solution (20 mL) and EtOAc (100 mL). The organic layer was separated, dried over MgSO$_4$ (s), filtered, and concentrated in vacuo. Purification by column chromatography on silica gel eluting with a gradient of 0-100% DCM-DCM/MeOH/Ammonia (80/20/1) afforded the title compound as a yellow solid (200 mg). ES/MS calcd. for $C_{45}H_{64}N_7O_5Si^+$ 810.5. found m/z=810.5 (M+H)$^+$.

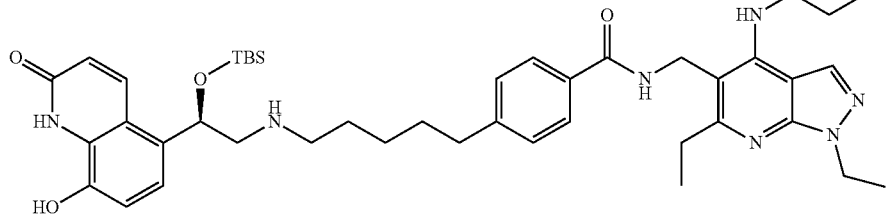

Intermediate 45: (R)-3-[[[2-(3-[[(tert-Butyldimethylsilyl)oxy]methyl]-4-hydroxyphenyl]-2-hydroxyethyl]amino]methyl]-N-[[1,6-diethyl-4-[(tetrahydro-2H-pyran-4-yl)amino]-1H-pyrazolo[3,4-b]pyridin-5-yl]methyl]benzamide

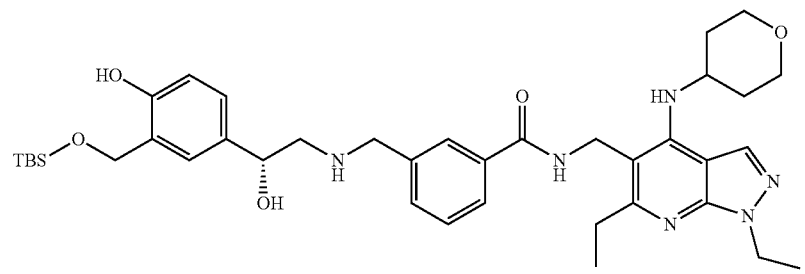

The title compound was synthesized in a manner analogous to that described, using Intermediate 30 in place of Intermediate 29. ES/MS calcd. for $C_{39}H_{56}N_6NaO_5Si^+$ 739.4. found m/z=739.4 (M+Na)$^+$.

Intermediate 46: (R)-4-[[[2-(3-[[(tert-Butyldimethylsilyl)oxy]methyl]-4-hydroxyphenyl]-2-hydroxyethyl]amino]methyl]-N-[[1,6-diethyl-4-[(tetrahydro-2H-pyran-4-yl)amino]-1H-pyrazolo[3,4-b]pyridin-5-yl]methyl]benzamide

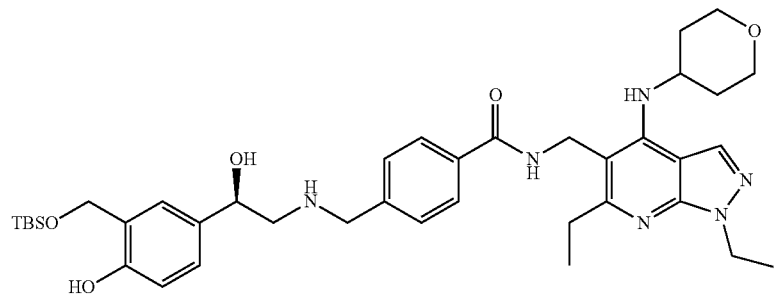 [SMILES: CCc1nc2c(cnn2CC)c(NC2CCOCC2)c1CNC(=O)c1ccc(CNC[C@H](O)c2ccc(O)c(CO[Si](C)(C)C(C)(C)C)c2)cc1]

The title compound was synthesized in a manner analogous to that described for Intermediate 43, using Intermediate 31 in place of Intermediate 29. ES/MS calcd. for $C_{39}H_{56}N_6NaO_5Si^+$ 739.4. found m/z=739.4 (M+Na)$^+$.

Intermediate 47: (R)-Methyl 3-[2-[[2-[4-(benzyloxy)-3-[[(tert-butyldimethylsilyl)oxy]methyl]phenyl]-2-[(tert-butyldimethylsilyl)oxy]ethyl]amino]-2-methylpropyl]benzoate

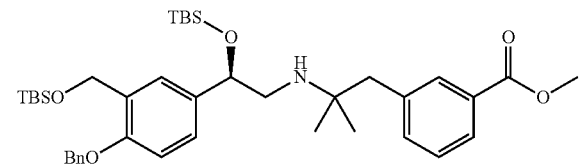

Intermediate 6 (1.6 g, 2.89 mmol) and Intermediate 19 (900 mg, 4.3 mmol) were heated neat at 95° C. for 3 days. The reaction mixture was cooled then chromatography (3:1 Hexanes/EtOAc, 0.1% Et$_3$N) afforded the title compound (730 mg, 37%). ES/MS calcd. for $C_{40}H_{62}NO_5Si_2^+$ 692.4. found m/z=692.4 (M+H)$^+$.

Intermediate 48: (R)-Methyl 3-[2-[[2-[8-(benzyloxy)-2-oxo-1,2-dihydroquinolin-5-yl]-2-[(tert-butyldimethylsilyl)oxy]ethyl]amino]-2-methylpropyl]benzoate

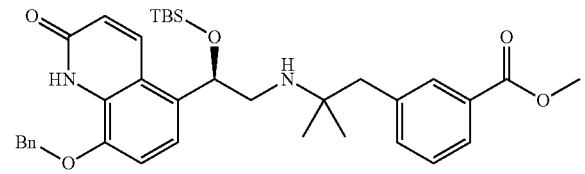

The title compound was synthesized in a manner analogous to that described for Intermediate 47, using (R)-8-(benzyloxy)-5-[2-bromo-1-[(tert-butyldimethylsilyl)oxy]ethyl]quinolin-2(1H)-one in place of Intermediate 6. ES/MS calcd. for $C_{36}H_{47}N_2O_5Si^+$ 615.3. found m/z=615.3 (M+H)$^+$.

Intermediate 49: (R)-3-[2-[[2-[4-(Benzyloxy)-3-[[(tert-butyldimethylsilyl)oxy]methyl]phenyl-2-[(tert-butyldimethylsilyl)oxy]ethyl]amino]-2-methylpropyl]benzoic acid

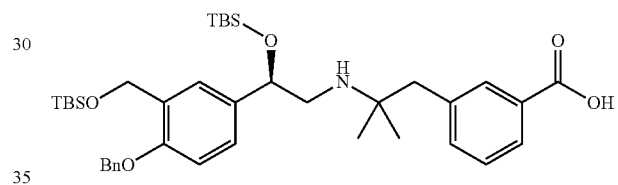

LiOH (242 mg, 10.1 mmol) was added to a stirring solution of Intermediate 47 in THF/MeOH/H$_2$O (3:1:1) (10 mL) at rt. The resulting mixture was stirred for 3 days then quenched with 1 N HCl (pH<3). The aqueous layer was extracted with EtOAc (3×30 mL). The combined organic layers were washed with brine, dried over Na$_2$SO$_4$ (s), and concentrated to give the title compound (730 mg). ES/MS calcd. for $C_{39}H_{60}NO_5Si_2^+$ 678.4. found m/z=678.5 (M+H)$^+$.

Intermediate 50: (R)-3-[2-[[2-[8-(Benzyloxy)-2-oxo-1,2-dihydroquinolin-5-yl]-2-[(tert-butyldimethylsilyl)oxy]ethyl]amino]-2-methylpropyl]benzoic acid

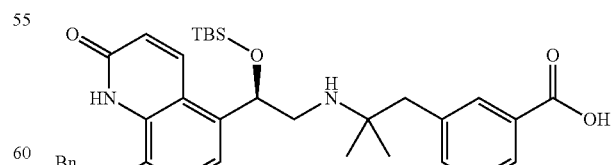

The title compound was synthesized in a manner analogous to that described for Intermediate 49, using Intermediate 48 as a substrate. ES/MS calcd. for $C_{35}H_{45}N_2O_5Si^+$ 601.3. found m/z=601.3 (M+H)$^+$.

Intermediate 51: (R)-3-[2-[[2-[4-(Benzyloxy)-3-[[(tert-butyldimethylsilyl)oxy]methyl]phenyl]-2-[(tert-butyldimethylsilyl)oxy]ethyl]amino]-2-methylpropyl]-N-[[1,6-diethyl-4-[(tetrahydro-2H-pyran-4-yl)amino]-1H-pyrazolo[3,4-b]pyridin-5-yl]methyl]benzamide

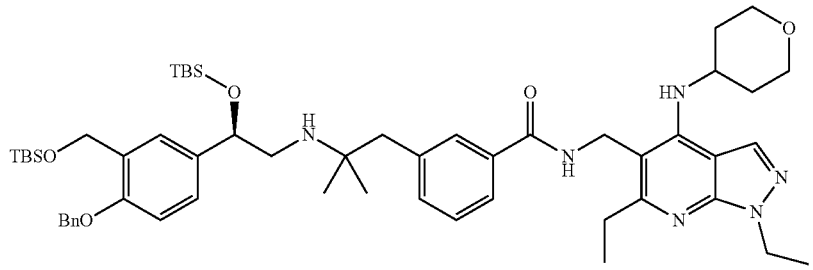

The title compound was synthesized in a manner analogous to that described for Intermediate 29, using Intermediate 49 in place of 3-(2-oxopropyl)benzoic acid. ES/MS calcd. for $C_{55}H_{83}N_6O_5Si_2^+$ 963.6. found m/z=963.6 (M+H)$^+$.

Intermediate 52: (R)-3-[2-[[2-[8-(Benzyloxy)-2-oxo-1,2-dihydroquinolin-5-yl]-2-[(tert-butyldimethylsilyl)oxy]ethyl]amino]-2-methylpropyl]-N-[[1,6-diethyl-4-[(tetrahydro-2H-pyran-4-yl)amino]-1H-pyrazolo[3,4-b]pyridin-5-yl]methyl]benzamide

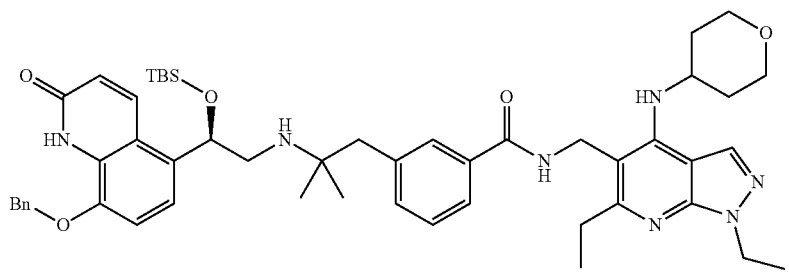

The title compound was synthesized in a manner analogous to that described for Intermediate 29, using Intermediate 50 in place of 3-(2-oxopropyl)benzoic acid. ES/MS calcd. for $C_{51}H_{68}N_7O_5Si^+$ 886.5. found m/z=886.5 (M+H)$^+$.

Intermediate 53: (R)-3-[2-[[2-[4-(Benzyloxy)-3-(hydroxymethyl)phenyl]-2-hydroxyethyl]-amino]-2-methylpropyl]-N-[[1,6-diethyl-4-[(tetrahydro-2H-pyran-4-yl)amino]-1H-pyrazolo[3,4-b]pyridin-5-yl]methyl]benzamide

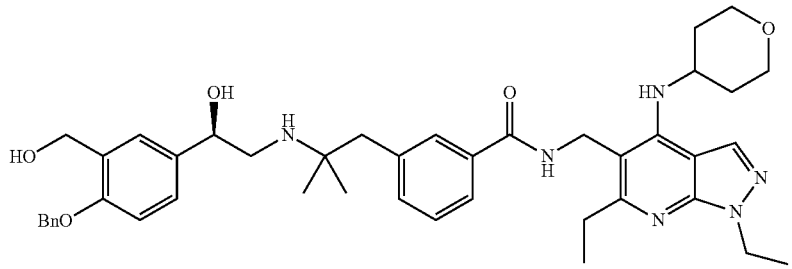 [SMILES: CCc1nc2c(cnn2CC)c(NC2CCOCC2)c1CNC(=O)c1cccc(CC(C)(C)NC[C@H](O)c2ccc(OCc3ccccc3)c(CO)c2)c1]

The title compound was synthesized in a manner analogous to that described for Intermediate 3, using Intermediate 51 as a substrate. ES/MS calcd. for $C_{43}H_{55}N_6O_5^+$ 735.2. found m/z=735.5 (M+H)$^+$.

Intermediate 54: (R)-3-[2-[[2-[8-(Benzyloxy)-2-oxo-1,2-dihydroquinolin-5-yl]-2-hydroxyethyl]amino]-2-methylpropyl]-N-[[1,6-diethyl-4-[(tetra hydro-2H-pyran-4-yl)amino]-1H-pyrazolo[3,4-b]pyridin-5-yl]methyl]benzamide

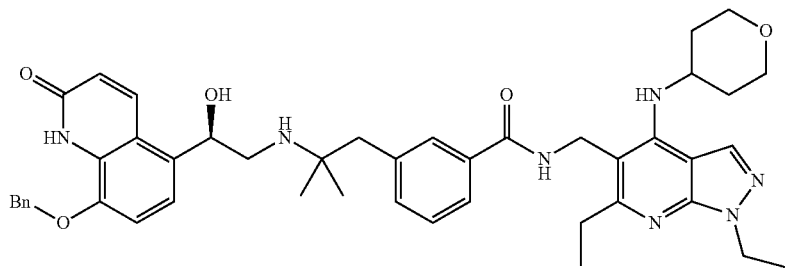 [SMILES: CCc1nc2c(cnn2CC)c(NC2CCOCC2)c1CNC(=O)c1cccc(CC(C)(C)NC[C@H](O)c2ccc(OCc3ccccc3)c3[nH]c(=O)ccc23)c1]

The title compound was synthesized in a manner analogous to that described for Intermediate 3, using Intermediate 52 as a substrate. ES/MS calcd. for $C_{45}H_{54}N_7O_5^+$ 772.4. found m/z=772.4 (M+H)$^+$.

Intermediate 55: (R)-8-[[2-[(tert-Butyldimethylsilyl)oxy]-2-(8-hydroxy-2-oxo-1,2-dihydroquinolin-5-yl)ethyl]amino]-N-[[1,6-diethyl-4-[(tetrahydro-2H-pyran-4-yl)amino]-1H-pyrazolo[3,4-b]pyridin-5-yl]methyl]octanamide

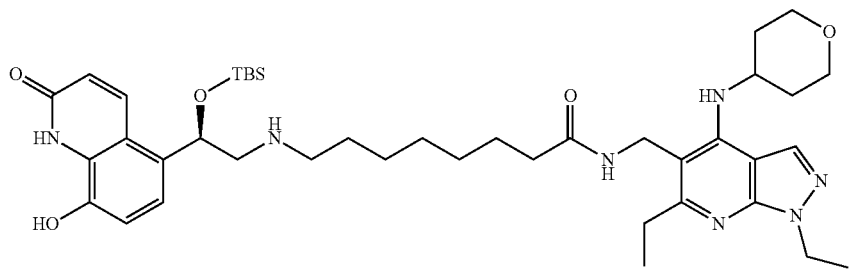

The title compound was prepared in a manner analogous to that described for Intermediate 37, using Intermediate 33 in place of Intermediate 26. ES/MS calcd. for $C_{41}H_{64}N_7O_5Si$ 762.5. found m/z=762.5 (M+H)$^+$.

Intermediate 56: (R)-1-(4-(5-((2-((tert-butyldimethylsilyl)oxy)-2-(8-hydroxy-2-oxo-1,2-dihydroquinolin-5-yl)ethyl)amino)pent-1-yn-1-yl)phenyl)-3-((1,6-diethyl-4-((tetrahydro-2H-pyran-4-yl)amino)-1H-pyrazolo[3,4-b]pyridin-5-yl)methyl)urea

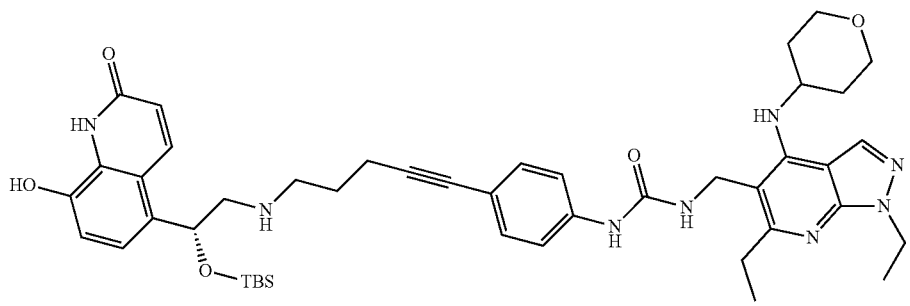

The title compound was prepared in a manner analogous to that described for Intermediate 37, using Intermediate 35 in place of Intermediate 26. ES/MS calcd. for $C_{45}H_{61}N_8O_5Si^+$ 821.5. found m/z=821.6 $(M+H)^+$.

Intermediate 57: (R)-tert-butyl (2-(2,8-bis((tert-butoxycarbonyl)oxy)quinolin-5-yl)-2-((tert-butyldimethylsilyl)oxy)ethyl)(6-(4-(4-(3-((1,6-diethyl-4-((tetrahydro-2H-pyran-4-yl)amino)-1H-pyrazolo[3,4-b]pyridin-5-yl)methyl)ureido)phenyl)butoxy)hexyl)carbamate

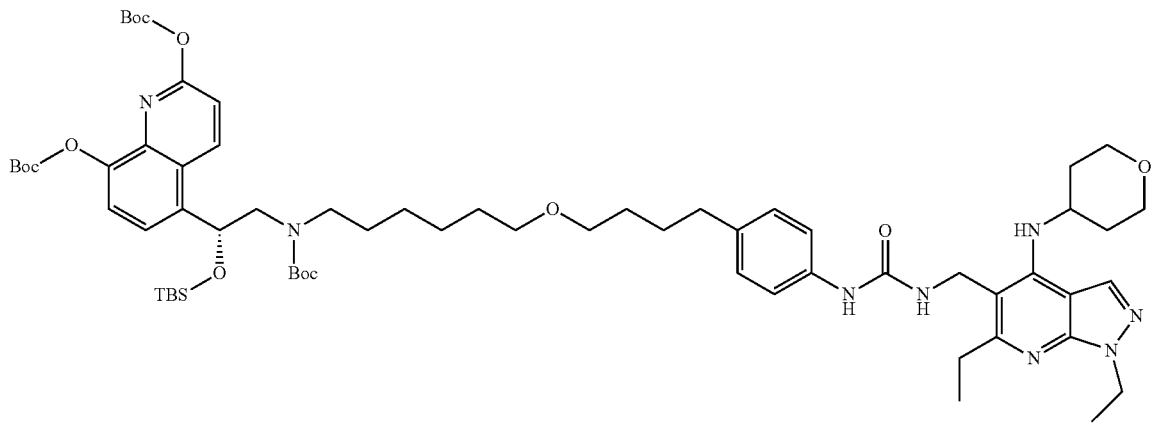

The title compound was prepared in a manner analogous to that described for Intermediate 35, using Intermediate 42 in place of Intermediate 24. ES/MS calcd. for $C_{65}H_{99}N_8O_{12}Si^+$ 1211.7. found m/z=1211.6 $(M+H)^+$.

Intermediate 58: (R)-1-(4-(5-((2-(((tert-butyldimethylsilyl)oxy)-2-(5-hydroxy-3-oxo-3,4-dihydro-2H-benzo[b][1,4]oxazin-8-yl)ethyl)amino)pent-1-yn-1-yl)phenyl)-3-(1,6-diethyl-4-((tetrahydro-2H-pyran-4-yl)amino)-1H-pyrazolo[3,4-b]pyridin-5-yl)methyl)urea

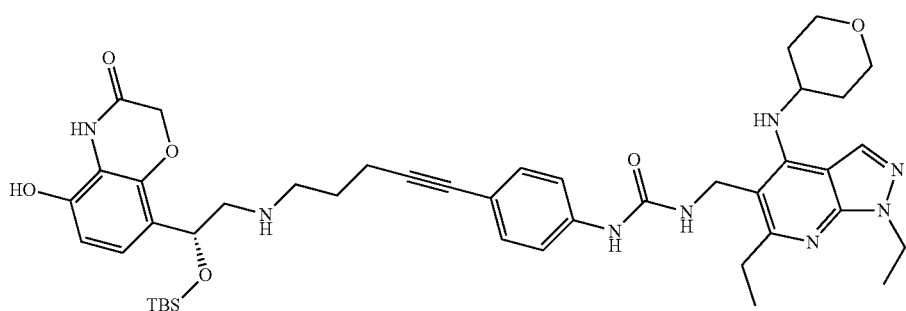

The title compound was prepared in a manner analogous to that described for Intermediate 56, using (R)-8-(2-amino-1-((tert-butyldimethylsilyl)oxy)ethyl)-5-hydroxy-2H-benzo[b][1,4]oxazin-3(4H)-one in place of Intermediate 2. ES/MS calcd. for $C_{44}H_{61}N_8O_6Si^+$ 825.5. found m/z=825.6 $(M+H)^+$.

Example 1

N-[[1,6-Diethyl-4-[(tetrahydro-2H-pyran-4-yl)amino]-1H-pyrazolo[3,4-b]pyridin-5-yl]methyl]-3-[2-[[(R)-2-hydroxy-2-(8-hydroxy-2-oxo-1,2-dihydroquinolin-5-yl)ethyl]amino]propyl]benzamide

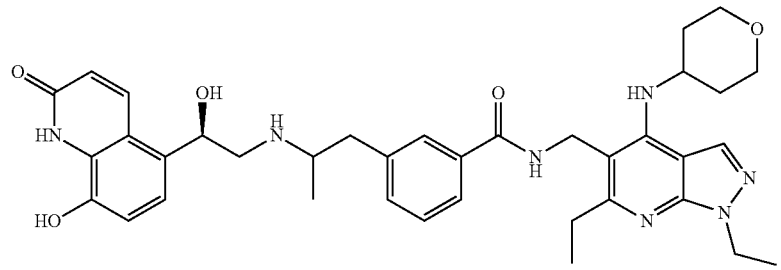 [SMILES: CCc1nc2c(cnn2CC)c(NC2CCOCC2)c1CNC(=O)c1cccc(CC(C)NC[C@H](O)c2ccc(O)c3[nH]c(=O)ccc23)c1]

The title compound was prepared in a manner analogous to that described for Intermediate 43, using Intermediate 4 in place of Intermediate 8.

$^1$H NMR (400 MHz, DMSO-d6) δ 10.51 (brs, 1H), 9.15 (brs, 1H), 8.86 (brs, 1H), 8.73 (brs, 1H), 8.34 (brs, 1H), 8.15 (dd, 1H, J=4.5, 9.9 Hz), 7.77 (m, 2H), 7.47 (m, 2H), 7.19 (dd, 1H, J=6.6, 8.0 Hz), 7.00 (d, 1H, J=8.0 Hz), 6.60 (d, 1H, J=10.0 Hz), 6.23 (brs, 1H), 5.35 (m, 1H), 4.57 (m, 2H), 4.44 (dd, 2H, J=7.1, 14.3 Hz), 4.29 (m, 2H), 3.9-2.64 (m, 11H), 1.95 (m, 2H), 1.65 (m, 2H), 1.37 (t, 3H, J=7.2 Hz), 1.30 (t, 3H, J=6.8 Hz), 1.10 (dd, 3H, J=6.5, 10.7 Hz); ES/MS calcd. for $C_{37}H_{46}N_7O_5^+$ 668.4. found m/z=668.3 (M+H)$^+$.

Example 2

N-[[1,6-Diethyl-4-[(tetrahydro-2H-pyran-4-yl)amino]-1H-pyrazolo[3,4-b]pyridin-5-yl]methyl]-3-[2-[[(R)-2-hydroxy-2-[4-hydroxy-3-(hydroxymethyl)phenyl]ethyl]amino]propyl]benzamide

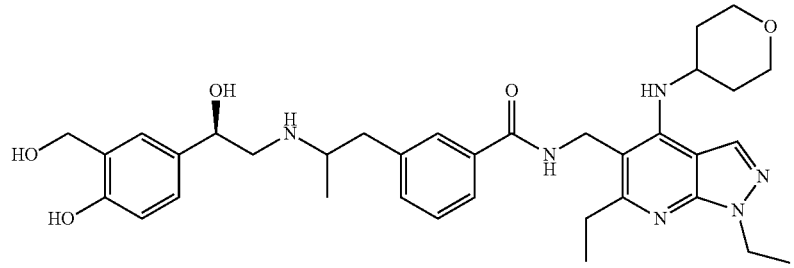 [SMILES: CCc1nc2c(cnn2CC)c(NC2CCOCC2)c1CNC(=O)c1cccc(CC(C)NC[C@H](O)c2ccc(O)c(CO)c2)c1]

The title compound was synthesized in a manner analogous to that described in Intermediate 3, using Intermediate 43 as substrate.

$^1$H NMR (400 MHz, DMSO-d6) δ 9.44 (brs, 1H), 9.17 (brs, 1H), 8.80 (brs, 1H), 8.64 (brs, 1H), 8.34 (s, 1H), 7.74 (m, 2H), 7.46 (m, 2H), 7.36 (s, 1H), 7.09 (dd, 1H, J=1.5, 8.9 Hz), 6.77 (d, 1H, J=8.2 Hz), 6.06 (m, 1H), 4.82 (m, 1H), 4.57 (d, 2H, J=6.5 Hz), 4.50 (s, 1H), 4.45 (dd, 2H, J=6.2, 13.5 Hz), 4.30 (m, 1H), 3.88 (m, 3H), 3.61 (t, 2H, J=11.5 Hz), 3.48 (m, 2H), 3.30 (m, 1H), 3.09 (m, 4H), 2.70 (m, 1H), 1.95 (m, 2H), 1.66 (m, 2H), 1.37 (t, 3H, J=7.1 Hz), 1.30 (t, 3H, J=7.5 Hz), 1.09 (m, 3H); ES/MS calcd. for $C_{35}H_{47}N_6O_5^+$ 631.4. found m/z=631.3 (M+H)$^+$.

Example 3

(R)—N-[[1,6-Diethyl-4-[(tetrahydro-2H-pyran-4-yl)amino]-1H-pyrazolo[3,4-b]pyridin-5-yl]methyl]-3-[2-[[2-hydroxy-2-[4-hydroxy-3-(hydroxymethyl)phenyl]ethyl]amino]-2-methylpropyl]benzamide

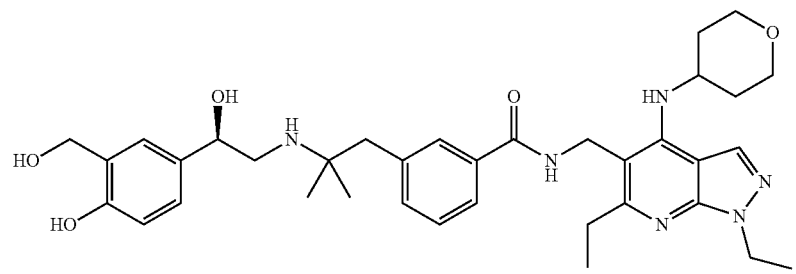 [SMILES: CCc1nc2c(cnn2CC)c(NC2CCOCC2)c1CNC(=O)c1cccc(CC(C)(C)NC[C@H](O)c2ccc(O)c(CO)c2)c1]

The title compound was synthesized in a manner analogous to that described in Intermediate 2, using Intermediate 53 as substrate.

$^1$H NMR (400 MHz, DMSO-d6) δ 9.44 (brs, 1H), 9.10 (brs, 1H), 8.66 (brs, 1H), 8.53 (brs, 1H), 8.30 (brs, 1H), 7.80 (d, 1H, J=7.7 Hz), 7.73 (s, 1H), 7.47 (m, 2H), 7.39 (d, 1H, J=1.9 Hz), 7.13 (dd, 1H, J=2.0, 8.1 Hz), 6.79 (d, 1H, J=8.2 Hz), 6.08 (m, 1H), 4.79 (m, 1H), 4.58 (d, 1H, J=6.0 Hz), 4.51 (s, 1H), 4.42 (m, 2H), 4.28 (m, 1H), 3.89 (m, 2H), 3.78-2.78 (m, 11H), 1.95 (m, 2H), 1.63 (m, 2H), 1.37 (t, 3H, J=7.1 Hz), 1.30 (t, 3H, J=7.4 Hz), 1.20 (s, 6H); ES/MS calcd. for $C_{36}H_{49}N_6O_5^+$ 645.4. found m/z=645.4 (M+H)$^+$.

Example 4

(R)—N-[[1,6-Diethyl-4-[(tetrahydro-2H-pyran-4-yl)amino]-1H-pyrazolo[3,4-b]pyridin-5-yl]methyl]-3-[2-[[2-hydroxy-2-(8-hydroxy-2-oxo-1,2-dihydroquinolin-5-yl)ethyl]-amino]-2-methylpropyl]benzamide

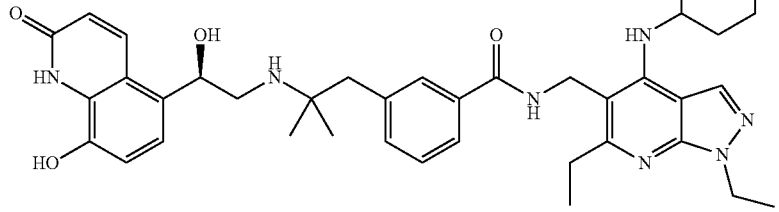

The title compound was synthesized in a manner analogous to that described in Intermediate 2, using Intermediate 54 as substrate.

$^1$H NMR (400 MHz, DMSO-d6) δ 10.31 (brs, 1H), 8.80 (t, 1H, J=6.1 Hz), 8.19 (d, 1H, J=10.0 Hz), 8.01 (s, 1H), 7.67 (m, 2H), 7.30 (m, 2H), 7.07 (t, 2H, J=7.6 Hz), 6.90 (d, 1H, J=8.1 Hz), 6.50 (d, 1H, J=9.9 Hz), 5.29 (m, 1H), 4.94 (m, 1H), 4.55 (d, 2H, J=6.2 Hz), 4.32 (q, 2H, J=7.2 Hz), 4.11 (m, 1H), 3.85 (m, 2H, J=7.9 Hz), 3.54 (t, 2H, J=11.3 Hz), 3.32 (m, 2H), 3.16 (m, 1H), 2.95 (m, 2H), 2.86-2.54 (m, 3H), 1.91 (d, 2H, J=15.5 Hz), 1.54 (m, 3H), 1.34 (t, 3H, J=7.0 Hz), 1.24 (t, 3H, J=7.3 Hz), 0.92 (m, 6H, J=5.7 Hz); ES/MS calcd. for $C_{38}H_{48}N_{17}O_5^+$ 682.3. found m/z=682.4 (M+H)$^+$.

Example 5

(R)—N-[[1,6-Diethyl-4-[(tetrahydro-2H-pyran-4-yl)amino]-1H-pyrazolo[3,4-b]pyridin-5-yl]methyl]-3-[[[2-hydroxy-2-(8-hydroxy-2-oxo-1,2-dihydroquinolin-5-yl)ethyl]amino]methyl]benzamide

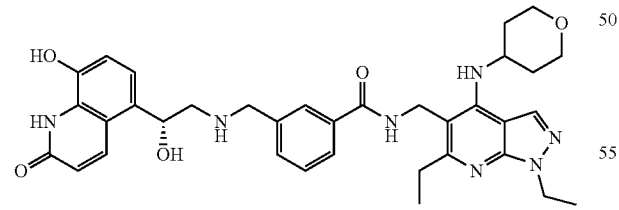

The title compound was synthesized in a manner analogous to that described for Intermediate 43, using Intermediate 4 in place of Intermediate 8 and Intermediate 30 in place of Intermediate 29.

$^1$H NMR (400 MHz, DMSO-d6) δ 8.88 (t, 1H, J=5.9 Hz), 8.10 (d, 1H, J=10.0 Hz), 8.01 (s, 1H), 7.82 (s, 1H), 7.71 (d, 1H, J=9.1 Hz), 7.47 (d, 1H, J=7.6 Hz), 7.39 (t, 1H, J=7.6 Hz), 7.10 (d, 1H, J=7.7 Hz), 7.04 (d, 1H, J=8.2 Hz), 6.88 (d, 1H, J=8.1 Hz), 6.44 (d, 1H, J=9.9 Hz), 5.32 (brs, 1H), 5.05 (dd, 1H, J=4.5, 8.2 Hz), 4.55 (d, 2H, J=6.1 Hz), 4.32 (q, 2H, J=7.2 Hz), 4.10 (m, 1H), 3.86 (s, 2H), 3.78 (s, 2H), 3.55 (m, 2H), 3.32 (m, 3H), 2.98 (q, 2H, J=7.4 Hz), 2.65 (m, 2H), 1.91 (m, 2H), 1.54 (m, 2H), 1.34 (t, 3H, J=7.2 Hz), 1.26 (t, 3H, J=7.5 Hz); ES/MS calcd. for $C_{35}H_{42}N_7O_5^+$ 640.3. found m/z=640.3 (M+H)$^+$.

Example 6

(R)—N-[[1,6-diethyl-4-[(tetrahydro-2H-pyran-4-yl)amino]-1H-pyrazolo[3,4-b]pyridin-5-yl]methyl]-4-[[[2-hydroxy-2-(8-hydroxy-2-oxo-1,2-dihydroquinolin-5-yl)ethyl]amino]methyl]benzamide

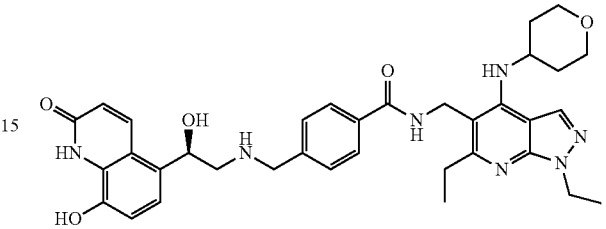

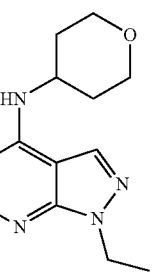

The title compound was synthesized in a manner analogous to that described for Intermediate 43, using Intermediate 4 in place of Intermediate 8 and Intermediate 31 in place of Intermediate 29.

$^1$H NMR (400 MHz, DMSO-d6) δ 8.85 (t, 1H, J=5.9 Hz), 8.11 (d, 1H, J=10.0 Hz), 8.01 (s, 1H), 7.80 (d, 2H, J=8.3 Hz), 7.40 (d, 2H, J=8.4 Hz), 7.12 (d, 1H, J=7.9 Hz), 7.04 (d, 1H, J=8.2 Hz), 6.88 (d, 1H, J=8.1 Hz), 6.44 (d, 1H, J=9.9 Hz), 5.33 (brs, 1H), 5.05 (dd, 1H, J=4.1, 8.1 Hz), 4.54 (d, 2H, J=5.9 Hz), 4.32 (q, 2H, J=7.2 Hz), 4.11 (m, 1H), 3.87 (m, 2H), 3.78 (s, 2H), 3.55 (td, 2H, J=2.1, 11.4 Hz), 3.33 (m, 3H), 2.97 (q, 2H, J=7.4 Hz), 2.65 (m, 2H), 1.91 (m, 2H), 1.53 (m, 2H), 1.34 (t, 3H, J=7.2 Hz), 1.26 (t, 3H, J=7.5 Hz); ES/MS calcd. for $C_{35}H_{42}N_7O_5^+$ 640.3. found m/z=640.3 (M+H)$^+$.

Example 7

(R)—N-[[1,6-Diethyl-4-[(tetrahydro-2H-pyran-4-yl)amino]-1H-pyrazolo[3,4-b]pyridin-5-yl]methyl]-3-[[[2-hydroxy-2-[4-hydroxy-3-(hydroxymethyl)phenyl]ethyl]amino]methyl]benzamide

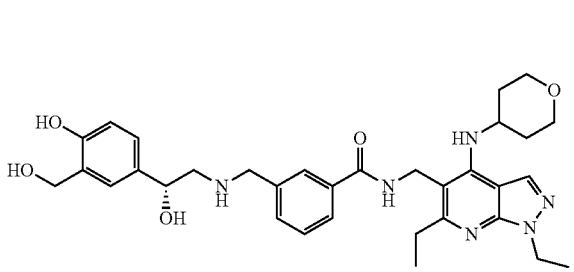 [SMILES: CCc1nc2c(cnn2CC)c(NC2CCOCC2)c1CNC(=O)c1cccc(CNC[C@H](O)c2ccc(O)c(CO)c2)c1]

The title compound was synthesized in a manner analogous to that described for Intermediate 3, using HF pyridine in place of TBAF and Intermediate 45 as a substrate.

¹H NMR (400 MHz, DMSO-d6) δ 9.24 (brs, 1H), 8.91 (t, 1H, J=6.0), 8.01 (s, 1H), 7.85 (s, 1H), 7.74 (d, 1H, J=7.8), 7.52 (d, 1H, J=7.6), 7.42 (t, 1H, J=7.7), 7.24 (d, 1H, J=2.0), 7.10 (d, 1H, J=7.8), 6.97 (dd, 1H, J=2.2, 8.2), 6.68 (d, 1H, J=8.2), 4.93 (m, 1H), 4.59 (m, 1H), 4.55 (d, 2H, J=5.9), 4.45 (s, 2H), 4.33 (q, 2H, J=7.2), 4.12 (m, 1H), 3.85 (s, 3H), 3.55 (td, 2H, J=2.1, 11.4), 3.34 (brs, 3H), 2.98 (q, 2H, J=7.4), 2.62 (m, 2H), 1.91 (m, 2H), 1.54 (m, 2H), 1.34 (t, 3H, J=7.2), 1.26 (t, 3H, J=7.5); ES/MS calcd. for $C_{33}H_{43}N_6O_5^+$ 603.3. found m/z=603.3 (M+H)⁺.

Example 8

(R)—N-[[1,6-diethyl-4-[(tetrahydro-2H-pyran-4-yl)amino]-1H-pyrazolo[3,4-b]pyridin-5-yl]methyl]-4-[[[2-hydroxy-2-[4-hydroxy-3-(hydroxymethyl)phenyl]ethyl]amino]methyl]benzamide

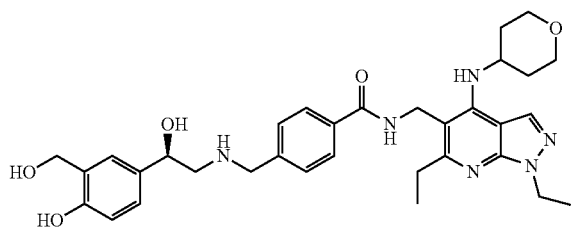 [SMILES: CCc1nc2c(cnn2CC)c(NC2CCOCC2)c1CNC(=O)c1ccc(CNC[C@H](O)c2ccc(O)c(CO)c2)cc1]

The title compound was synthesized in a manner analogous to that described for Intermediate 3, using HF Pyridine in place of TBAF and Intermediate 46 as a substrate.

¹H NMR (400 MHz, DMSO-d6) δ 9.19 (brs, 1H), 8.87 (t, 1H, J=5.8), 8.01 (s, 1H), 7.82 (d, 2H, J=8.4), 7.44 (d, 2H, J=8.3), 7.24 (d, 1H, J=2.0), 7.11 (d, 1H, J=7.7), 6.96 (dd, 1H, J=2.2, 8.2), 6.68 (d, 1H, J=8.2), 4.91 (m, 1H), 4.54 (m, 3H, J=6.0), 4.44 (s, 2H), 4.32 (q, 2H, J=7.2), 4.11 (m, 1H), 3.84 (s, 3H), 3.56 (td, 2H, J=1.9, 11.2), 3.34 (m, 3H), 2.97 (q, 2H, J=7.5), 2.60 (s, 2H), 1.91 (s, 2H), 1.53 (m, 2H), 1.34 (t, 3H, J=7.2), 1.26 (t, 3H, J=7.5); ES/MS calcd. for $C_{33}H_{43}N_6O_5^+$ 603.3. found m/z=603.3 (M+H)⁺.

Example 9

(R)—N-[[1,6-diethyl-4-[(tetrahydro-2H-pyran-4-yl)amino]-1H-pyrazolo[3,4-b]pyridin-5-yl]methyl]-4-[5-[[2-hydroxy-2-(8-hydroxy-2-oxo-1,2-dihydroquinolin-5-yl)ethyl]amino]pentyl]benzamide

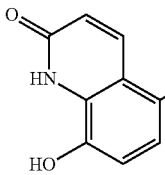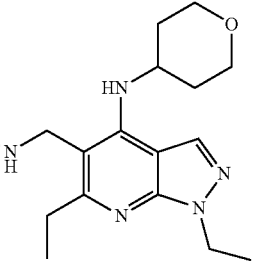

The title compound was synthesized in a manner analogous to that described for Intermediate 3, using Intermediate 44 as substrate.

¹H NMR (400 MHz, DMSO-d6) δ 10.58-10.39 (m, 2H), 9.19-8.95 (m, 2H), 8.68-8.45 (m, 2H), 8.42-8.25 (s, 1H), 8.14 (d, J=9.99 Hz, 1H), 7.81 (d, J=8.28 Hz, 2H), 7.33 (d, J=8.24 Hz, 2H), 7.14 (d, J=8.21 Hz, 1H), 6.98 (d, J=8.17 Hz, 1H), 6.65-6.51 (m, 1H), 6.29-6.04 (s, 1H), 5.41-5.21 (m, 1H), 4.56 (d, J=6.14 Hz, 2H), 4.49-4.36 (m, 2H), 4.36-4.19 (m, 1H), 3.99-3.82 (m, 2H), 3.72-3.53 (m, 2H), 3.19-2.86 (m, 6H), 2.64 (m, 2H), 2.07-1.86 (m, 2H), 1.79-1.51 (m, 6H), 1.34 (m, J=30.50, 7.39 Hz, 7H); ES/MS calcd. for $C_{39}H_{50}N_7O_5^+$ 696.4. found m/z=696.4 (M+H)⁺.

Example 10

(R)—N-[[1,6-Diethyl-4-[(tetrahydro-2H-pyran-4-yl)amino]-1H-pyrazolo[3,4-b]pyridin-5-yl]methyl]-8-[[2-hydroxy-2-(8-hydroxy-2-oxo-1,2-dihydroquinolin-5-yl)ethyl]amino]octanamide

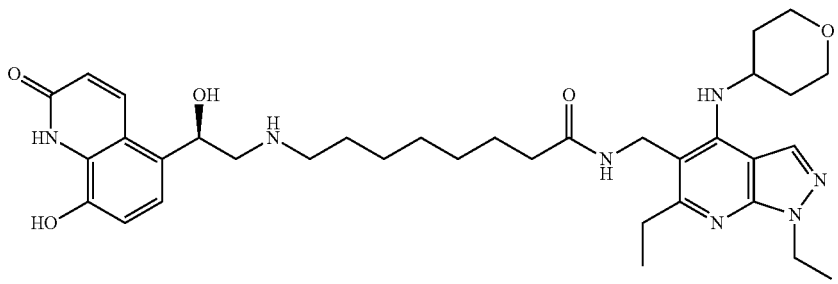 [SMILES: CCc1nc2c(cnn2CC)c(NC2CCOCC2)c1CNC(=O)CCCCCCCNC[C@H](O)c1ccc(O)c2[nH]c(=O)ccc12]

The title compound was synthesized in a manner analogous to that described in Intermediate 3, using Intermediate 55 as substrate.

¹H NMR (400 MHz, DMSO-d6) δ 10.65 (brs, 2H), 8.65 (brs, 1H), 8.59 (brs, 2H), 8.33 (brs, 1H), 8.15 (d, 1H, J=10 Hz), 7.14 (d, 1H, J=8 Hz), 6.98 (d, 1H, J=8 Hz), 6.20 (brs, 1H), 5.30 (d, 1H, J=8.8 Hz), 4.42 (m, 3H), 4.35 (d, 2H, J=6 Hz), 4.25 (brs, 1H), 3.9 (m, 3H), 3.60 (t, 2H, J=11.2 Hz), 3.18-2.9 (m, 6H), 2.15 (t, 2H, J=7.2 Hz), 1.95 (m, 2H), 1.6-1.5 (m, 6H), 1.35 (t, 3H, J=7.2 Hz), 1.22 (M, 8H); ES/MS calcd. for $C_{36}H_{60}N_7O_6^+$ 648.4. found m/z=649.0 (M+H)$^+$.

Example 11

(R)-1-(1,6-diethyl-4-((tetrahydro-2H-pyran-4-yl)amino)-1H-pyrazolo[3,4-b]pyridin-5-yl)methyl)-3-(4-(5-((2-hydroxy-2-(8-hydroxy-2-oxo-1,2-dihydroquinolin-5-yl)ethyl)amino)pent-1-yn-1-yl)phenyl)urea

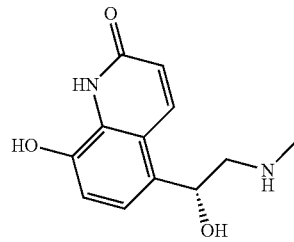
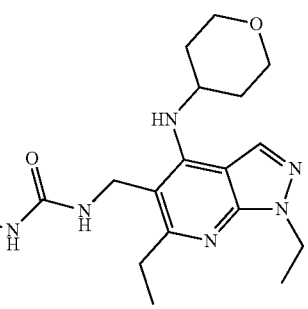

A solution of Intermediate 56 (0.16 g, 0.19 mmol) in tetrahydrofuran (2 mL) was treated successively with TBAF solution (1.0 M in THF, 2 mL) and glacial acetic acid (0.60 mL). The mixture was stirred overnight at room temperature and then concentrated to dryness under reduced pressure. The residue was purified by reverse-phase high performance liquid chromatography (RP-HPLC, acetonitrile/water/0.1% TFA) to provide, after concentration, the trifluoroacetic acid salt of the title compound as a white powder (80 mg).

$^1$H NMR (400 MHz, DMSO-d6) δ 11.44 (bs, 1H), 10.49 (s, 1H), 9.26 (s, 1H), 8.90 (bs, 1H), 8.67 (s, 1H), 8.35 (s, 1H), 8.17 (d, J=10.0 Hz, 1H), 7.42 (d, J=8.8 Hz, 2H), 7.30 (d, J=8.4 Hz, 2H), 7.16 (d, J=8.4 Hz, 1H), 6.99 (d, J=8.0 Hz, 1H), 6.58 (d, J=10.0 Hz, 1H), 6.65-6.51 (m, 1H), 6.24-6.09 (bs, 1H), 5.31 (m, 1H), 4.41 (m, 2H), 4.37-4.22 (m, 1H), 3.93-3.85 (m, 2H), 3.83-3.75 (m, 2H), 3.68-3.57 (m, 2H), 3.55-3.48 (m, 2H), 3.10-2.96 (m, 6H), 2.07-1.82 (m, 2H), 1.75-1.61 (m, 4H), 1.38 (t, J=7.2 Hz, 3H), 1.30 (t, J=7.6 Hz, 3H); ES/MS calcd. for $C_{39}H_{47}N_8O_6^+$ 707.4. found m/z=707.5 (M+H)$^+$.

Example 12

(R)-1-((1,6-diethyl-4-((tetrahydro-2H-pyran-4-yl)amino)-1H-pyrazolo[3,4-b]pyridin-5-yl)methyl)-3-(4-(5-((2-hydroxy-2-(8-hydroxy-2-oxo-1,2-dihydroquinolin-5-yl)ethyl)amino)pentyl)phenyl)urea

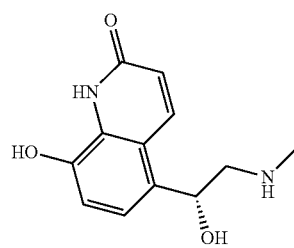
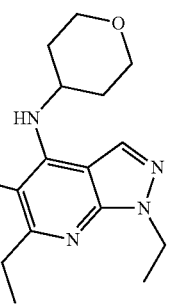

A solution of the trifluoroacetic acid salt of Example 11 (60 mg) in methanol (4 mL) and ethyl acetate (1 mL) was treated with palladium on carbon (10% w/w, 10 mg) and then stirred for one hour under a balloon of hydrogen gas. The mixture was filtered through a pad of Celite diatomaceous earth, and then the filtrate was concentrated under reduced pressure to provide the trifluoroacetic acid salt of the title compound as a pale golden glass, which was scraped into a powder (27 mg).

$^1$H NMR (400 MHz, DMSO-d6) δ 10.55-10.48 (m, 2H), 9.83 (s, 1H), 8.82-8.74 (m, 2H), 8.54 (s, 1H), 8.29 (bs, 1H), 8.15 (d, J=10.0 Hz, 1H), 7.32 (d, J=8.4 Hz, 2H), 7.14 (d, J=8.0 Hz, 1H), 7.08 (d, J=8.4 Hz, 2H), 6.98 (d, J=8.0 Hz, 1H), 6.65-6.51 (d, J=9.6 Hz, 1H), 6.19-6.10 (bs, 1H), 5.29 (m, 1H), 4.56 (d, J=6.14 Hz, 2H), 4.48-4.33 (m, 2H), 4.32-4.20 (m, 1H), 3.93-3.83 (m, 2H), 3.65-3.55 (m, 2H), 3.47-3.42 (m, 2H), 3.18-2.86 (m, 6H), 2.64 (m, 2H), 2.05-1.92 (m, 2H), 1.74-1.51 (m, 6H), 1.34 (m, 7H); ES/MS calcd. for $C_{39}H_{51}N_8O_5^+$ 711.4. found m/z=711.4 (M+H)$^+$.

Example 13

(R)-3-(((1,6-diethyl-4-((tetrahydro-2H-pyran-4-yl)amino)-1H-pyrazolo[3,4-b]pyridin-5-yl)methyl)amino)-4-((4-(5-((2-hydroxy-2-(8-hydroxy-2-oxo-1,2-dihydroquinolin-5-yl)ethyl)amino)pentyl)phenyl)amino)cyclobut-3-ene-1,2-dione

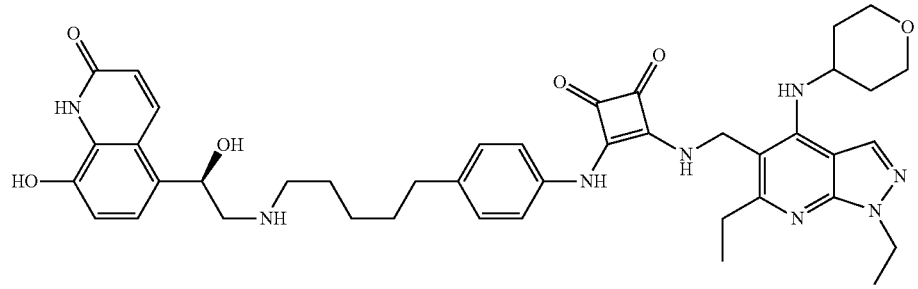 [SMILES: CCc1nc2c(cnn2CC)c(NC2CCOCC2)c1CNc1c(Nc2ccc(CCCCCNC[C@H](O)c3ccc(O)c4[nH]c(=O)ccc34)cc2)c(=O)c1=O]

A mixture of Intermediate 38 (0.11 g, 0.19 mmol) and Intermediate 28 (0.15 g, 0.36 mmol) in ethanol (2 mL) was heated for 3 days in a 70° C. oil bath. The mixture was concentrated under reduced pressure and was then purified by automated flash silica gel chromatography, using a 12 g Silicycle SiliSep flash column (dichloromethane/methanol) to give the impure intermediate, (R)-tert-butyl 2-(tert-butyldimethylsilyloxy)-2-(8-hydroxy-2-oxo-1,2-dihydroquinolin-5-yl)ethyl(5-(4-(2-(((1,6-diethyl-4-(tetrahydro-2H-pyran-4-ylamino)-1H-pyrazolo[3,4-b]pyridin-5-yl)methylamino)-3,4-dioxocyclobut-1-enylamino)phenyl)pent-4-ynyl)carbamate. This material was then subjected to reverse-phase high performance liquid chromatography (RP-HPLC, acetonitrile/water/0.1 TFA) to provide, after concentration, the intermediate (R)-tert-butyl 5-(4-(2-(((1,6-diethyl-4-(tetrahydro-2H-pyran-4-ylamino)-1H-pyrazolo[3,4-b]pyridin-5-yl)methylamino)-3,4-dioxocyclobut-1-enylamino)phenyl)pent-4-ynyl(2-hydroxy-2-(8-hydroxy-2-oxo-1,2-dihydroquinolin-5-yl)ethyl)carbamate. This intermediate was dissolved in methanol (5 mL) and treated with palladium on carbon (10% w/w, wet Degussa-type, catalytic amount). The suspension was stirred under a balloon of hydrogen gas until LC/MS analysis indicated the complete reduction of the triple bond. The mixture was then filtered through a pad of Celite diatomaceous earth, and the filtrate was concentrated to dryness under reduced pressure. The residue was taken up in dichloromethane/methanol (1:1, 5 mL) and treated with a solution of hydrogen chloride in dioxane (4 N, 2 mL). Once LC/MS analysis showed the complete removal of the Boc-protecting group, the mixture was concentrated to dryness. The residue was purified by reverse-phase high performance liquid chromatography (RP-HPLC, acetonitrile/water/0.1% TFA) to provide, after concentration, the trifluoroacetic acid salt of the title compound as a pale yellow powder (28 mg).

$^1$H NMR (400 MHz, DMSO-d6) δ 10.50-10.46 (m, 2H), 9.81 (s, 1H), 8.53 (m, 2H), 8.28 (bs, 1H), 8.15 (d, J=9.6 Hz, 1H), 7.85 (m, 1H), 7.36 (d, J=8.4 Hz, 2H), 7.13-7.17 (m, 3H), 6.98 (d, J=8.0 Hz, 1H), 6.58 (d, J=10.0 Hz, 1H), 6.24-6.04 (bs, 1H), 5.29 (m, 1H), 4.94 (d, J=5.2 Hz, 2H), 4.42 (m, 2H), 4.30-4.18 (m, 1H), 3.92-3.85 (m, 2H), 3.59 (m, 2H), 3.18-2.86 (m, 6H), 2.54 (m, 2H), 2.06-1.88 (m, 2H), 1.79-1.51 (m, 6H), 1.33 (m, 7H); ES/MS calcd. for $C_{42}H_{51}N_8O_6^+$ 763.4. found m/z=763.3 (M+H)$^+$.

Example 14

(R)-1-(((1,6-diethyl-4-((tetrahydro-2H-pyran-4-yl)amino)-1H-pyrazolo[3,4-b]pyridin-5-yl)methyl)-3-(4-(4-((6-(((2-hydroxy-2-(8-hydroxy-2-oxo-1,2-dihydroquinolin-5-yl)ethyl)amino)hexyl)oxy)butyl)phenyl)urea

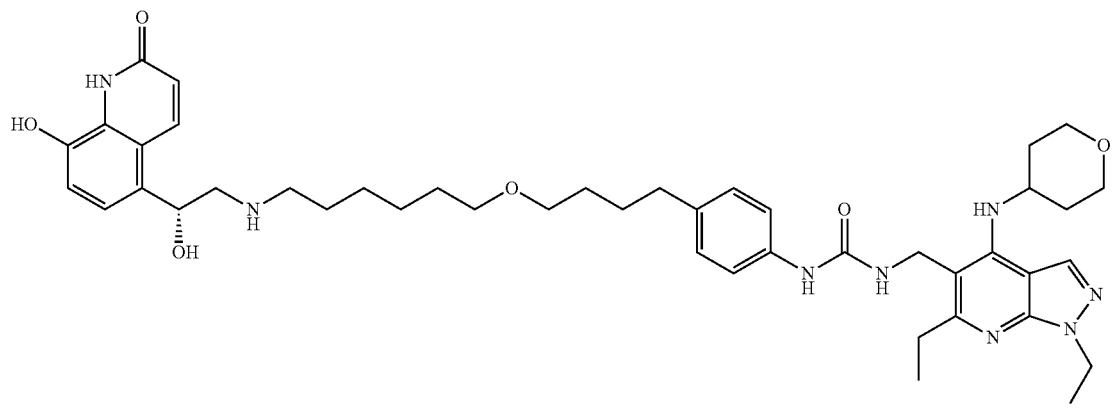 [SMILES: CCc1nc2c(cnn2CC)c(NC2CCOCC2)c1CNC(=O)Nc1ccc(CCCCOCCCCCCNC[C@H](O)c2ccc(O)c3[nH]c(=O)ccc23)cc1]

The crude concentrated reaction mixture containing Intermediate 57 was taken up in methanol (approximately 0.50 mL) and treated with a solution of hydrogen chloride in dioxanes (4 N, 2 mL). The mixture was subsequently concentrated to dryness under reduced pressure. The residue was purified by reverse-phase high performance liquid chromatography (RP-HPLC, acetonitrile/water/0.1% TFA) to provide, after concentration, the trifluoroacetic acid salt of the title compound as a powder (107 mg, 58% over two steps).

$^1$H NMR (400 MHz, DMSO-$d_6$) δ 10.48 (m, 2H), 8.82 (s, 1H), 8.54 (m, 2H), 8.32 (s, 1H), 8.15 (d, J=10.0 Hz, 1H), 7.31 (d, J=8.4 Hz, 2H), 7.14 (d, J=8.4 Hz, 1H), 7.07 (d, J=8.4 Hz, 2H), 6.98 (d, J=8.4 Hz, 1H), 6.58 (d, J=9.9 Hz, 1H), 6.15 (s, 1H), 5.30 (d, J=8.1 Hz, 1H), 4.44-4.22 (m, 6H), 3.91 (m, 2H), 3.60 (m, 3H), 3.33 (m, 4H), 3.14-2.88 (m, 8H), 2.02-1.91 (m, 2H), 1.78-1.42 (m, 8H), 1.40-1.34 (m, 4H), 1.32-1.24 (m, 8H); ES/MS calcd. for $C_{44}H_{61}N_8O_6^+$ 797.5. found m/z=797.4 (M+H)$^+$.

Example 15

(R)-1-(1,6-diethyl-4-((tetrahydro-2H-pyran-4-yl)amino)-1H-pyrazolo[3,4-b]pyridin-5-yl)methyl)-3-(4-(5-((2-hydroxy-2-(5-hydroxy-3-oxo-3,4-dihydro-2H-benzo[b][1,4]oxazin-8-yl)ethyl)amino)pent-1-yn-1-yl)phenyl)urea

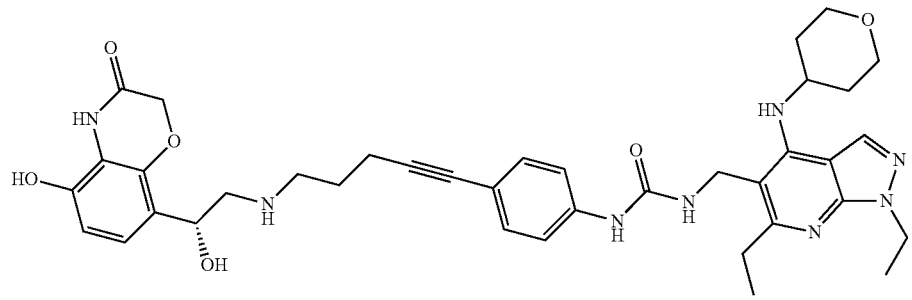 [SMILES: CCc1nc2c(cnn2CC)c(NC2CCOCC2)c1CNC(=O)Nc1ccc(C#CCCCNC[C@H](O)c2ccc(O)c3c2OCC(=O)N3)cc1]

The title compound was prepared in a manner analogous to that described for Example 11, using Intermediate 58 as a substrate.

$^1$H NMR (400 MHz, DMSO-$d_6$) δ 10.05-9.96 (m, 2H), 9.19-8.70 (bs, 2H), 8.63-8.56 (m, 2H), 8.48-8.25 (bs, 1H), 7.41 (d, J=8.4 Hz, 2H), 7.30 (d, J=8.9 Hz, 2H), 6.92 (d, J=8.0 Hz, 1H), 6.56 (d, J=8.8 Hz, 1H), 5.94 (s, 1H), 5.07 (d, J=9.3 Hz, 2H), 5.94 (s, 1H), 5.06 (d, J=9.2 Hz, 1H), 4.58-4.49 (m, 4H), 4.49-4.32 (m, 2H), 4.32-4.19 (m, 1H), 3.91-3.88 (m, 2H), 3.63-3.53 (m, 2H), 3.14-2.86 (m, 6H), 2.68 (m, 2H), 2.07-1.86 (m, 2H), 1.72-1.56 (m, 2H), 1.37 (t, J=7.2 Hz, 3H), 1.29 (t, J=7.6 Hz, 3H); ES/MS calcd. for $C_{38}H_{47}N_8O_6^+$ 711.4. found m/z=711.3 (M+H)$^+$.

Examples 16-20 may be prepare using the general methods described above.

Example 16

(R)-1-Ethyl-N-[4'-[[[2-(3-formamido-4-hydroxyphenyl)-2-hydroxyethyl]amino]methyl]biphenyl-4-yl]-4-[(tetrahydro-2H-pyran-4-yl)amino]-1H-pyrazolo[3,4-b]pyridine-5-carboxamide

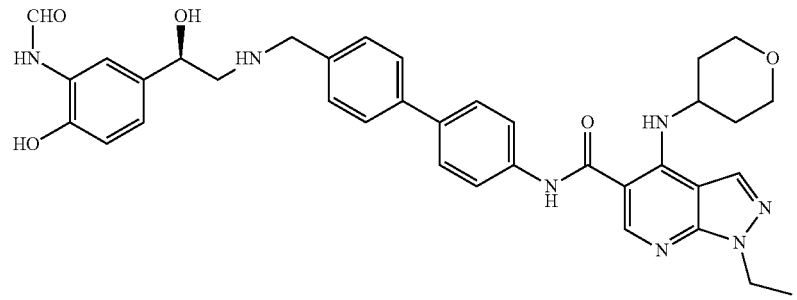 [SMILES: CCn1ncc2c(NC3CCOCC3)c(C(=O)Nc3ccc(-c4ccc(CNC[C@H](O)c5ccc(O)c(NC=O)c5)cc4)cc3)cnc21]

Example 17

(R)-8-[2-[2-[4-[1-Ethyl-4-(tetrahydro-2H-pyran-4-ylamino)-1H-pyrazolo[3,4-b]pyridine-5-carbonyl]piperazin-1-yl]ethylamino]-1-hydroxyethyl]-5-hydroxy-2H-benzo[b][1,4]oxazin-3(4H)-one

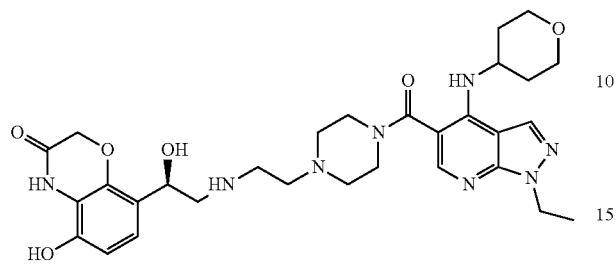

Example 18

(R)—N-[[1,6-diethyl-4-(tetrahydro-2H-pyran-4-ylamino)-1H-pyrazolo[3,4-b]pyridin-5-yl]methyl]-6-[4-[2-hydroxy-2-(8-hydroxy-2-oxo-1,2-dihydroquinolin-5-yl)ethylamino]butoxy]nicotinamide

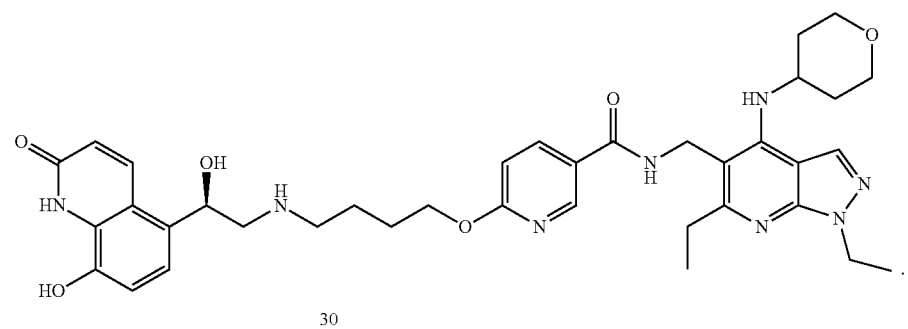

Example 19

(R)—N-((1,6-diethyl-4-((tetrahydro-2H-pyran-4-yl)amino)-1H-pyrazolo[3,4-b]pyridin-5-yl)methyl)-4-(5-((2-hydroxy-2-(4-hydroxy-3-(methylsulfonamido)phenyl)ethyl)amino)pentyl)benzamide

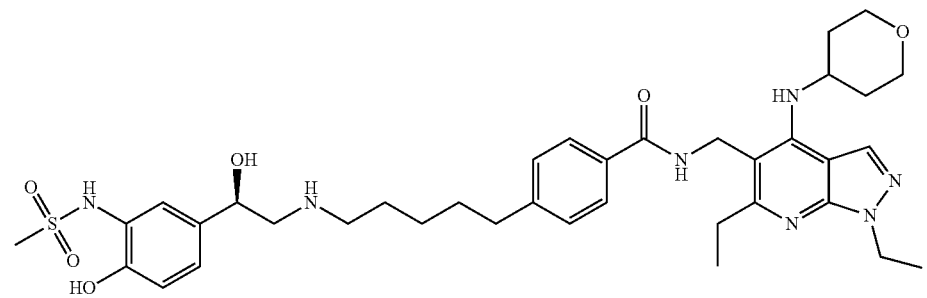 [SMILES: CCc1nc2c(cnn2CC)c(NC2CCOCC2)c1CNC(=O)c1ccc(CCCCCNC[C@H](O)c2ccc(O)c(NS(C)(=O)=O)c2)cc1]

Example 20

(R)-6-((2-hydroxy-2-(8-hydroxy-2-oxo-1,2-dihydroquinolin-5-yl)ethyl)amino)hexyl((1,6-diethyl-4-((tetrahydro-2H-pyran-4-yl)amino)-1H-pyrazolo[3,4-b]pyridin-5-yl)methyl)carbamate

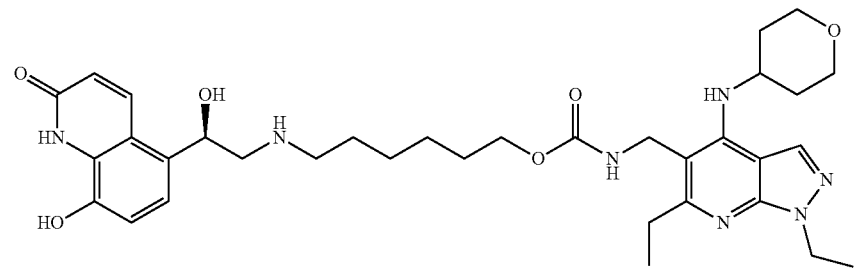 [SMILES: CCc1nc2c(cnn2CC)c(NC2CCOCC2)c1CNC(=O)OCCCCCCNC[C@H](O)c1ccc(O)c2[nH]c(=O)ccc12]

Biological Examples

Inhibition of PDE4B4 Enzyme Activity

The inhibitory activity of test compounds were determined using the PDE Glo Assay (Promega, V1361). The PDE-Glo Reaction Buffer was prepared (1 mL 5× buffer+4 mL water) and 150 nM solution of test compound dissolved in the Reaction Buffer, followed by 1:3 serial dilutions into Reaction Buffer. DMSO was used for the initial dilution of test compounds and the final concentration used in the assay did not exceed 0.1% DMSO. Human recombinant PDE4B2 (BPS Bioscience) was added to test compound in Reaction Buffer at a concentration of 0.12 nM per reaction. The enzyme and test compound were pre-incubated together at rt for 10 min. 50 nM of the enzyme substrate cAMP was then added to initiate the enzyme reaction, with the reaction terminated after one hour. Termination Buffer (1 mL 5× termination buffer+3.9 mL water+100 µL of 100 mM IBMX (ICN Chemicals, in DMSO)), was added to each reaction well to terminate the reaction. Detection Buffer (1 mL 5×PDE-Glo Detection buffer+3.96 mL water+40 µL PKA (supplied in kit)) was added to the cAMP-enzyme-test compound mix and this secondary reaction proceeded for 20 minutes at rt. An equal volume of Kinase Glo Reagent was then added to the reaction mixture and after 10 min luminescence was measured using a luminometer (EnVision, 0.1 sec read for luminescence). Luminescence values were directly related to levels of cAMP in the reaction mixture. Data were plotted as relative light units (RLU) versus test compound concentration and the $IC_{50}$ determined using GraphPad Prism 5.0, using a nonlinear curve fit in a single-site binding model.

IC50 determinations for the compounds presented above are seen in the first column of Table 1 (PDE4 IC50).

Beta-2 Adrenoceptor Binding Assay

Test compounds were incubated for 120 min with Chinese hamster oocyte (CHO) cells expressing the human recombinant beta-2 adrenoreceptors. Binding of test compounds to the beta-2 adrenoreceptors was determined by measuring the displacement of the radiolabeled ligand [$^3$H](−)CGP-12177 (0.3 nM) from the receptor measured by a scintillation counting. Concentration response curves were generated for test compounds and the $IC_{50}$ (molar concentration of the compound which produced 50% inhibition for the maximal response for that compound) was determined. These assays were performed using a protocol based on the original description of the assay by Joseph et al., (2004) *Naun.-Sch. Arch. Pharm.*; 369:525-532.

IC50 determinations for the compounds presented above are seen in the second column of Table 1 (Beta 2 IC50).

Functional Agonism of Human Recombinant Beta-2 Adrenoreceptors Expressed in Chinese Hamster Oocytes (CHO)

Test compounds were incubated for 30 min with CHO cells expressing the human recombinant beta-2 adrenoreceptors. Agonism of the receptor was measured by the elevation of intracellular cyclic-AMP over control levels detected using a homogeneous time resolved fluorescence (HTRF) format. Compounds were determined to be "full" or "partial" agonists based on the maximum level of cAMP accumulated compared to the control compound isoproterenol which is a full agonist in this assay system. Concentration response curves were generated for test compounds and the $EC_{50}$ (molar concentration of the agonist which produced 50% of the maximal response for that compound) was determined. These assays were performed using a protocol based on the original description of the assay by Baker, J. G. (2005) *Brit. J. Pharmacol.*; 144:317-322.

EC50 determinations for the compounds presented above are seen in the third column of Table 1 (Beta 2 EC50).

Inhibition of Lipopolysaccharide (LPS)-Induced Tumour Necrosis Factor Alpha (TNF-α) Release from Human Peripheral Blood Mononuclear Cells (PBMC)

Human whole blood was drawn from donors and cell purification initiated within two hours. Peripheral blood mononuclear cells (PBMC) were purified using a standard Ficoll gradient purification technique and aliquoted at a concentration of 100,000 cells/well in 96 well plates. Beta-2 adrenoreceptor agonists are also anti-inflammatory for some immune cells expressing the receptor and in this assay they can inhibit tumor necrosis factor-alpha (TNF-α) production. Therefore PBMC were pre-incubated for 30 min in the presence of the beta-2 adrenoreceptor antagonist ICI-118551 (3-(isopropylamino)-1-[(7-methyl-4-indanyl)oxy]butan-2-ol) (10 µM) to determine the PDE4 directed activity of test compounds, and in the absence of ICI-118551 for the combined PDE4 and beta-2 receptor directed activity. Test compounds were dissolved in DMSO and diluted in buffer (final DMSO concentration of 0.1% v/v) and were then added to the cell suspensions and pre-incubated for a further 1 h at 37° C. LPS solution was then added (0.4 ng/mL) and the cells incubated for a further 6 h. At the end of the incubation period the cell supernatants were collected and TNF-α was measured using a Procarta Cytokine Assay Kit (Affymetrix, Santa Clara, Calif.) according to the manufacturers' instructions. Data were analyzed using MiraiBio Masterplex QT v4.0 software (MasterPlex Version 1.0.1.18 Copyright 2008, Hitachi Software Engineering Co., Ltd) and used to extrapolate Mean Fluorescence Intensity (MFI) into concentrations of TNF-α and mean values from replicate wells were determined. Inhibition curves were plotted using a nonlinear curve fit employing a single-site binding model to determine the $IC_{50}$ value for each test compound in the presence or absence of ICI-118551 using GraphPad Prism 5 for Windows, version 5.02 (GraphPad Software, San Diego Calif.).

EC50 determinations for the compounds presented above are seen in the fourth column of Table 1 (PBMC TNF EC50).

Inhibition of Lipopolysaccharide (LPS)-Induced Neutrophil Recruitment into the Lungs of Lewis Rats Rats are anesthetized with 4% isoflurane, placed in the supine position at an angle of 30°, the mouth opened and the trachea exposed. A 22-gauge needle with a syringe attached is introduced into the trachea and test compound in suspension (200 µl volume per 400 g) is delivered into the lungs from approximately one centimeter above the carina. The rats are allowed to recover and two hrs later conscious animals are placed into a chamber and exposed to aerosolized LPS (1.0 mg/mL) at a rate of 3.0 L/min for 20 min. Rats are euthanized 4 h post-LPS exposure by an overdose of pentobarbital (90 mg/kg) by intra-peritoneal injection. Broncheoalveolar lavage (BAL) was then performed with a 14 gauge blunt needle into the exposed trachea. Five, 5 ml washes of PBS are collect from the lungs and placed into Falcon tubes then centrifuged at 1600 g for 10 min at 4° C. The supernatant is discarded, the cells are re-suspended in PBS and total cell counts are determined based on a 10 µl sample of re-suspended cells stained with trypan blue and counts performed using a Countess® cell counter (Invitrogen). Differential cell counts to determine the number of neutrophils in the BAL wash are performed on cytospun cells stained with May-Grunwald and Giemsa solution. Manual eye counting is performed to determine the percentage number of cells in the cytospun sample (determined as macrophages, neutrophils, eosinophils, T-lymphocytes and eosinophils) and these values are used to determine the total number of each cell type per sample.

Typically experiments contain a minimum of six rats per experimental group and the mean±SEM number of neutrophils is determined for each group. The level of neutrophil inhibition caused by test compounds dosed directly into the lungs is determined compared to the vehicle-treated and LPS-exposed control rats. Statistical analysis to determine significant differences between groups are performed by one-way analysis of variance (ANOVA) using GraphPad Prism 5 for Windows, version 5.02 (GraphPad Software, San Diego Calif.).

The compounds of Examples 1 and 9 were tested in this assay and both exhibited a neutrophil inhibition of greater than 40% at a dose of 300 µg/kg.

Inhibition of Acetylcholine-Induced Bronchoconstriction in Dunkin-Hartley Guinea Pigs Guinea pigs (Dunkin-Hartley from Charles River Laboratories, male, 500 to 800 g) are anesthetized with 4% isoflurane, placed in the supine position at an angle of 30°, the mouth opened and the trachea exposed. A 22-gauge needle with a syringe attached is introduced into the trachea and test compound in suspension (200 µl volume) is delivered into the lungs from approximately one centimeter above the carina. In vivo bronchoprotective effects of the test compounds against acetylcholine (ACh)-induced bronchoconstriction are tested in conscious guinea pigs using a whole body plethysmograph system (WBP) (Buxco Research Systems) 4 hrs after intratracheal dosing of test compounds. The lung function is measured in this system and expressed as an enhanced PAUSE (Penh) which has been widely used in scientific research and preclinical drug screening as a surrogate methodology for measuring lung resistance in conscious animals (Chong et al., *J. Pharmnacol. Toxicol. Methods* 1998; 39:163-168. Pennock et al., *J. Appl. Physiol.* 1979; 46:399-406). Guinea pigs are placed in the WBP system chambers and exposed to aerosol of either 0.9% saline solution or ACh solution (4 mg/mL) for 1 min. Lung function measurements (expressed as Penh and calculated by peak expiratory flow/peak inspiratory flow× pause) are continuously recorded for 20 min immediately after saline or ACh challenge. The results are expressed as area under curves (AUG) of airway response (Penh) over the responding time (20 min). Twenty four hrs before the assessment of test compounds takes place, airway responses of guinea pigs are measured to determine their baseline responses prior to compound treatments. Each animal may therefore act as it's own control for the evaluation of bronchoprotection of test compounds and the efficacy of test compounds are calculated as the percentage inhibition of airway response compared to this value. Assessment of the duration of bronchoprotection could also be determined by re-challenging animals up to 24 hrs post test compound dosing. Typically experiments will contain a minimum of six guinea pigs per experimental group and the mean±SEM inhibition of PenH is determined for each group. Statistical analysis to determine significant differences between groups are performed by one-way analysis of variance (ANOVA) using GraphPad Prism 5 for Windows, version 5.02 (GraphPad Software, San Diego Calif.).

TABLE 1

| Example # | PDE4 IC50 | Beta 2 IC50 | Beta 2 EC50 | PBMC TNF EC50 |
|---|---|---|---|---|
| 1 | ++ | ++ | ++ | ++ |
| 2 | ++ | − | ++ | ++ |
| 3 | ++ | + | + | ++ |
| 4 | ++ | ++ | ++ | ++ |
| 5 | ++ | + | ++ | ++ |
| 6 | ++ | − | ++ | ++ |
| 7 | ++ | − | − | − |
| 8 | ++ | − | − | + |
| 9 | ++ | ++ | ++ | ++ |
| 10 | ++ | − | ++ | ++ |
| 11 | ++ | ++ | ++ | ++ |
| 12 | ++ | ++ | ++ | ++ |
| 13 | ** | ++ | ++ | ++ |
| 14 | ** | ++ | ++ | ++ |
| 15 | ** | ++ | ++ | ++ |

<100 nM = ++
<300 nM = +
>300 nM = −
Not measured = **

Dry Powder Formulation

A dry powder formulation of one or more compounds of the invention for administration by inhalation may be prepared by as follows:

Particles of a compound of the invention (API) are micronized using conventional processes including but not limited to jet milling, to achieve a distribution with a mass median aerodynamic diameter (MMAD) of about 2 and a GSD<about 2.5. The micronized particles are then blended with a conventional dry powder excipient such as lactose. Specific examples of suitable forms of commercially available lactose include Lactohale LH100 which comprises particles>60 micron and Lactohale LH200 which comprises large (>60 microns) lactose particles mixed with lactose "fines" (<10 microns). A typical formulation will include less than 10% API, with the remainder being the dry powder excipient. This bulk formulation can be filled into a multi-dose DPI, e.g. Valois Prohaler, with a fill weight designed to permit emission of the desired dose.

The invention claimed is:

1. A compound of Formula I:

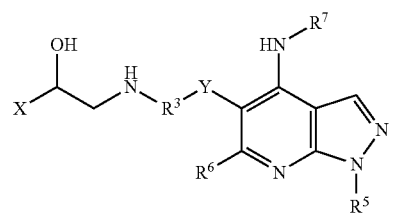

or a pharmaceutically acceptable salt thereof, wherein:

X is selected from:

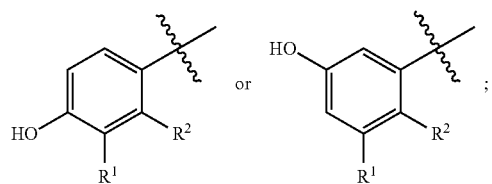

wherein $R^1$ is selected from $CH_2OH$, $CH_2CH_2OH$, $N(H)C(O)H$, and $N(H)S(O_2)CH_3$, and $R^2$ is H;

or X is a bicyclic, fused heterocyclic ring selected from the group of:

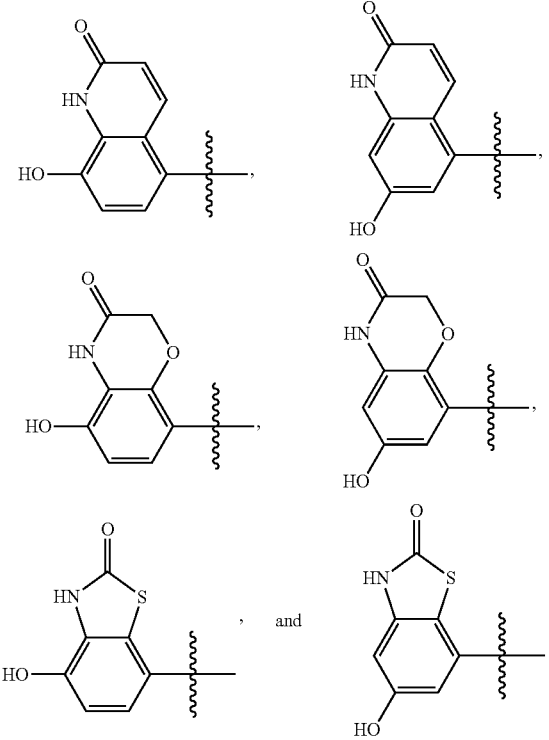

wherein said bicyclic fused heterocyclic ring is optionally substituted with one, two, or three additional substituents independently selected from alkyl, oxo, and OH;

$R^3$ is selected from $C_{4-12}$alkylene, $C_{4-12}$alkenylene, $C_{4-12}$alkynylene, $R^4$—O—$R^4$, $R^4$—N($R^8$)—$R^4$, $C_{3-6}$cycloalkylene, $R^4$—$C_{3-6}$cycloalkylene, $C_{3-6}$cycloalkylene-$R^4$, $R^4$—$C_{3-6}$cycloalkylene-$R^4$, phenylene, $R^4$-phenylene, phenylene-$R^4$, $R^4$-phenylene-$R^4$, $R^4$-phenylene-O—$R^4$, $R^4$-phenylene-N($R^8$)—$R^4$, $R^4$-phenylene-phenylene, Het, $R^4$—Het, $R^4$-Het-phenylene, Het-$R^4$, $R^4$-Het-$R^4$, $R^4$—O-Het $R^4$-phenylene-O-Het, $R^4$phenylene-C(O)—Het, and $R^4$-phenylene-N($R^8$)-Het;

wherein said alkylene, alkenylene, alkynylene, cycloalkylene, or arylene is optionally substituted with 1, 2, or 3 substituents selected from halo, oxo, and $OR^8$;

Het is 5-membered or 6-membered saturated or unsaturated heterocyclene selected from the group of:

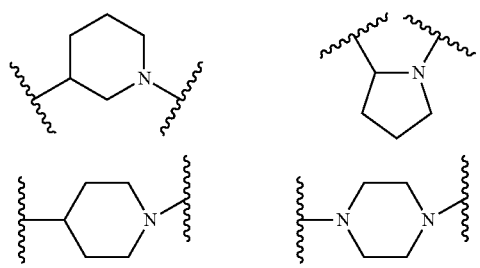

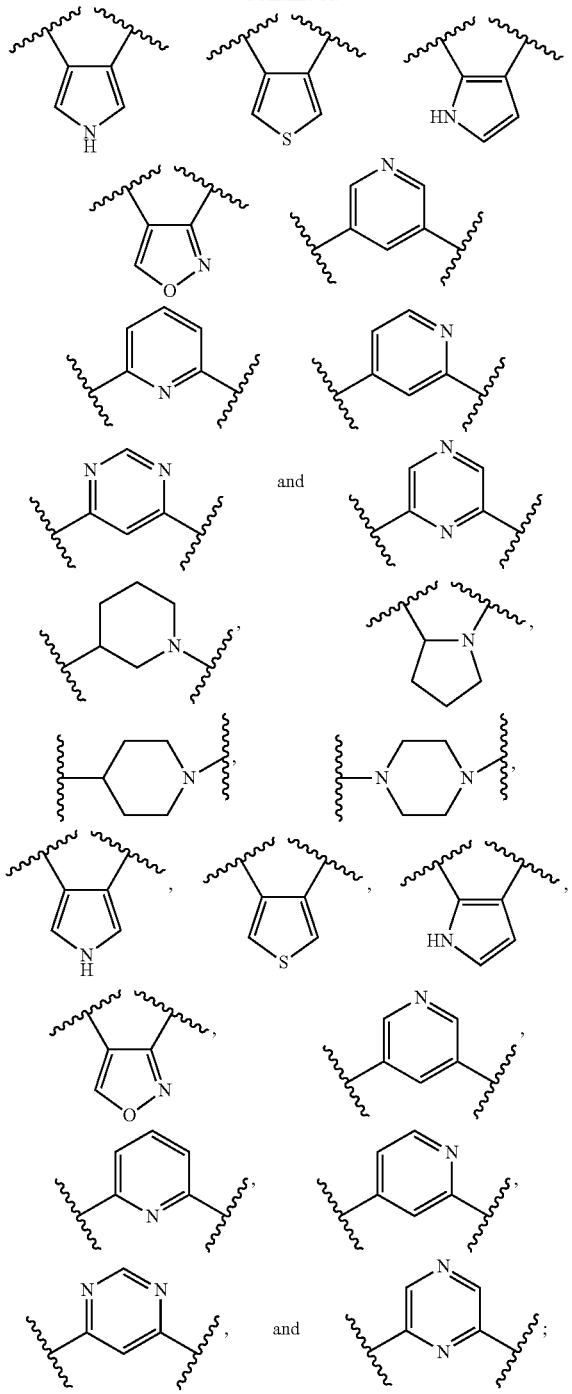

and wherein said 5-membered or 6-membered saturated or unsaturated heterocyclene is optionally substituted with 1, 2, or 3 substituents selected from halo, alkyl, alkoxy, oxo, and OH;

$R^4$ is $C_{1-10}$alkylene, $C_{2-10}$alkenylene, or $C_{2-10}$alkynylene wherein each $R^4$ is optionally substituted with 1, 2, or 3 substituents selected from halo, oxo, and $OR^8$; with the proviso that the total number of carbon atoms in the $C_{1-10}$alkylene, $O_{2-10}$alkenylene, or $C_{2-10}$alkynylene chains of two $R^4$ groups in any definition of $R^3$ is not greater than 12;

Y is C(O), C(O)N(R⁸)CH₂, N(R⁸)C(O), O—C(O)N(R⁸)CH₂, N(R⁸)C(O)N(R⁸)CH₂, or SO₂N(R⁸)CH₂;

R⁵ is alkyl;

R⁶ is H or alkyl;

R⁷ is selected from unsubstituted $C_{3-6}$cycloalkyl, substituted $C_{3-6}$cycloalkyl, and a heterocyclic group selected from formulas (i), (ii), and (iii):

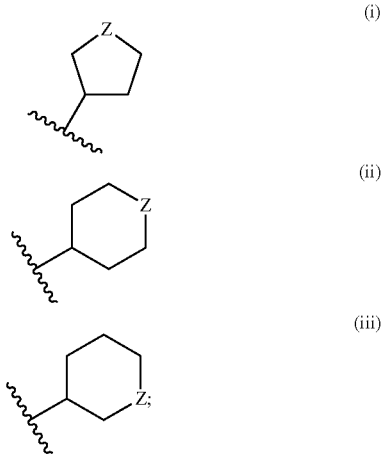

wherein Z is O, S, S(O)₂, NH, or N—R⁷ᵃ, and R⁷ᵃ is selected from alkyl, C(O)alkyl, C(O)NH₂, C(O)N(H)alkyl, and C(O)N(alkyl)₂; and R⁸ is H or alkyl.

2. The compound according to claim 1, or a pharmaceutically acceptable salt thereof, wherein R¹ is CH₂OH and R² is H.

3. The compound according to claim 1, or a pharmaceutically acceptable salt thereof, wherein X is selected from:

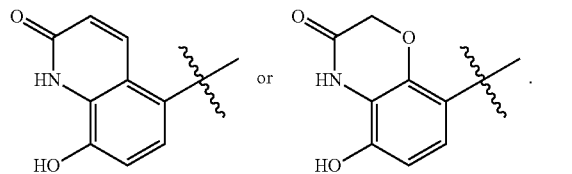 [SMILES: *c1ccc(O)c2[nH]c(=O)ccc12 ; *c1ccc(O)c2c1OCC(=O)N2]

4. The compound according to claim 1 or a pharmaceutically acceptable salt thereof, wherein R³ is selected from $C_{4-12}$alkylene, $C_{4-12}$alkenylene, $C_{4-12}$alkynylene, R⁴—O—R⁴, and R⁴—N(R⁸)—R⁴, wherein said alkylene, alkenylene, or alkynylene are each optionally substituted with 1, 2, or 3 substituents selected from halo, oxo, and OR⁸.

5. The compound according to claim 1, or a pharmaceutically acceptable salt thereof, wherein R³ is selected from $C_{5-8}$alkylene, $C_{5-8}$alkenylene, $C_{5-8}$alkynylene, R⁴—O—R⁴, and R⁴—N(R⁸)—R⁴ wherein each $C_{5-8}$alkylene, $C_{5-8}$alkenylene, $C_{5-8}$alkynylene is optionally substituted with 1 or 2 substituents selected from halo, oxo, and OR⁸; and each R⁴ is selected from $C_{1-4}$alkylene, $C_{2-4}$alkenylene, or $C_{2-4}$alkynylene, each optionally substituted with 1 or 2 substituents selected from halo, oxo, and OR⁸.

6. The compound according to claim 1, or a pharmaceutically acceptable salt thereof, wherein R³ is unsubstituted $C_{5-8}$alkylene.

7. The compound according to claim 1, or a pharmaceutically acceptable salt thereof, wherein R³ is selected from phenylene, R⁴-phenylene, phenylene-R⁴, R⁴-phenylene-R⁴, Het, R⁴-Het, and R⁴-Het-R⁴.

8. The compound according to claim 1, or a pharmaceutically acceptable salt thereof, wherein R³ is selected from R⁴-phenylene, Het, R⁴-Het, and R⁴-Het-R⁴.

9. The compound according to claim 1, or a pharmaceutically acceptable salt thereof, wherein R³ is selected from R⁴-phenylene, R⁴-phenylene-R⁴, Het, R⁴-Het, and R⁴-Het-R⁴.

10. The compound according to claim 1, or a pharmaceutically acceptable salt thereof, wherein R³ is selected from R⁴-phenylene, Het, and R⁴-Het.

11. The compound according to claim 1, or a pharmaceutically acceptable salt thereof, wherein Y is C(O)N(R⁸)CH₂.

12. The compound according to claim 1, or a pharmaceutically acceptable salt thereof, wherein R⁵ is —CH₂CH₃.

13. The compound according to claim 1, or a pharmaceutically acceptable salt thereof, wherein R⁶ is —CH₂CH₃.

14. The compound according to claim 1, or a pharmaceutically acceptable salt thereof, wherein R⁷ is

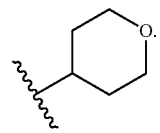 [SMILES: *C1CCOCC1]

15. A compound selected from

N-[[1,6-Diethyl-4-[(tetrahydro-2H-pyran-4-yl)amino]-1H-pyrazolo[3,4-b]pyridine-5-yl]methyl]-3-[2-[[(R)-2-hydroxy-2-[4-hydroxy-3-(hydroxymethyl)phenyl]ethyl]amino]propyl]benzamide;

(R)—N-[[1,6-Diethyl-4-[(tetrahydro-2H-pyran-4-yl)amino]-1H-pyrazolo[3,4-b]pyridin-5-yl]methyl]-3-[2-[[2-hydroxy-2-[4-hydroxy-3-(hydroxymethyl)phenyl]ethyl]amino]-2-methylpropyl]benzamide;

(R)—N-[[1,6-Diethyl-4-[(tetrahydro-2H-pyran-4-yl)amino]-1H-pyrazolo[3,4-b]pyridin-5-yl]methyl]-3-[2-[[2-hydroxy-2-(8-hydroxy-2-oxo-1,2-dihydroquinolin-5-yl)ethyl]amino]-2-methylpropyl]benzamide;

(R)—N-[[1,6-Diethyl-4-[(tetrahydro-2H-pyran-4-yl)amino]-1H-pyrazolo[3,4-b]pyridin-5-yl]methyl]-3-[[[2-hydroxy-2-(8-hydroxy-2-oxo-1,2-dihydroquinolin-5-yl)ethyl]amino]methyl]benzamide;

(R)—N-[[1,6-diethyl-4-[(tetrahydro-2H-pyran-4-yl)amino]-1H-pyrazolo[3,4-b]pyridin-5-yl]methyl]-4-[[[2-hydroxy-2-(8-hydroxy-2-oxo-1,2-dihydroquinolin-5-yl)ethyl]amino]methyl]benzamide;

(R)—N-[[1,6-Diethyl-4-[(tetrahydro-2H-pyran-4-yl)amino]-1H-pyrazolo[3,4-b]pyridin-5-yl]methyl]-3-[[[2-hydroxy-2-[4-hydroxy-3-(hydroxymethyl)phenyl]ethyl]amino]methyl]benzamide;

(R)—N-[[1,6-diethyl-4-[(tetrahydro-2H-pyran-4-yl)amino]-1H-pyrazolo[3,4-b]pyridin-5-yl]methyl]-4-[[[2-hydroxy-2-[4-hydroxy-3-(hydroxymethyl)phenyl]ethyl]amino]methyl]benzamide;

(R)—N-[[1,6-diethyl-4-[(tetrahydro-2H-pyran-4-yl)amino]-1H-pyrazolo[3,4-b]pyridin-5-yl]methyl]-4-[5-[[2-hydroxy-2-(8-hydroxy-2-oxo-1,2-dihydroquinolin-5-yl)ethyl]amino]pentyl]benzamide;

(R)—N-[[1,6-Diethyl-4-[(tetrahydro-2H-pyran-4-yl)amino]-1H-pyrazolo[3,4-b]pyridin-5-yl]methyl]-8-[[2-hydroxy-2-(8-hydroxy-2-oxo-1,2-dihydroquinolin-5-yl)ethyl]amino]octanamide;

(R)-1-((1,6-diethyl-4-((tetrahydro-2H-pyran-4-yl)amino)-1H-pyrazolo[3,4-b]pyridin-5-yl)methyl)-3-(4-

(5-((2-hydroxy-2-(8-hydroxy-2-oxo-1,2-dihydroquinolin-5-yl)ethyl)amino)pent-1-yn-1-yl)phenyl)urea;

(R)-1-((1,6-diethyl-4-((tetrahydro-2H-pyran-4-yl)amino)-1H-pyrazolo[3,4-b]pyridin-5-yl)methyl)-3-(4-(5-((2-hydroxy-2-(8-hydroxy-2-oxo-1,2-dihydroquinolin-5-yl)ethyl)amino)pentyl)phenyl)urea;

(R)-3-(((1,6-diethyl-4-((tetrahydro-2H-pyran-4-yl)amino)-1H-pyrazolo[3,4-b]pyridin-5-yl)methyl)amino)-4-((4-(5-((2-hydroxy-2-(8-hydroxy-2-oxo-1,2-dhydroquinolin-5-yl)ethyl)amino)pentyl)phenyl)amino)cyclobut-3-ene-1,2-dione;

(R)-1-((1,6-diethyl-4-((tetrahydro-2H-pyran-4-yl)amino)-1H-pyrazolo[3,4-b]pyridin-5-yl)methyl)-3-(4-(4-((6-((2-hydroxy-2-(8-hydroxy-2-oxo-1,2-dihydroquinolin-5-yl)ethyl)amino)hexyl)oxy)butyl)phenyl)urea;

(R)-1-((1,6-diethyl-4-((tetrahydro-2H-pyran-4-yl)amino)-1H-pyrazolo[3,4-b]pyridin-5-yl)methyl)-3-(4-(5-((2-hydroxy-2-(5-hydroxy-3-oxo-3,4-dihydro-2H-benzo[b][1,4]oxazin-8-yl)ethyl)amino)pent-1-yn-1-yl)phenyl)urea;

(R)-1-Ethyl-N-[4'-[[[2-(3-formamido-4-hydroxyphenyl)-2-hydroxyethyl]amino]methyl]biphenyl-4-yl]-4-[(tetrahydro-2H-pyran-4-yl)amino]-1H-pyrazolo[3,4-b]pyridine-5-carboxamide;

(R)-8-[2-[2-[4-[1-Ethyl-4-(tetrahydro-2H-pyran-4-ylamino)-1H-pyrazolo[3,4-b]pyridine-5-carbonyl]piperazin-1-yl]ethylamino]-1-hydroxyethyl]-5-hydroxy-2H-benzo[b][1,4]oxazin-3(4H)-one;

(R)—N-[[1,6-diethyl-4-(tetrahydro-2H-pyran-4-ylamino)-1H-pyrazolo[3,4-b]pyridin-5-yl]methyl]-6-[4-[2-hydroxy-2-(8-hydroxy-2-oxo-1,2-dihydroquinolin-5-yl)ethylamino]butoxy]nicotinamide;

(R)—N-((1,6-diethyl-4-((tetrahydro-2H-pyran-4-yl)amino) H-pyrazolo[3,4-b]pyridin-5-yl)methyl)-4-(5-((2-hydroxy-2-(4-hydroxy-3-(methylsulfonamido)phenyl)ethyl)amino)pentyl)benzamide;

(R)-6-((2-hydroxy-2-(8-hydroxy-2-oxo-1,2-dihydroquinolin-5-yl)ethyl)amino)hexyl((1,6-diethyl-4-((tetrahydro-2H-pyran-4-yl)amino)-1H-pyrazolo[3,4-b]pyridin-5-yl)methyl)carbamate;

or a pharmaceutically acceptable salt thereof.

16. A composition comprising a compound of claim 1, or a pharmaceutically acceptable salt thereof, and a pharmaceutically acceptable carrier, diluent or excipient.

17. The composition according to claim 16, wherein said composition is suitable for inhalation.

18. The composition according to claim 16 further comprising a therapeutically active agent selected from anti-inflammatory agents, anticholinergic agents, peroxisome proliferator-activated receptor agonists, epithelial sodium channel blockers, kinase inhibitors, protease inhibitors, anti-infective agents and antihistamines.

* * * * *